(12) United States Patent
Quay et al.

(10) Patent No.: US 9,731,016 B2
(45) Date of Patent: Aug. 15, 2017

(54) TYROSINE-BASED LIPIDS FOR DELIVERY OF THERAPEUTICS

(71) Applicant: Marina Biotech, Inc., Bothell, WA (US)

(72) Inventors: Steven C. Quay, Seattle, WA (US); Michael E. Houston, Jr., Sammamish, WA (US); Pierrot Harvie, Bothell, WA (US); Roger C. Adami, Bothell, WA (US); Renata Fam, Kenmore, WA (US); Mary Prieve, Lake Forest Park, WA (US); Kathy Fosnaugh, Bellevue, WA (US); Shaguna Seth, Bothell, WA (US)

(73) Assignee: Marina Biotech, Inc., City of Industry, CA (US)

( * ) Notice: Subject to any disclaimer, the term of this patent is extended or adjusted under 35 U.S.C. 154(b) by 0 days.

(21) Appl. No.: 15/089,568

(22) Filed: Apr. 3, 2016

(65) Prior Publication Data

US 2016/0206739 A1    Jul. 21, 2016

Related U.S. Application Data

(60) Continuation of application No. 14/496,200, filed on Sep. 25, 2014, now Pat. No. 9,339,461, which is a
(Continued)

(51) Int. Cl.
*A61K 47/18* (2017.01)
*A61K 48/00* (2006.01)
(Continued)

(52) U.S. Cl.
CPC ............ *A61K 47/183* (2013.01); *A61K 9/127* (2013.01); *A61K 9/1272* (2013.01);
(Continued)

(58) Field of Classification Search
CPC .... A61K 9/1272; A61K 31/165; A61K 47/18; A61K 47/44; A61K 48/0033;
(Continued)

(56) References Cited

U.S. PATENT DOCUMENTS

| 4,844,884 A | 7/1989 | Tur |
| 5,190,782 A | 3/1993 | Yarger |

(Continued)

FOREIGN PATENT DOCUMENTS

| DE | 2064480 | 7/1971 |
| DE | 4311806 A1 | 6/1994 |

(Continued)

OTHER PUBLICATIONS

Yoshiizumi et al. Studies on Scavenger Receptor Inhibitors. Part 1 . . . Bioorganic & Medicinal Chemistry. 2002, vol. 10, pp. 2445-2460.*

(Continued)

*Primary Examiner* — Jeffrey E Russel
(74) *Attorney, Agent, or Firm* — Eckman Law Group

(57) ABSTRACT

This disclosure provides a range of tyrosine amino acid lipid compounds and compositions useful for drug delivery, therapeutics, and the diagnosis and treatment of diseases and conditions. The amino acid lipid compounds and compositions can be used for delivery of various agents such as nucleic acid therapeutics to cells, tissues, organs, and subjects.

17 Claims, 5 Drawing Sheets

Related U.S. Application Data division of application No. 13/933,110, filed on Jul. 1, 2013, now Pat. No. 8,877,729, which is a continuation of application No. 13/076,158, filed on Mar. 30, 2011, now Pat. No. 8,501,824, which is a division of application No. 12/114,284, filed on May 2, 2008, now Pat. No. 7,939,505.

(60) Provisional application No. 61/022,571, filed on Jan. 22, 2008, provisional application No. 60/972,653, filed on Sep. 14, 2007, provisional application No. 60/972,590, filed on Sep. 14, 2007, provisional application No. 60/953,667, filed on Aug. 2, 2007, provisional application No. 60/947,282, filed on Jun. 29, 2007, provisional application No. 60/916,131, filed on May 4, 2007.

(51) Int. Cl.
| | | |
|---|---|---|
| C07C 235/02 | (2006.01) | |
| C12N 15/88 | (2006.01) | |
| C07D 213/56 | (2006.01) | |
| C07C 279/14 | (2006.01) | |
| C07D 213/40 | (2006.01) | |
| C07D 233/26 | (2006.01) | |
| C12N 15/11 | (2006.01) | |
| A61K 47/44 | (2017.01) | |
| C12N 15/113 | (2010.01) | |
| A61K 31/7088 | (2006.01) | |
| A61K 47/22 | (2006.01) | |
| C07D 233/64 | (2006.01) | |
| A61K 47/28 | (2006.01) | |
| C07C 279/12 | (2006.01) | |
| A61K 9/127 | (2006.01) | |

(52) U.S. Cl.
CPC .......... *A61K 31/7088* (2013.01); *A61K 47/18* (2013.01); *A61K 47/22* (2013.01); *A61K 47/28* (2013.01); *A61K 47/44* (2013.01); *A61K 48/0025* (2013.01); *A61K 48/0033* (2013.01); *C07C 235/02* (2013.01); *C07C 279/12* (2013.01); *C07C 279/14* (2013.01); *C07D 213/40* (2013.01); *C07D 213/56* (2013.01); *C07D 233/26* (2013.01); *C07D 233/64* (2013.01); *C12N 15/111* (2013.01); *C12N 15/113* (2013.01); *C12N 15/1131* (2013.01); *C12N 15/1138* (2013.01); *C12N 15/88* (2013.01); *A61K 9/1271* (2013.01); *C12N 2310/14* (2013.01); *C12N 2320/32* (2013.01); *Y10S 514/943* (2013.01)

(58) Field of Classification Search
CPC ... C07C 235/00; C07C 235/02; C07C 237/04; C07C 237/16; C12N 15/88; C12N 15/111
See application file for complete search history.

(56) References Cited

U.S. PATENT DOCUMENTS

| | | | |
|---|---|---|---|
| 5,310,542 A | 5/1994 | Au et al. | |
| 5,357,026 A | 10/1994 | Younes | |
| 5,504,228 A | 4/1996 | Morelle et al. | |
| 5,658,885 A | 8/1997 | Lee et al. | |
| 5,831,005 A | 11/1998 | Zuckerman et al. | |
| 5,849,276 A | 12/1998 | Guskey et al. | |
| 5,935,936 A | 8/1999 | Fasbender et al. | |
| 5,965,188 A | 10/1999 | Bland et al. | |
| 5,977,301 A | 11/1999 | Zuckerman et al. | |
| 5,980,935 A | 11/1999 | Kirpotin et al. | |
| 6,030,946 A | 2/2000 | Klaus et al. | |
| 6,287,591 B1 | 9/2001 | Semple et al. | |
| 6,335,468 B1 | 1/2002 | Hatajima et al. | |
| 6,379,965 B1 | 4/2002 | Boutin | |
| 6,458,381 B1 | 10/2002 | Sourovoi et al. | |
| 6,656,499 B1 | 12/2003 | Foldvari et al. | |
| 6,749,863 B1 | 6/2004 | Chang et al. | |
| 6,815,432 B2 | 11/2004 | Wheeler et al. | |
| 6,858,225 B2 | 2/2005 | Semple et al. | |
| 7,312,206 B2 | 12/2007 | Panzner et al. | |
| 7,335,509 B2 | 2/2008 | Huang et al. | |
| 7,341,738 B2 | 3/2008 | Semple et al. | |
| 7,371,404 B2 | 5/2008 | Panzner et al. | |
| 7,939,505 B2* | 5/2011 | Quay ................... | A61K 9/1272 514/44 A |
| 8,501,824 B2* | 8/2013 | Quay ................... | A61K 9/1272 424/450 |
| 8,877,729 B2* | 11/2014 | Quay ................... | A61K 9/1272 514/44 A |
| 9,339,461 B2* | 5/2016 | Quay ................... | A61K 9/1272 |
| 2003/0130237 A1 | 7/2003 | Miller et al. | |
| 2004/0131666 A1 | 7/2004 | Panzner et al. | |
| 2004/0204377 A1 | 10/2004 | Rana | |
| 2005/0064595 A1 | 3/2005 | MacLachlan et al. | |
| 2005/0186586 A1 | 8/2005 | Zamore et al. | |
| 2005/0239687 A1 | 10/2005 | Divita | |
| 2005/0287627 A1 | 12/2005 | Hashimoto et al. | |
| 2006/0009507 A1 | 1/2006 | Miller et al. | |
| 2006/0211637 A1 | 9/2006 | Scaria et al. | |
| 2007/0129305 A1 | 6/2007 | Divita | |
| 2007/0260055 A1 | 11/2007 | Rana | |
| 2008/0020058 A1 | 1/2008 | Chen et al. | |

FOREIGN PATENT DOCUMENTS

| | | | |
|---|---|---|---|
| EP | 0136879 A2 | 4/1985 | |
| EP | 0320976 A1 | 6/1989 | |
| EP | 0490379 A2 | 12/1991 | |
| EP | 0763592 A1 | 3/1997 | |
| EP | 0805147 A1 | 5/1997 | |
| EP | 1060739 A1 | 12/2000 | |
| EP | 1264591 A2 | 12/2002 | |
| EP | 1325735 A2 | 7/2003 | |
| EP | WO 2010/045512 R | 8/2010 | |
| GB | 2355013 | 11/2001 | |
| JP | 63-189288 A | 8/1988 | |
| JP | 02088549 | 3/1990 | |
| JP | 04026662 | 1/1992 | |
| JP | 2000128725 | 5/2000 | |
| JP | 2000128725 | 9/2000 | |
| WO | 9101724 A1 | 2/1991 | |
| WO | 9403468 A1 | 2/1994 | |
| WO | 9640737 A1 | 12/1996 | |
| WO | 9705865 A1 | 2/1997 | |
| WO | WO9725070 A | 7/1997 | |
| WO | 9743363 A1 | 11/1997 | |
| WO | 9915506 A1 | 4/1999 | |
| WO | 9933787 A1 | 8/1999 | |
| WO | 9952936 A2 | 10/1999 | |
| WO | 0015206 A2 | 3/2000 | |
| WO | 0073471 A1 | 12/2000 | |
| WO | 0171022 A2 | 9/2001 | |
| WO | 0198362 A2 | 12/2001 | |
| WO | 0202538 A1 | 1/2002 | |
| WO | WO02053583 A | 7/2002 | |
| WO | 02072068 A2 | 9/2002 | |
| WO | 02078448 A1 | 10/2002 | |
| WO | 03024402 A2 | 3/2003 | |
| WO | 03091276 A2 | 11/2003 | |
| WO | 03091276 A3 | 11/2003 | |
| WO | 03106636 A2 | 12/2003 | |
| WO | 2005032494 A2 | 4/2005 | |
| WO | 2005039629 A2 | 5/2005 | |
| WO | 2005068488 A1 | 7/2005 | |
| WO | 2005105152 | 10/2005 | |
| WO | 2005102997 A1 | 11/2005 | |
| WO | 2006001381 A1 | 5/2006 | |
| WO | 2006082978 A1 | 10/2006 | |
| WO | 2007001455 | 1/2007 | |
| WO | 2007027742 A2 | 3/2007 | |

(56) References Cited

FOREIGN PATENT DOCUMENTS

| WO | 2007039736 A1 | 4/2007 |
|---|---|---|
| WO | 2008042973 | 4/2008 |
| WO | WO2009046220 A2 | 4/2009 |
| WO | WO 2009/046220 R | 10/2009 |

OTHER PUBLICATIONS

Epand, R. et al., "Properties of lipoamino acids incorporated into membrane bilayers," Biochimica et Biophysica Acta, v. 1373, No. 1, pp. 67-75, Elsevier, 1998.
Heyes, J. et al., "Cationic lipid saturation influences intracellular delivery of encapsulated nucleic acids," Journal of Controlled Release, v. 107, No. 2, pp. 276-287, Elsevier, 2005.
MacDonald, M. et al., "Physical and Biological Properties of Cationic Triesters of Phosphatidylcholine," Biophysical Journal, v. 77, pp. 2612-2629, 1999.
Reshetnyak, Y. et al., "Translocation of molecules into cells by pH-dependent insertion of a transmembrane helix," PNAS, v. 103, No. 17, pp. 6460-6465, 2006.
Rossi, J., "SNALPing siRNAs in vivo," Gene Therapy, v. 13, pp. 583-584, Nature Publishing Group, 2005.
Saleh, M. et al., "The endocytic pathway mediates cell entry of dsRNA to induce RNAi silencing," Nature Cell Biology, v. 8, No. 8, pp. 793-802, 2006.
Hafez, I. et al. "Tunable pH-Sinsitive Liposomes Composed of Mixtures of Cationic and Anionic Lipids," Biophysical Journal, v. 79, No. 3, pp. 1438-1446, 2000.
Wang, K. et al. "Synthesis and in vitro Behavior of Multivalent Cationic Lipopeptide for DNA Delivery and Release in HeLa Cells," Bioconjugate Chemistry, v. 18, No. 6, pp. 1735-1738, American Chemical Society, 2007.
Gonzalez, H. et al., "New Class of Polymers for the Delivery of Macromolecular Therapeutics," Bioconjugate Chemistry, v. 10, pp. 1068-1074, 1999.
Thomas, M., et al., "Non-viral siRNA delivery to the lung" Advanced Drug Delivery Reviews 59 (2007) pp. 124-133.
Thomas, M., et al., "Full deacylation of polyethylenimine dramatically boosts its gene delivery efficiency and specificity to mouse lung" PNAS , v. 102 No. 16, 2005.
Prata, C., et al., "Lipophilic Peptides for Gene Delivery" Bioconjugate Chem., vol. 19, No. 2, 2008.
Rudraksh, S., et al., "Molecular modeling of arginine-glycine-aspartic acid (RGD) analogs Relevance to Transepithelial transport" J Pharm Pharmaceut Sci (www.ualberta.ca/~csps) 4(1):32-41, 2001.
Opal, S., et al., "Lipopolyamines as a therapeutic strategy in experimental Gram-negative bacterial sepsis" Journal of Endotoxin Research, v. 7, No. 1, pp. 35-39, 2001.
Ma, B., et al. "Lipoplex morphologies and their influences on transfection efficiency in gene delivery" Journal of Controlled Release, 123, pp. 184-194, 2007.
Yaghmur, A., et al., "Tuning Curvature and Stability of Monoolein Bilayers by Designer Lipid-Like Peptide Surfactants" PLoS ONE 2(5): e479. doi:10.1371/joumal.pone.0000479, (May 2007).
David, S., et al. "Lipopolyamines: Novel Antiendotoxin Compounds That Reduce Mortality in Experimental Sepsis Caused by Gram-Negative Bacteria" Antimicrobial Agents and Chemotherapy, v.43 No. 4, pp. 912-919, 1999.
Bedford, M., et al. "Arginine Methylation: An Emerging Regulator of Protein Function" Molecular Cell, v. 18, pp. 263-272, 2005.
Vavrova K, et al., "Synthetic ceramide analogues as skin permeation enhancers: structure-activity relationships" Bioorganic & Medicinal Chemistry, Elsevier Science LTD, v. 11, No. 24, pp. 5381-5390, 2003.
Fan, G., et al., "Synthesis of alpha-galactosyl ceramide and the related glycolipids for evaluation of their activities on mouse splenocytes" Tetrahedron, Elsevier Science Publishers, v. 61, No. 7, pp. 1855-1862, 2005.
Polidori, A.., et al., "Vesicles and other supramolecular systems made from double-tailed synthetic glycolipids derived from galactosylated tris (hydroxymethyl) aminomethane" Chemistry and Physics of Lipids, v. 77, No. 2, pp. 225-251, 1995.
Tonges, L., et al., "Stearylated octaarginine and artificial virus-like particles for transfection of siRNA into primary rat neurons" RNA, v. 12, No. 7, pp. 1431-1438, 2006.
Sommerdijk, M., et al., "Boomerang shaped aggregates from histidine surfactant" Chem. Commun., pp. 455-456, 1997.
Heyes, J., et al., "Synthesis of novel cationic lipids: Effect of structural modification on the efficiency of gene transfer" Journal of Medicinal Chemistry, US American Chemical Society, v. 45, No. 1, pp. 99-114, 2002.
Kumar, V., et al. "Single histidine residue in head-group region is sufficient to impart remarkable gene transfection properties to cationic lipids: Evidence for histidine-mediated membrane fusion at acidic pH" Gene Therapy, Macmillan Press Ltd., v. 10, No. 15, pp. 1206, 2003.
Martin, B., et al., "The design of cationic lipids for gene delivery" Current Pharmaceutical Design, v.11, No. 3, pp. 375-394, 2005.
Sommerdijk, M., et al., "Supramolecular expression of chirality in assemblies of gemini surfactants" Chem. Comm., pp. 1423-1424, 1997.
Gao, H., et al., "Synthesis of a novel series of cationic lipids that can act as efficient gene delivery vehicles through systematic heterocyclic substitution of cholesterol derivatives" Gene Therapy, v. 8, No. 11, pp. 855-863, 2001.
Meekel, A., et al., "Synthesis of pyridium amphiphiles used for transfection and some characteristics of amphiphile/DNA complex formation" European Journal of Organic Chemistry, Wiley-Vch, No. 4, pp. 665-673, 2000.
Karmali, P., et al., "Cationic liposomes as non-viral carriers of gene medicines: Resolved issues, open questions, and future promises" Medicinal Research Reviews, v. 27, No. 5, pp. 696-722, 2006.
Gascon, A., et al., "Cationic lipids as gene transfer agents: a patent review" Expert Opin. Ther. Patents, v. 18, No. 5, pp. 515-521, 2008.
Fan, European Food Research and Technol., 2007, V. 227(1): 167-174.
Frederiksen, Journal of Pharmaceutical Sciences, 1997, V. 86(8): 921-928.
Gabizon, Journal of Liposome Research, 2006, V. 16(3): 175-183.
Mainardes, Current Drug Delivery, 2006, V. 3(3): 275-285.
Maitani, International Journal of Pharmaceutics, 2007, V. 342(1-2): 33-39.
Maitani, Journal of Liposome Research, 2001, V. 11(1): 115-125.
Pons, International Journal of Pharmaceutics, 1993, V. 95(1-3): 51-56.
Sharma, International Journal of Pharmaceutics, 1997, V. 154(2): 123-140.
Skalko, European Journal of Pharmaceutical Sciences, 1996, V. 4(6): 359-366.
Futaki, Bioconjugate Chemistry, 2001, vol. 12(6): 1005-1011.
Khalil, Gene Therapy 2004, vol. 11(7): 636-644.
Mitchell, Journal of Peptide research, 2000, vol. 56(5), 318-325.
Leng, Cancer Gene Therapy, 2005, vol. 12(8): 682-690.
Denoyelle, et al., Synthesis and preliminary biological studies of hemifluorinated bifunctional bolaamphiphiles designed for gene delvery. New Journal of Chemistry. Feb 9, 2006, vol. 30, pp. 629-646.
Sommerdijk et al. Supramolecular expression of chirality in assemblies of gemini surfactants. Chemical Communications. 1997, pp. 1423-1424.
Sommerdijk et al. Boomerang shaped aggregates from a histidine surfactant. Chemical Communications. 1997, pp. 455-456.

* cited by examiner

TYROSINE-BASED LIPIDS FOR DELIVERY OF THERAPEUTICS

SEQUENCE LISTING

This application includes a Sequence Listing submitted herewith via EFS as an ASCII file created on Sep. 24, 2014, named MAR278US_Seq_List.txt, which is 7179 bytes in size, and is hereby incorporated by reference in its entirety.

BACKGROUND

The delivery of a therapeutic compound to a subject can be impeded by limited ability of the compound to reach a target cell or tissue, or by restricted entry or trafficking of the compound within cells. Delivery of a therapeutic material is in general restricted by membranes of cells. These barriers and restrictions to delivery can result in the need to use much higher concentrations of a compound than is desirable to achieve a result, which brings the risk of toxic effects and side effects.

One strategy for delivery is to improve transport of a compound into cells using lipid or polymeric carrier molecules. These materials can take advantage of mechanisms that exist for selective entry into a cell, while still excluding exogenous molecules such as nucleic acids and proteins. For example, a cationic lipid may interact with a drug agent and provide contact with a cell membrane. Lipid molecules can also be organized into liposomes or particles as carriers for drug agents. Liposomal drug carriers can protect a drug molecule from degradation while improving its uptake by cells. Also, liposomal drug carriers can encapsulate or bind certain compounds by electrostatic and other interactions, and may interact with negatively charged cell membranes to initiate transport across a membrane.

The understanding of regulatory RNA and the development of RNA interference (RNAi), RNAi therapy, RNA drugs, antisense therapy, and gene therapy, among others, has increased the need for effective means of introducing active nucleic acid agents into cells. In general, nucleic acids are stable for only limited times in cells or plasma. However, nucleic acid-based agents can be stabilized in compositions and formulations which may then be dispersed for cellular delivery.

This disclosure provides compounds, compositions, methods and uses for improving systemic and local delivery of drugs and biologically active molecules. Among other things, this application provides novel compounds and compositions for making and using delivery structures and carriers which increase the efficiency of delivery of biologically active molecules.

BRIEF SUMMARY

This disclosure provides novel compounds, compositions and formulations for intracellular and in vivo delivery of drug agents for use, ultimately, as a therapeutic. The compounds and compositions of this disclosure are useful for delivery of drug agents to selected cells, tissues, organs or compartments in order to alter a disease state or a phenotype.

In some aspects, this disclosure provides compounds, compositions and methods to deliver RNA structures to cells to produce the response of RNA interference, antisense effects, or the regulation of genomic expression.

This invention provides a range of amino acid lipids which are lipophilic compounds for use in delivery and administration of drug agents and in drug delivery systems.

The amino acid lipids of this disclosure are molecules containing an amino acid residue and one or more lipophilic tails.

In some aspects, this invention provides a range of amino acid lipid compounds as shown in Formula I:

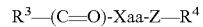

$$R^3-(C=O)-Xaa-Z-R^4 \quad \text{Formula I}$$

wherein
Xaa is any D- or L-amino acid residue having the formula $-NR^N-CR^1R^2-(C=O)-$, or a peptide of n=2-20 amino acid residues having the formula $-\{NR^N-CR^1R^2-(C=O)\}_n-$, wherein
$R^1$ is independently, for each occurrence, a non-hydrogen, substituted or unsubstituted side chain of an amino acid;
$R^2$ is independently, for each occurrence, hydrogen, or an organic group consisting of carbon, oxygen, nitrogen, sulfur, and hydrogen atoms, and having from 1 to 20 carbon atoms, or C(1-5)alkyl, cycloalkyl, cycloalkylalkyl, C(3-5)alkenyl, C(3-5)alkynyl, C(1-5)alkanoyl, C(1-5)alkanoyloxy, C(1-5)alkoxy, C(1-5)alkoxy-C(1-5)alkyl, C(1-5)alkoxy-C(1-5)alkoxy, C(1-5)alkyl-amino-C(1-5)alkyl-, C(1-5)dialkyl-amino-C(1-5)alkyl-, nitro-C(1-5)alkyl, cyano-C(1-5)alkyl, aryl-C(1-5)alkyl, 4-biphenyl-C(1-5)alkyl, carboxyl, or hydroxyl,
$R^N$ is independently, for each occurrence, hydrogen, or an organic group consisting of carbon, oxygen, nitrogen, sulfur, and hydrogen atoms, and having from 1 to 20 carbon atoms, or C(1-5)alkyl, cycloalkyl, cycloalkylalkyl, C(3-5)alkenyl, C(3-5)alkynyl, C(1-5)alkanoyl, C(1-5)alkanoyloxy, C(1-5)alkoxy, C(1-5)alkoxy-C(1-5)alkyl, C(1-5)alkoxy-C(1-5)alkoxy, C(1-5)alkyl-amino-C(1-5)alkyl-, C(1-5)dialkyl-amino-C(1-5)alkyl-, nitro-C(1-5)alkyl, cyano-C(1-5)alkyl, aryl-C(1-5)alkyl, 4-biphenyl-C(1-5)alkyl, carboxyl, or hydroxyl,
$R^3$ is independently a lipophilic tail derived from a naturally-occurring or synthetic lipid, phospholipid, glycolipid, triacylglycerol, glycerophospholipid, sphingolipid, ceramide, sphingomyelin, cerebroside, or ganglioside, wherein the tail may contain a steroid; or a substituted or unsubstituted C(3-22)alkyl, C(6-12)cycloalkyl, C(6-12)cycloalkyl-C(3-22)alkyl, C(3-22)alkenyl, C(3-22)alkynyl, C(3-22)alkoxy, or C(6-12)alkoxy-C(3-22)alkyl;
$R^4$ is independently a lipophilic tail derived from a naturally-occurring or synthetic lipid, phospholipid, glycolipid, triacylglycerol, glycerophospholipid, sphingolipid, ceramide, sphingomyelin, cerebroside, or ganglioside, wherein the tail may contain a steroid; or a substituted or unsubstituted C(3-22)alkyl, C(6-12)cycloalkyl, C(6-12)cycloalkyl-C(3-22)alkyl, C(3-22)alkenyl, C(3-22)alkynyl, C(3-22)alkoxy, or C(6-12)alkoxy-C(3-22)alkyl;
wherein either one of $R^3$ and $R^4$ is a lipophilic tail as defined above and the other is an amino acid terminal group, or both $R^3$ and $R^4$ are lipophilic tails; the amino acid terminal group being hydrogen, hydroxyl, amino, or an organic protective group;
Z is NH, O, S, $-CH_2S-$, $-CH_2S(O)-$, or an organic linker consisting of 1-40 atoms selected from hydrogen, carbon, oxygen, nitrogen, and sulfur atoms;
and salts thereof.

In some respects, this invention provides a range of amino acid lipid compounds as shown in Formula I:

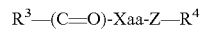

$$R^3-(C=O)-Xaa-Z-R^4 \quad \text{Formula I}$$

wherein
Xaa is a D- or L-amino acid residue having the formula
—NR$^N$—CR$^1$R$^2$—(C=O)—, wherein
R$^1$ is a substituted or unsubstituted basic side chain of an amino acid;
R$^2$ is hydrogen, or C(1-5)alkyl,
R$^N$ is hydrogen, or C(1-5)alkyl,
R$^3$ is independently a substituted or unsubstituted C(6-22)alkyl or C(6-22)alkenyl;
R$^4$ is independently a substituted or unsubstituted C(6-22)alkyl or C(6-22)alkenyl;
Z is NH, O, or an organic linker consisting of 1-40 atoms selected from hydrogen, carbon, oxygen, nitrogen, and sulfur atoms;
and salts thereof.

In some embodiments, the amino acid lipid compound may contain Xaa selected from arginine, homoarginine, norarginine, nor-norarginine, ornithine, lysine, homolysine, histidine, 1-methylhistidine, pyridylalanine, asparagine, N-ethylasparagine, glutamine, 4-aminophenylalanine, the N-methylated versions thereof, and side chain modified derivatives thereof. In some embodiments, the amino acid lipid compound may contain Xaa selected from cysteine and serine.

In certain embodiments, R$^3$ and R$^4$ may be C(6-22)alkyl and may be the same or different. In some embodiments, R$^3$ and R$^4$ may be C(6-22)alkenyl and may be the same or different.

In certain embodiments, Xaa may be a peptide of 2-20 amino acid residues.

In some embodiments, Xaa may have a side chain containing a functional group having a pKa from 5 to 7.5.

In some aspects, the amino acid lipid compound may be a multi-mer of two or more of the amino acid lipid compounds which are crosslinked.

In some embodiments, the amino acid lipid compound may be a conjugate having a peptide conjugated to the side chain of the amino acid residue.

In certain embodiments, the amino acid lipid compound may be attached to an oligomeric or polymeric framework.

In some embodiments, the amino acid lipid compound may be attached to a pharmaceutical drug compound.

In some aspects, this invention provides a range of amino acid lipid compounds as shown in Formula I:

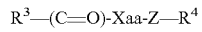
R$^3$—(C=O)-Xaa-Z—R$^4$        Formula I wherein
Xaa is a D- or L-amino acid residue having the formula
—NR$^N$—CR$^1$R$^2$—(C=O)—, wherein
R$^1$ is a substituted or unsubstituted basic side chain of an amino acid;
R$^2$ is hydrogen, or C(1-5)alkyl,
R$^N$ is hydrogen, or C(1-5)alkyl,
R$^3$ is independently a substituted or unsubstituted C(6-22)alkyl or C(6-22)alkenyl;
R$^4$ is hydrogen;
Z is NH, O, or an organic linker consisting of 1-40 atoms selected from hydrogen, carbon, oxygen, nitrogen, and sulfur atoms;
and salts thereof.

In some respects, this disclosure encompasses compositions containing one or more amino acid lipid compounds and one or more therapeutic nucleic acids. The therapeutic nucleic acid may be a gene silencing agent, or an RNAi-inducing agent, or a double-stranded RNA, or an mdRNA, or may contain a modified nucleoside.

In some embodiments, this disclosure encompasses compositions containing one or more amino acid lipid compounds and one or more additional non-amino acid lipids or polymeric lipids. In some embodiments, the composition may contain cholesteryl hemisuccinate.

In some aspects, this disclosure encompasses compositions containing one or more amino acid lipid compounds and one or more nucleic acids which may form a complex with an amino acid lipid.

In certain embodiments, this disclosure encompasses compositions containing one or more amino acid lipid compounds which form liposomes.

In some aspects, this disclosure encompasses compositions containing one or more amino acid lipid compounds which form an emulsion.

In some embodiments, this disclosure encompasses compositions containing one or more amino acid lipid compounds which form a micellar dispersion.

In certain aspects, this disclosure encompasses compositions containing one or more amino acid lipid compounds and one or more drug agents or biologically active agents.

In some aspects, this disclosure encompasses methods for delivering a therapeutic nucleic acid to a cell by preparing a composition containing one or more amino acid lipid compounds and treating a cell with the composition.

In some embodiments, this disclosure encompasses methods for inhibiting expression of a gene in a cell comprising preparing a composition containing one or more amino acid lipid compounds and treating a cell with the composition.

In certain aspects, this disclosure encompasses methods for inhibiting expression of a gene in a mammal comprising preparing a composition containing one or more amino acid lipid compounds and administering the composition to the mammal.

In some embodiments, this disclosure encompasses methods for treating a disease in a human, the disease being selected from rheumatoid arthritis, liver disease, encephalitis, bone fracture, heart disease, viral disease including hepatitis and influenza, and cancer, comprising preparing a composition containing one or more amino acid lipid compounds and administering the composition to the human.

In some aspects, this disclosure encompasses uses of a composition containing one or more amino acid lipid compounds in the preparation of a medicament for treating a disease including rheumatoid arthritis, liver disease, encephalitis, bone fracture, heart disease, viral disease including hepatitis and influenza, and cancer.

In some embodiments, this disclosure encompasses uses of a composition containing one or more amino acid lipid compounds for treating a disease selected from rheumatoid arthritis, liver disease, encephalitis, bone fracture, heart disease, viral disease including hepatitis and influenza, and cancer.

This summary, taken along with the detailed description of the invention, as well as the figures, the appended examples and claims, as a whole, encompass the disclosure of the invention.

The liposomal vesicle contains, in this embodiment, a cargo of active interfering RNA components including a condensed RNA nanoparticle 40, a two-stranded RNA duplex peptide conjugate 50, a three-stranded mdRNA 60, a dicer substrate RNA 70, a dsRNA with a long overhang 80, and an siRNA with blunt ends 90, which are pooled in this embodiment.

Figure 2:
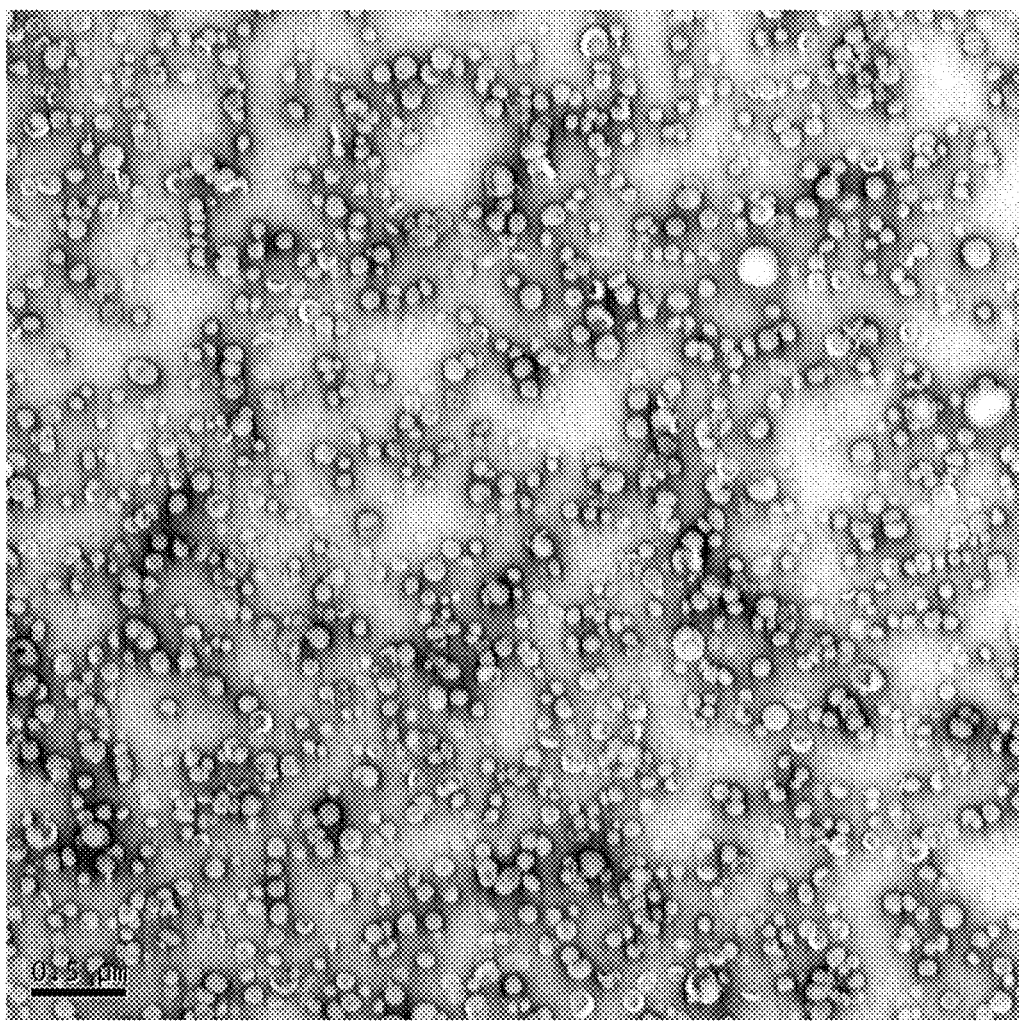

FIG. 2: Transmission electron micrograph obtained on a JEOL 1230 TEM of a liposomal embodiment of this invention showing spherical lipid bilayer vesicle particles formed with the amino acid lipid C12-norArg-C12. The length marker of the micrograph is 0.5 micrometer, and the sample was stained with 3% uranyl acetate. The lipid portion of the liposomal formulation was [C12-norArg($NH_3^+Cl^-$)—C12/DSPC/cholesterol/DSPE-PEG-2000] in the amounts of [30%/20%/49%/1%] respectively, as a mole percent of total lipid. The liposomes contained the antiinfluenza-active dicer substrate dsRNA DX3030.

Figure 3:
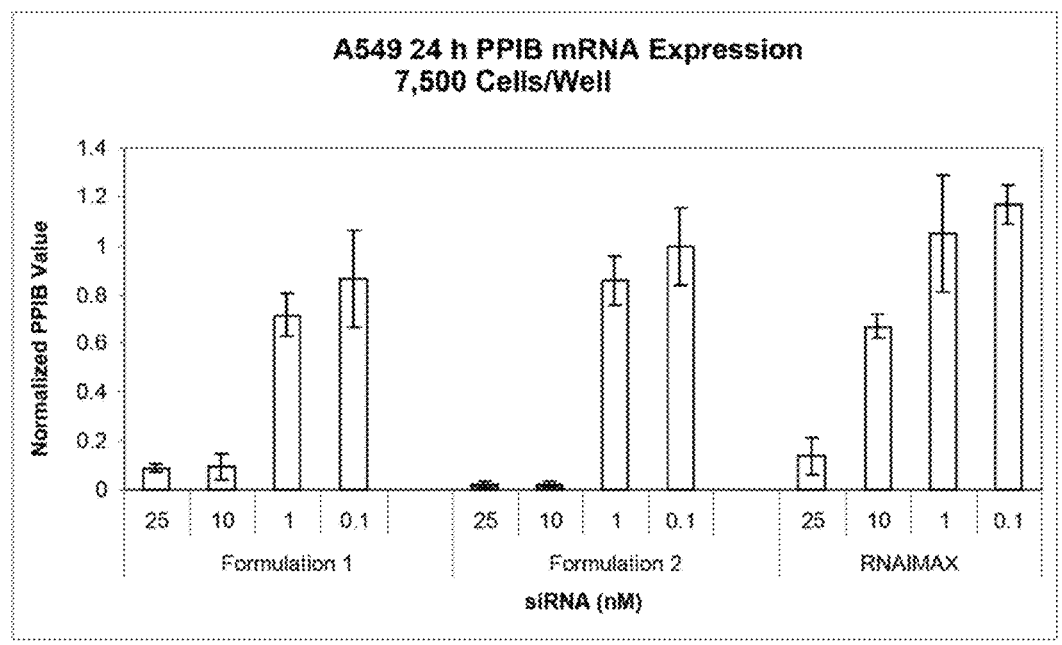

FIG. 3: In FIG. 3 is shown an example of PPIB gene knockdown activity obtained from an in vitro assay in A549 cells. The concentration response at 25, 10, 1, and 0.1 nM RNA of the normalized PPIB mRNA expression values for two amino acid lipid formulations of an interfering-RNA were compared to results for RNAIMAX. Formulation 1 was [C12-norArg($NH_3Cl$)—C12/DOPE/CHOL (50/32/18)] and Formulation 2 was [C12-norArg($NH_3Cl$)—C12/CHEMS/DLPE (50/32/18)]. The PPIB gene knockdown by an interfering-RNA in an amino acid lipid composition of this disclosure can exceed that obtained with RNAIMAX.

Figure 4:
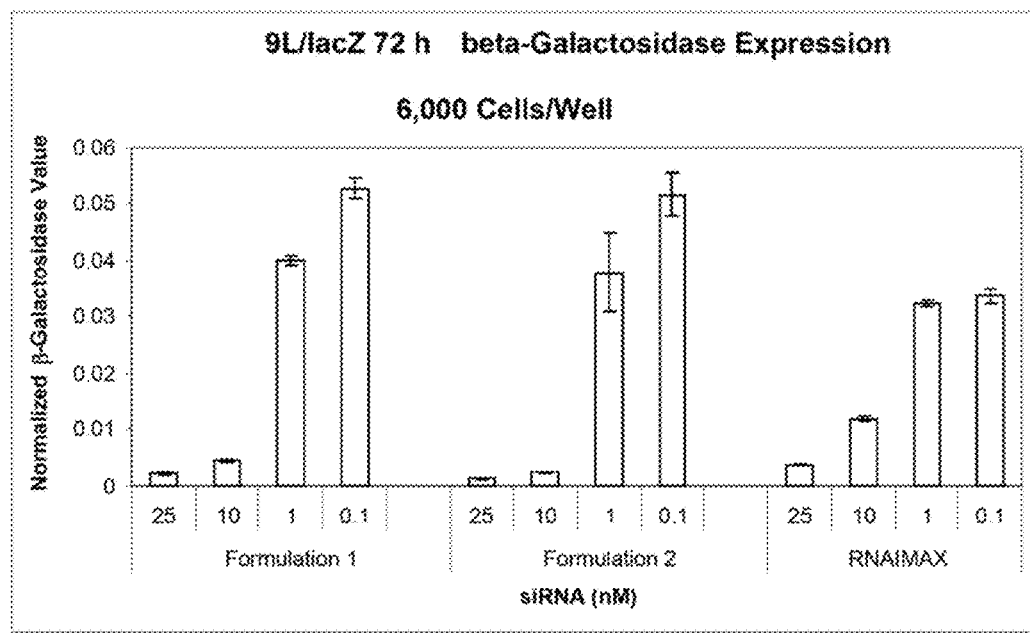

FIG. 4: In FIG. 4 is shown an example of LacZ gene knockdown activity obtained from an in vitro assay in 9L/LacZ cells. The concentration response at 25, 10, 1, and 0.1 nM RNA of the normalized beta-galactosidase expression values for two amino acid lipid formulations of an interfering-RNA were compared to results for RNAIMAX. Formulation 1 was [C12-norArg($NH_3Cl$)—C12/DOPE/CHOL (50/32/18)] and Formulation 2 was [C12-norArg($NH_3Cl$)—C12/CHEMS/DLPE (50/32/18)]. The LacZ gene knockdown by an interfering-RNA in an amino acid lipid composition of this disclosure can exceed that obtained with RNAIMAX.

Figure 5:
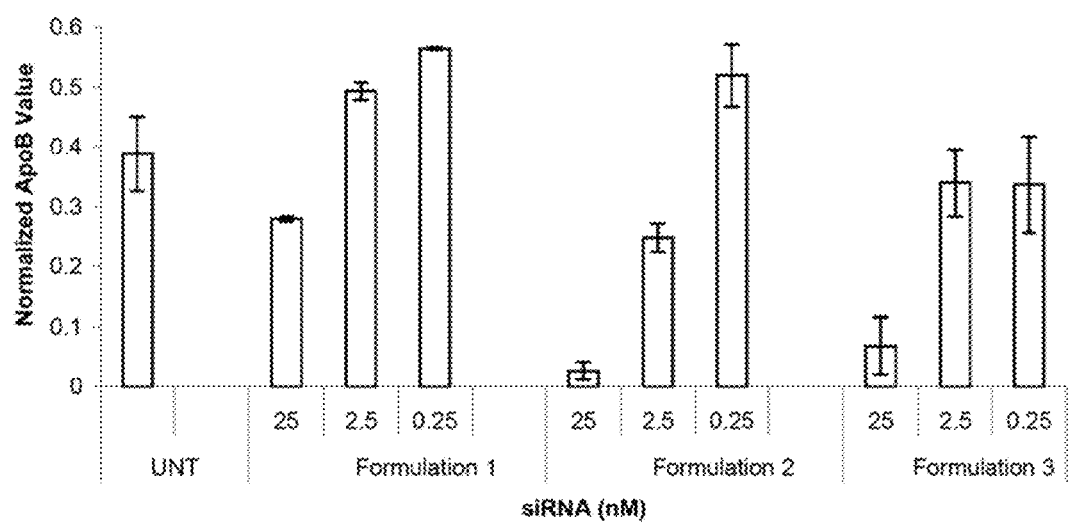

FIG. 5: In FIG. 5 is shown an example of ApoB gene knockdown activity obtained from an in vitro assay in HepG2 cells. The concentration response at 25, 2.5, and 0.25 nM RNA of the normalized ApoB mRNA expression values for three amino acid lipid formulations of an interfering-RNA are shown. Formulation 1 was [non-amino acid cationic lipid/DSPC/chol./DMPE-PEG2k (40/10/48/2)]. Formulation 2 and 3 were both [C18:1-norArg-C16/CHEMS/DLPE/DMPE-PEG2k (50/32/16/2)].

DETAILED DESCRIPTION

This disclosure relates generally to novel compounds, compositions and uses thereof for delivery of drug agents. The compounds and compositions of this disclosure are useful for delivery of therapeutic agents to selected cells, tissues, organs or subjects.

This disclosure relates generally to the chemistry of lipids and uses of lipid-like structures and materials to effect drug delivery.

This invention relates to novel drug delivery enhancing agents including lipids that are useful for delivering various molecules to cells. This invention provides a range of compounds, compositions, formulations, methods and uses of such agents directed ultimately toward drug delivery, therapeutics, and the diagnosis and treatment of diseases and conditions, including those that respond to modulation of gene expression or activity in a subject. More specifically, this invention relates to compounds, liposomes, lamellar vesicles, emulsions, micelles, suspensions, particles, solutions and other forms of delivery enhancing compositions and formulations, as well as therapeutic methods and uses for these delivery materials.

The compounds and compositions of this disclosure are useful for delivery of therapeutic, prophylactic, and diagnostic agents such as nucleic acids, polynucleotides, peptides, proteins, and small molecule compounds and drugs.

The compounds and compositions of this disclosure are useful for delivery of therapeutic agents in forms such as liposomes, lamellar vesicles, emulsions, micelles, suspensions, particles, and solutions. These forms may include nanoparticles of various diameters.

Figure 1:
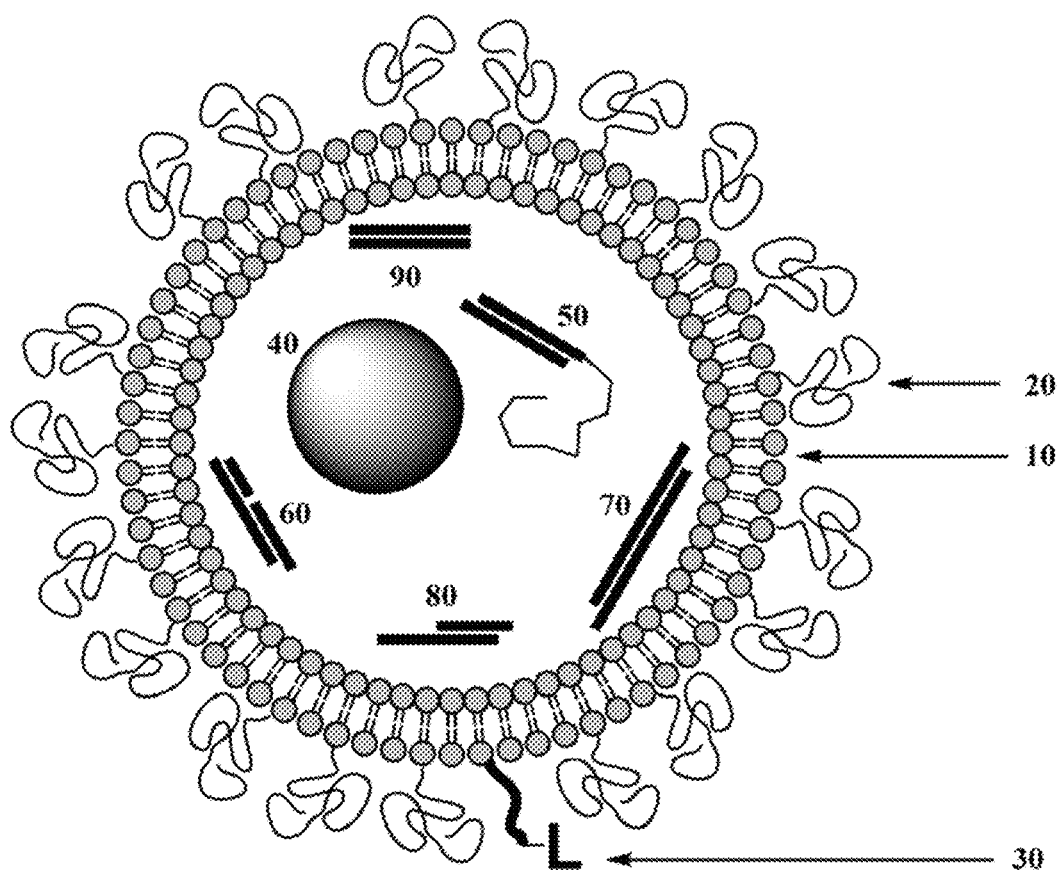
FIG. 1: Schematic representation of a liposomal embodiment of this invention in which amino acid lipids form a bilayer vesicle 10 along with other lipids. In this embodiment, the outer layer of the liposome is protected by polyethyleneglycol chains 20 attached to a head group of one of the lipids. The outer layer of the liposome also presents a ligand 30 for specific targeting of a cell or tissue.

In some respects, the compounds and compositions of this disclosure are useful for delivery of a therapeutic agent in a liposome. In these embodiments the therapeutic agent may be referred to as the cargo. For example, FIG. 1 shows a schematic representation of a liposomal embodiment of this invention in which amino acid lipids form a bilayer vesicle 10 along with other lipids. In this embodiment, the outer layer of the liposome is protected by polyethyleneglycol chains 20 attached to a head group of one of the lipids. The outer layer of the liposome also presents a ligand 30 for specific targeting of a cell or tissue. The liposomal vesicle contains, in this embodiment, a cargo of active interfering RNA components including a condensed RNA nanoparticle 40, a two-stranded RNA duplex peptide conjugate 50, a three-stranded mdRNA 60, a dicer substrate RNA 70, a dsRNA with a long overhang 80, and an siRNA with blunt ends 90, which are pooled in this embodiment. Other forms of therapeutic cargo may include microRNA or hairpin RNA forms.

In some aspects, compounds and compositions of this disclosure may provide delivery of therapeutic agents in releasable forms or compositions. Releasable forms and compositions include molecules that bind and release an active agent, molecules that bind an active agent and discharge a moiety that assists in release of the agent, molecules that bind an active agent and are subsequently modulated in form within a biological compartment to assist in release of the agent, and compositions containing molecules that bind an active agent admixed with a release mediator compound.

Amino Acid Lipids

This invention provides a range of amino acid lipids which are lipophilic compounds for use in delivery and administration of drug agents and in drug delivery systems. The amino acid lipids of this disclosure are molecules containing an amino acid residue and one or more lipophilic tails.

In some embodiments, amino acid lipids are molecules having a hydrophilic portion and a lipophilic portion. The hydrophilic portion may be provided by an amino acid residue. The lipophilic portion can contain one or more lipophilic tails.

In some embodiments, amino acid lipids are lipophilic molecules containing a hydrophobic amino acid residue and one or more lipophilic tails.

In some embodiments, the amino acid lipids provide relatively low cytotoxicity, and correspondingly, a cytoprotective effect relative to certain other lipids. In some embodiments, the amino acid lipids are pharmaceutically-acceptable, biodegradable, or biocompatable.

Amino acid lipids may be formed by substituting a delivery-enhancing or lipid-like tail at either the N-terminus or the C-terminus of an amino acid, or at both termini. In some embodiments, the amino acid core may include one or more amino acids, or may be a peptide of 2-20 amino acid residues.

Amino acid lipids can be cationic or non-cationic, where non-cationic includes neutral and anionic. As used herein, the physical state or ionicity of a species refers to an environment having pH about 7, unless otherwise specified.

Amino acid lipids of this disclosure may exhibit low cytotoxicity. In some embodiments, amino acid lipids of this disclosure may provide cytoprotective effects relative to lipids of other structures.

In some aspects, amino acid lipids of this disclosure may provide delivery of a therapeutic agent in a releasable form. Releasable forms and compositions are designed to provide sufficient uptake of an agent by a cell to provide a therapeutic effect.

Releasable forms include amino acid lipids that bind and release an active agent. In some embodiments, release of the active agent may be provided by an acid-labile linker.

Examples of acid-labile linkers include linkers containing an orthoester group, a hydrazone, a cis-acetonyl, an acetal, a ketal, a silyl ether, a silazane, an imine, a citriconic anhydride, a maleic anhydride, a crown ether, an azacrown ether, a thiacrown ether, a dithiobenzyl group, a cis-aconitic acid, a cis-carboxylic alkatriene, methacrylic acid, and mixtures thereof.

Examples of acid-labile groups and linkers are given in U.S. Pat. Nos. 7,098,032; 6,897,196; 6,426,086; 7,138,382; 5,563,250; and 5,505,931.

Releasable forms of compounds and compositions of this disclosure include molecules that bind an active agent and discharge a moiety that assists in release of the agent.

In some embodiments, an amino acid lipid may include a group which releases a small molecule such as ethanol that assists in delivering an agent to a cell. An amino acid lipid may bind an active agent and, subsequent to contact with a cell, or subsequent to transport within a biological compartment having a local pH lower than physiological pH, be hydrolyzed in an acidic environment to release ethanol to assist in delivery of the agent. In some embodiments, a small molecule such as ethanol, which assists in delivery of the agent, may be bound to a lipid component.

In some embodiments, an amino acid lipid may be admixed with a compound that releases a small molecule such as ethanol to assists in delivering an agent to a cell.

Releasable forms of compounds and compositions of this disclosure include amino acid lipids which may bind an active agent and, subsequent to contact with a cell, or subsequent to transport within a biological compartment having a local pH lower than physiological pH, be modulated in an acidic environment into a cationic form to assist in release of the agent.

In some embodiments, an amino acid lipid may bind an active agent, and may be admixed with a compound that can be modulated in an acidic environment into a cationic form to assist in release of an active agent.

Examples of hydrolysable and modulatable groups are given in U.S. Pat. Nos. 6,849,272; 6,200,599; as well as Z. H. Huang and F. C. Szoka, "Bioresponsive liposomes and their use for macromolecular delivery," in: G. Gregoriadis (ed.), Liposome Technology, 3rd ed. (CRC Press 2006).

In some embodiments, releasable forms of compounds and compositions of this disclosure include amino acid lipids which can bind an active agent, and may be admixed with a lipid or compound that can be modulated in an acidic environment into a neutral form to assist in release of an active agent. The acidic environment may be entered subsequent to contact with a cell, or subsequent to transport within a biological compartment having a local pH lower than physiological pH.

Examples of lipids which are modulatable from anionic to neutral forms include cholesteryl hemisuccinate (CHEMS) as described in U.S. Pat. Nos. 6,897,196; 6,426,086; and 7,108,863.

In some embodiments, releasable forms of compounds and compositions of this disclosure include amino acid lipids which can bind an active agent, and may be admixed with a pH-sensitive polymeric material.

Examples of pH-sensitive polymeric materials are given in U.S. Pat. No. 6,835,393.

In some embodiments, release of the active agent may be provided by an enzyme-cleavable peptide.

In some aspects, this invention provides a range of amino acid lipids as shown in Formula I:

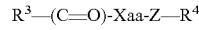

$$R^3-(C=O)\text{-Xaa-Z}-R^4 \qquad \text{Formula I}$$

wherein

Xaa is any D- or L-amino acid residue having the formula —NR$^N$—CR$^1$R$^2$—(C=O)—, or a peptide of n=2-20 amino acid residues having the formula —{NR$^N$—CR$^1$R$^2$—(C=O)}$_n$—, wherein R$^1$ is independently, for each occurrence, a non-hydrogen, substituted or unsubstituted side chain of an amino acid;

R$^2$ is independently, for each occurrence, hydrogen, or an organic group consisting of carbon, oxygen, nitrogen, sulfur, and hydrogen atoms, and having from 1 to 20 carbon atoms, or C(1-5)alkyl, cycloalkyl, cycloalkylalkyl, C(3-5)alkenyl, C(3-5)alkynyl, C(1-5)alkanoyl, C(1-5)alkanoyloxy, C(1-5)alkoxy, C(1-5)alkoxy-C(1-5)alkyl, C(1-5)alkoxy-C(1-5)alkoxy, C(1-5)alkyl-amino-C(1-5)alkyl-, C(1-5)dialkyl-amino-C(1-5)alkyl-, nitro-C(1-5)alkyl, cyano-C(1-5)alkyl, aryl-C(1-5)alkyl, 4-biphenyl-C(1-5)alkyl, carboxyl, or hydroxyl, R$^N$ is independently, for each occurrence, hydrogen, or an organic group consisting of carbon, oxygen, nitrogen, sulfur, and hydrogen atoms, and having from 1 to 20 carbon atoms, or C(1-5)alkyl, cycloalkyl, cycloalkylalkyl, C(3-5)alkenyl, C(3-5)alkynyl, C(1-5)alkanoyl, C(1-5)alkanoyloxy, C(1-5)alkoxy, C(1-5)alkoxy-C(1-5)alkyl, C(1-5)alkoxy-C(1-5)alkoxy, C(1-5)alkyl-amino-C(1-5)alkyl-, C(1-5)dialkyl-amino-C(1-5)alkyl-, nitro-C(1-5)alkyl, cyano-C(1-5)alkyl, aryl-C(1-5)alkyl, 4-biphenyl-C(1-5)alkyl, carboxyl, or hydroxyl, R$^3$ is a lipophilic tail derived from a naturally-occurring or synthetic phospholipid, glycolipid, triacylglycerol, glycerophospholipid, sphingolipid, ceramide, sphingomyelin, cerebroside, or ganglioside; or a substituted or unsubstituted C(3-22)alkyl, C(6-12)cycloalkyl, C(6-12)cycloalkyl-C(3-22)alkyl, C(3-22)alkenyl, C(3-22)alkynyl, C(3-22)alkoxy, or C(6-12)alkoxy-C(3-22)alkyl; or a lipophilic tail of any other naturally-occurring or synthetic lipid, or a lipophilic tail of any one of the additional delivery lipids described hereinbelow, and may contain a steroid;

R$^4$ is a lipophilic tail derived from a naturally-occurring or synthetic phospholipid, glycolipid, triacylglycerol, glycerophospholipid, sphingolipid, ceramide, sphingomyelin, cerebroside, or ganglioside; or a substituted or unsubstituted C(3-22)alkyl, C(6-12)cycloalkyl, C(6-12)cycloalkyl-C(3-22)alkyl, C(3-22)alkenyl, C(3-22)

alkynyl, C(3-22)alkoxy, or C(6-12)alkoxy-C(3-22) alkyl; or a lipophilic tail of any other naturally-occurring or synthetic lipid, or a lipophilic tail of any one of the additional delivery lipids described herein-below, and may contain a steroid;

Z is NH, O, S, —$CH_2S$—, —$CH_2S(O)$—, or an organic linker consisting of 1-40 atoms selected from hydrogen, carbon, oxygen, nitrogen, and sulfur atoms;

and salts thereof.

In some embodiments, $R^3$ is independently a substituted or unsubstituted C(6-22)alkyl or C(6-22)alkenyl; $R^4$ is independently a substituted or unsubstituted C(6-22)alkyl or C(6-22)alkenyl.

The residue Xaa may be a D- or L-stereocenter.

In some embodiments, the amino acid core may be a peptide of 2-20 amino acid residues having lipophilic tails at the N-terminus and C-terminus of the peptide.

In some embodiments, $R^1$ is a non-hydrogen, substituted or unsubstituted side chain of an amino acid wherein a substituent of a side chain is an organic group consisting of 1 to 40 atoms selected from hydrogen, carbon, oxygen, nitrogen, and sulfur atoms.

In some embodiments, Z is an alkyl or an organic linker synthetic polymer such as a polyethylene glycol chain (PEG), or a PEG copolymer such as PEG-polyurethane or PEG-polypropylene. See, e.g., J. Milton Harris, Poly(ethylene glycol) chemistry: biotechnical and biomedical applications (1992).

In some embodiments, this invention provides a range of amino acid lipids as shown in Formula I above wherein:
  Xaa is any D- or L-amino acid having the general formula —$NR^N$—$CR^1R^2$—(C=O)—, wherein
    $R^1$ is a non-hydrogen, substituted or unsubstituted basic side chain of an amino acid;
    $R^2$ is hydrogen, or C(1-5)alkyl,
    $R^N$ is hydrogen, or C(1-5)alkyl,
  $R^3$ is a lipophilic tail derived from a naturally-occurring or synthetic phospholipid, glycolipid, triacylglycerol, glycerophospholipid, sphingolipid, ceramide, sphingomyelin, cerebroside, or ganglioside; or a substituted or unsubstituted C(3-22)alkyl, C(6-12)cycloalkyl, C(6-12)cycloalkyl-C(3-22)alkyl, C(3-22)alkenyl, C(3-22)alkynyl, C(3-22)alkoxy, or C(6-12)alkoxy-C(3-22)alkyl; or a lipophilic tail of any other naturally-occurring or synthetic lipid, or a lipophilic tail of any one of the additional delivery lipids described herein-below, and may contain a steroid;
  $R^4$ is a lipophilic tail derived from a naturally-occurring or synthetic phospholipid, glycolipid, triacylglycerol, glycerophospholipid, sphingolipid, ceramide, sphingomyelin, cerebroside, or ganglioside; or substituted or unsubstituted C(3-22)alkyl, C(6-12)cycloalkyl, C(6-12)cycloalkyl-C(3-22)alkyl, C(3-22)alkenyl, C(3-22)alkynyl, C(3-22)alkoxy, or C(6-12)alkoxy-C(3-22)alkyl; or a lipophilic tail of any other naturally-occurring or synthetic lipid, or a lipophilic tail of any one of the additional delivery lipids described herein-below, and may contain a steroid;
  Z is NH, O, S, —$CH_2S$—, —$CH_2S(O)$—, or an organic linker consisting of 1-40 atoms selected from hydrogen, carbon, oxygen, nitrogen, and sulfur atoms.

In some embodiments, this invention provides a range of amino acid lipids as shown in Formula I above wherein:
  Xaa is any D- or L-amino acid having the general formula —$NR^N$—$CR^1R^2$—(C=O)—, wherein
    $R^1$ is a non-hydrogen, substituted or unsubstituted basic side chain of an amino acid;
    $R^2$ is hydrogen, or C(1-5)alkyl,
    $R^N$ is hydrogen, or C(1-5)alkyl,
  $R^3$ is a substituted or unsubstituted C(3-22)alkyl, C(6-12)cycloalkyl, C(6-12)cycloalkyl-C(3-22)alkyl, C(3-22)alkenyl, C(3-22)alkynyl, C(3-22)alkoxy, or C(6-12)alkoxy-C(3-22)alkyl;
  $R^4$ is a substituted or unsubstituted C(3-22)alkyl, C(6-12)cycloalkyl, C(6-12)cycloalkyl-C(3-22)alkyl, C(3-22)alkenyl, C(3-22)alkynyl, C(3-22)alkoxy, or C(6-12)alkoxy-C(3-22)alkyl;
  Z is NH, O, S, —$CH_2S$—, —$CH_2S(O)$—, or an organic linker consisting of 1-40 atoms selected from hydrogen, carbon, oxygen, nitrogen, and sulfur atoms.

In some embodiments, this invention provides a range of amino acid lipids as shown in Formula I above wherein:
  Xaa is any D- or L-amino acid having the general formula —$NR^N$—$CR^1R^2$—(C=O)—, wherein
    $R^1$ is a non-hydrogen, substituted or unsubstituted basic side chain of an amino acid;
    $R^2$ is hydrogen, or C(1-5)alkyl,
    $R^N$ is hydrogen, or C(1-5)alkyl,
  $R^3$ is a substituted or unsubstituted C(3-22)alkyl, C(6-12)cycloalkyl, C(6-12)cycloalkyl-C(3-22)alkyl, C(3-22)alkenyl, C(3-22)alkynyl, C(3-22)alkoxy, or C(6-12)alkoxy-C(3-22)alkyl;
  $R^4$ is a substituted or unsubstituted C(3-22)alkyl, C(6-12)cycloalkyl, C(6-12)cycloalkyl-C(3-22)alkyl, C(3-22)alkenyl, C(3-22)alkynyl, C(3-22)alkoxy, or C(6-12)alkoxy-C(3-22)alkyl;
  Z is NH.

In some embodiments, this invention provides a range of amino acid lipids as shown in Formula I above wherein:
  Xaa is any D- or L-amino acid having the general formula —$NR^N$—$CR^1R^2$—(C=O)—, wherein
    $R^1$ is a non-hydrogen, substituted or unsubstituted basic side chain of an amino acid;
    $R^2$ is hydrogen, or C(1-5)alkyl,
    $R^N$ is hydrogen, or C(1-5)alkyl,
  $R^3$ is a substituted or unsubstituted C(3-22)alkyl, C(6-12)cycloalkyl, C(6-12)cycloalkyl-C(3-22)alkyl, C(3-22)alkenyl, C(3-22)alkynyl, C(3-22)alkoxy, or C(6-12)alkoxy-C(3-22)alkyl;
  $R^4$ is a substituted or unsubstituted C(3-22)alkyl, C(6-12)cycloalkyl, C(6-12)cycloalkyl-C(3-22)alkyl, C(3-22)alkenyl, C(3-22)alkynyl, C(3-22)alkoxy, or C(6-12)alkoxy-C(3-22)alkyl;
  Z is O.

Cationic amino acid lipids can be prepared where, for example, Xaa has a basic side chain. Examples of amino acids having a basic side chain include arginine (Arg), homoarginine (homoArg) (side chain —$(CH_2)_4NH(C=NH)NH_2$), norarginine (norArg) (side chain —$(CH_2)_2NH(C=NH)NH_2$), nor-norarginine (nornorArg) (side chain —$(CH_2)NH(C=NH)NH_2$), ornithine, lysine, homolysine, histidine, 1-methylhistidine, pyridylalanine (Pal), asparagine, N-ethylasparagine, glutamine, and 4-aminophenylalanine, and side chain modified derivatives thereof.

As used herein, the term "homo," when referring to an amino acid, means that an additional carbon is added to the side chain, while the term "nor," when referring to an amino acid, means that a carbon is subtracted from the side chain. Thus, homolysine refers to side chain —$(CH_2)_5NH_2$.

Anionic amino acid lipids can be prepared where, for example, Xaa is glutamate or aspartate.

Cationic and anionic amino acid lipids can also be prepared where the amino acid side chain contains an ionizable group or substituent.

Non-cationic amino acid lipids can be prepared where, for example, Xaa is leucine, valine, alanine, or serine.

In some embodiments, Xaa is $N^G$-methylarginine, symmetric or asymmetric $N^G,N^G$-dimethylarginine, $N^G$-methyl-homoarginine, symmetric or asymmetric $N^G,N^G$-dimethyl-homoarginine, $N^G$-methyl-norarginine, symmetric or asymmetric $N^G,N^G$-dimethyl-norarginine, or $N^G$-methyl-nor-norarginine, symmetric or asymmetric $N^G,N^G$-dimethyl-nor-norarginine.

In some embodiments, Xaa is $N^G$-ethylarginine, symmetric or asymmetric $N^G,N^G$-diethylarginine, $N^G$-ethyl-homoarginine, symmetric or asymmetric $N^G,N^G$-diethyl-homoarginine, $N^G$-ethyl-norarginine, symmetric or asymmetric $N^G,N^G$-diethyl-norarginine, or $N^G$-ethyl-nor-norarginine, symmetric or asymmetric $N^G,N^G$-diethyl-nor-norarginine.

In certain embodiments, Xaa is $N^G$-alkylarginine, symmetric or asymmetric $N^G,N^G$-dialkylarginine, $N^G$-alkyl-homoarginine, symmetric or asymmetric $N^G,N^G$-dialkyl-homoarginine, $N^G$-alkyl-norarginine, symmetric or asymmetric $N^G,N^G$-dialkyl-norarginine, or $N^G$-alkyl-nor-norarginine, symmetric or asymmetric $N^G,N^G$-dialkyl-nor-norarginine.

In some embodiments, Xaa is an amino acid having a guanidine- or amidine-containing side chain. For example, the side chain of the Xaa residue may contain a group such as guanido, amidino, dihydroimidazole, 4-guanido-phenyl, 4-amidino-phenyl, N-amidino-piperidine, N-amidino-piperazine, 4,5-dihydroimidazole, 2-(N-amidino)-pyrrolidinyl, or 4-[(2-aminopyrimidinyl)]ethyl.

Examples of Xaa side chains include the following structures, as well as their salt forms:

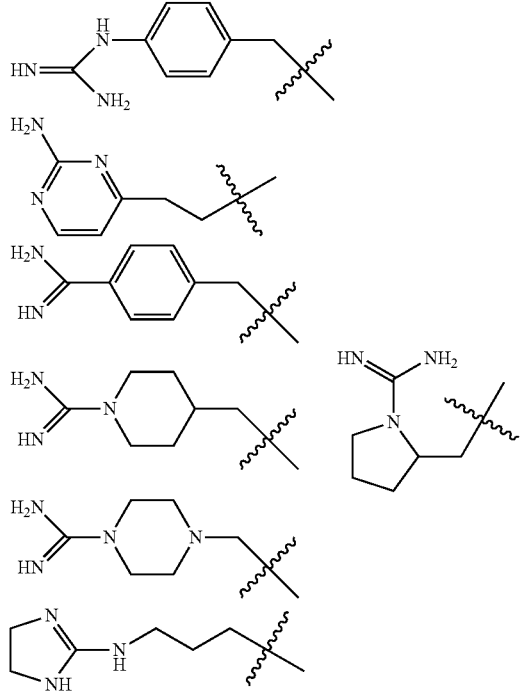

Examples of a substituted side chain of an amino acid suitable for a releasable form of an amino acid lipid include a releasing functional group having a pKa from about 5 to about 7.5, or from about 6 to about 7. In general, a releasing functional group which is a weak base may exhibit a predominant neutral form at a local pH above pKa, and may exhibit a predominant ionic form at a local pH below pKa. A releasing functional group which is a weak acid may exhibit an ionic form at a local pH above pKa, and may exhibit a neutral form at a local pH below pKa. See, e.g., P. Heinrich Stahl, Handbook of Pharmaceutical Salts, (2002).

In some embodiments, Xaa may have a side chain containing a functional group having a pKa from 5 to 7.5.

Examples of a substituted side chain of an amino acid suitable for a releasable form of an amino acid lipid include 1-methylhistidine.

Examples of a substituted side chain of an amino acid suitable for a releasable form of an amino acid lipid include 3,5-diiodo-tyrosine.

Examples of a substituted side chain of an amino acid suitable for a releasable form of an amino acid lipid include the following structures:

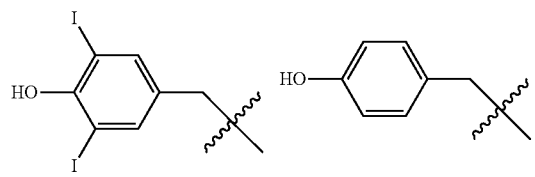 [SMILES: *Cc1cc(I)c(O)c(I)c1 ; *Cc1ccc(O)cc1]

Examples of amino acid lipids include the structures:

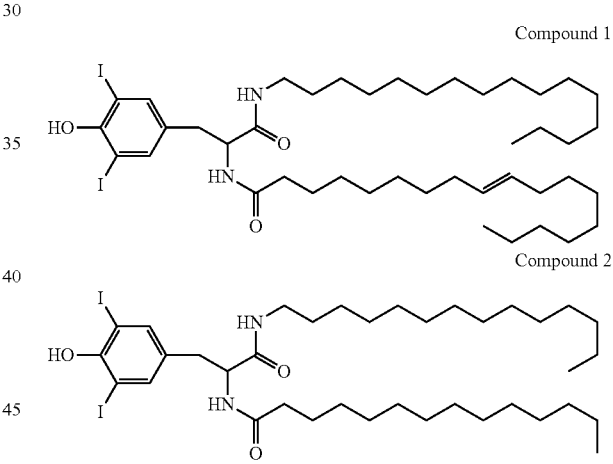

Compound 1

Compound 2

Examples of a substituent on a side chain of an amino acid suitable for a releasable form of an amino acid lipid include releasing functional groups derived from 3,5-diiodo-tyrosine, 1-methylhistidine, 2-methylbutanoic acid, 2-o-anisylpropanoic acid, meso-tartaric acid, 4,6-dimethylpyrimidinamine, p-phthalic acid, creatinine, butanoic acid, N,N-dimethyl-1-naphthylamine, pentanoic acid, 4-methylpentanoic acid, N-methylaniline, 1,10-phenanthroline, 3-pyridinecarboxylic acid, hexanoic acid, propanoic acid, 4-aminobenzoic acid, 2-methylpropanoic acid, heptanoic acid, octanoic acid, cyclohexanecarboxylic acid, quinoline, 3-quinolinamine, 2-aminobenzoic acid, 4-pyridinecarboxylic acid, nonanic acid, melamine, 8-quinolinol, trimethylacetic acid, 6-methoxyquinoline, 4-(methylamino)benzoic acid, p-methylaniline, 3-(methylamino)benzoic acid, malic acid, N-ethylaniline, 2-benzylpyridine, 3,6-dinitrophenol, N,N-dimethylaniline, 2,5-dimethylpiperazine, p-phenetidine, 5-methylquinoline, 2-phenylbenzimidazole, pyridine, picolinic acid, 3,5-diiodityrosine, p-anisidine, 2-(methylamino)benzoic acid, 2-thiazolamine, glutaric acid, adipic acid, isoquinoline, itaconic acid, o-phthalic acid, benzimidazole, piperazine, heptanedioic acid, acridine, phenanthridine, succinic acid, methylsuccinic acid, 4-methylquinoline, 3-methylpyridine, 7-isoquinolinol, malonic acid, methymalonic acid, 2-methylquinoline, 2-ethylpyridine, 2-methylpyridine, 4-methylpyridine, histamine, histidine, maleic acid, cis-1,2-cyclohexanediamine, 3,5-dimethylpyridine, 2-ethylbenzimidazole, 2-methylbenzimidazole, cacodylic acid, perimidine, citric acid, isocitric acid, 2,5-dimethylpyridine, papaverine, 6-hydroxy-4-methylpteridine, L-thyroxine, 3,4-dimethylpyridine, methoxypyridine, trans-1,2-cyclohexanediamine, 2,5-pyridinediamine, 1-1-methylhistidine, 1-3-methylhistidine, 2,3-dimethylpyridine, xanthopterin, 1,2-propanediamine, N,N-diethylaniline, alloxanic acid, 2,6-dimethylpyridine, L-carnosine, 2-pyridinamine, N-b-alanylhistidine, pilocarpine, 1-methylimidazol, 1H-imidazole, 2,4-dimethylpyridine, 4-nitrophenol, 2-nitrophenol, tyrosineamide, 5-hydoxxyquinazoline, 1,1-cyclopropanedicarboxylic acid, 2,4,6-trimethylpyridine, veronal, 2,3-dichlorophenol, 1,2-ethanediamine, 1-isoquinolinamine, and combinations thereof.

In some embodiments, a range of amino acid lipids corresponding to Formula I are represented by the structures

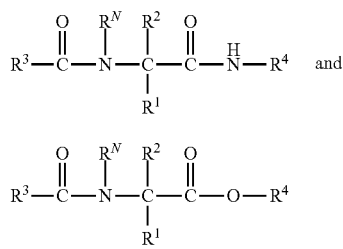

Structure 1A

Structure 1B where $R^1$, $R^2$, $R^N$, $R^3$, and $R^4$ are defined as above.

In some embodiments, $R^3$ and $R^4$ are independently selected lipid-like tails which impart sufficient lipophilic character or lipophilicity, such as defined by water/octanol partitioning, to provide delivery across a membrane or uptake by a cell. These tails provide, when used in an amino acid lipid structure, an amphipathic molecule. Lipid-like tails may be derived from phospholipids, glycolipids, triacylglycerols, glycerophospholipids, sphingolipids, ceramides, sphingomyelins, cerebrosides, or gangliosides, among others, and may contain a steroid.

In certain embodiments, $R^3$ and $R^4$ may independently be a lipid-like tail having a glycerol backbone.

In some embodiments, $R^3$ and $R^4$ may independently be C3alkyl, C4alkyl, C5alkyl, C6alkyl, C7alkyl, C8alkyl, C9alkyl, C10alkyl, C11alkyl, C12alkyl, C13alkyl, C14alkyl, C15alkyl, C16alkyl, C17alkyl, C18alkyl, C19alkyl, C20alkyl, C21alkyl, or C22alkyl.

In some embodiments, $R^3$ and $R^4$ may independently be lipophilic tails having one of the following structures:

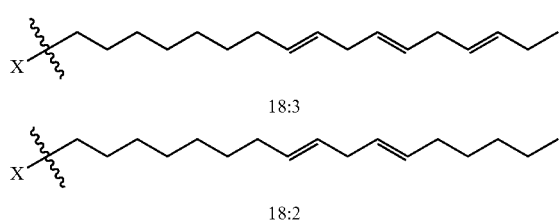

18:3

18:2

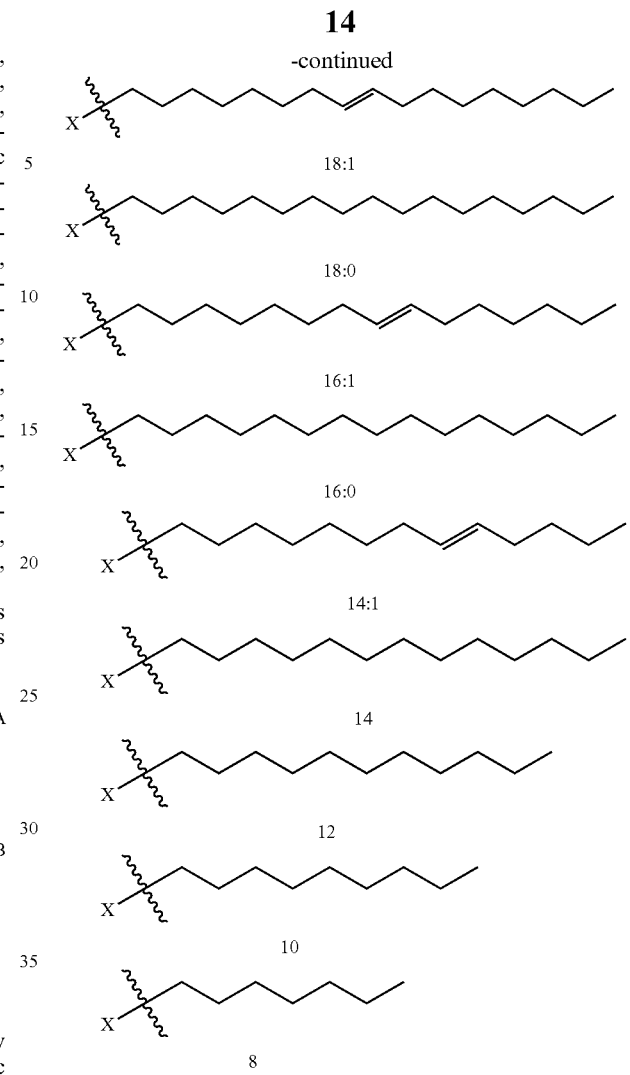

18:1

18:0

16:1

16:0

14:1

14

12

10

8

In the structures above, X represents the atom of the tail that is directly attached to the amino acid residue terminus, and is counted as one of the atoms in the numerical designation, for example, "18:3." In some embodiments, X may be a carbon, nitrogen, or oxygen atom.

In some embodiments, $R^3$ and $R^4$ may independently be lipophilic tails having one of the following structures:

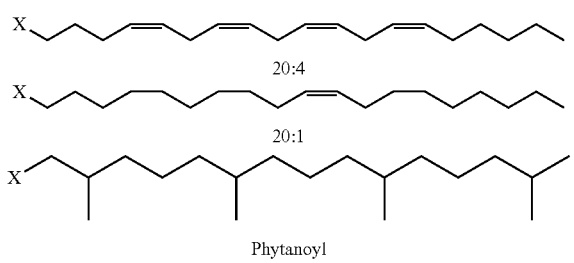

20:4

20:1

Phytanoyl where X is as defined above.

In some embodiments, $R^3$ and $R^4$ are independently selected lipid-like tails which may contain a cholesterol, a sterol, or a steroid such as gonanes, estranes, androstanes, pregnanes, cholanes, cholestanes, ergostanes, campestanes, poriferastanes, stigmastanes, gorgostanes, lanostanes, cycloartanes, as well as sterol or zoosterol derivatives of any of the foregoing, and their biological intermediates and precursors, which may include, for example, cholesterol, lanosterol, stigmastanol, dihydrolanosterol, zymosterol, zymostenol, desmosterol, 7-dehydrocholesterol, and mixtures and derivatives thereof.

In certain embodiments, $R^3$ and $R^4$ may independently be derived from fatty acid-like tails such as tails from myristic acid (C14:0)alkenyl, palmitic acid (C16:0)alkenyl, stearic acid (C18:0)alkenyl, oleic acid (C18:1, double bond at carbon 9)alkenyl, linoleic acid (C18:2, double bond at carbon 9 or 12)alkenyl, linonenic acid (C18:3, double bond at carbon 9, 12, or 15)alkenyl, arachidonic acid (C20:4, double bond at carbon 5, 8, 11, or 14)alkenyl, and eicosapentaenoic acid (C20:5, double bond at carbon 5, 8, 11, 14, or 17)alkenyl. Other examples of fatty acid-like tails are found at Donald Voet and Judith Voet, *Biochemistry*, 3rd Edition (2005), p. 383.

In some embodiments, $R^3$ and $R^4$ may independently be derived from an isoprenoid.

As used herein, the term "amino acid" includes naturally-occurring and non-naturally occurring amino acids. Thus, an amino acid lipid of this invention can be made from a genetically encoded amino acid, a naturally occurring non-genetically encoded amino acid, or a synthetic amino acid.

Examples of amino acids include Ala, Arg, Asn, Asp, Cys, Gln, Glu, Gly, His, Ile, Leu, Lys, Met, Phe, Pro, Ser, Thr, Trp, Tyr, and Val.

Examples of amino acids include azetidine, 2-aminooctadecanoic acid, 2-aminoadipic acid, 3-aminoadipic acid, 2,3-diaminopropionic acid, 2-aminobutyric acid, 4-aminobutyric acid, 2,3-diaminobutyric acid, 2,4-diaminobutyric acid, 2-aminoisobutyric acid, 4-aminoisobutyric acid, 2-aminopimelic acid, 2,2'-diaminopimelic acid, 6-aminohexanoic acid, 6-aminocaproic acid, 2-aminoheptanoic acid, desmosine, ornithine, citrulline, N-methylisoleucine, norleucine, tert-leucine, phenylglycine, t-butylglycine, N-methylglycine, sacrosine, N-ethylglycine, cyclohexylglycine, 4-oxo-cyclohexylglycine, N-ethylasparagine, cyclohexylalanine, t-butylalanine, naphthylalanine, pyridylalanine, 3-chloroalanine, 3-benzothienylalanine, 4-halophenylalanine, 4-chlorophenylalanine, 2-fluorophenylalanine, 3-fluorophenylalanine, 4-fluorophenylalanine, penicillamine, 2-thienylalanine, methionine, methionine sulfoxide, homoarginine, norarginine, nor-norarginine, N-acetyllysine, 4-aminophenylalanine, N-methylvaline, homocysteine, homoserine, hydroxylysine, allo-hydroxylysine, 3-hydroxyproline, 4-hydroxyproline, isodesmosine, allo-isoleucine, 6-N-methyllysine, norvaline, O-allyl-serine, O-allyl-threonine, alpha-aminohexanoic acid, alpha-aminovaleric acid, pyroglutamic acid, and derivatives thereof.

As used herein, the term "amino acid" includes alpha- and beta-amino acids.

Examples of amino acid residues can be found in Fasman, *CRC Practical Handbook of Biochemistry and Molecular Biology*, CRC Press, Inc. (1989).

In general, a compound may contain one or more chiral centers. Compounds containing one or more chiral centers may include those described as an "isomer," a "stereoisomer," a "diastereomer," an "enantiomer," an "optical isomer," or as a "racemic mixture." Conventions for stereochemical nomenclature, for example the stereoisomer naming rules of Cahn, Ingold and Prelog, as well as methods for the determination of stereochemistry and the separation of stereoisomers are known in the art. See, for example, Michael B. Smith and Jerry March, *March's Advanced Organic Chemistry*, 5th edition, 2001. The compounds and structures of this disclosure are meant to encompass all possible isomers, stereoisomers, diastereomers, enantiomers, and/or optical isomers that would be understood to exist for the specified compound or structure, including any mixture, racemic or otherwise, thereof.

Examples of amino acid lipids include $R^3$—(C=O)-Arg-NH—$R^4$ wherein Arg is D- or L-arginine, and $R^3$ and $R^4$ are independently alkyl or alkenyl.

Examples of amino acid lipids include the following structures:

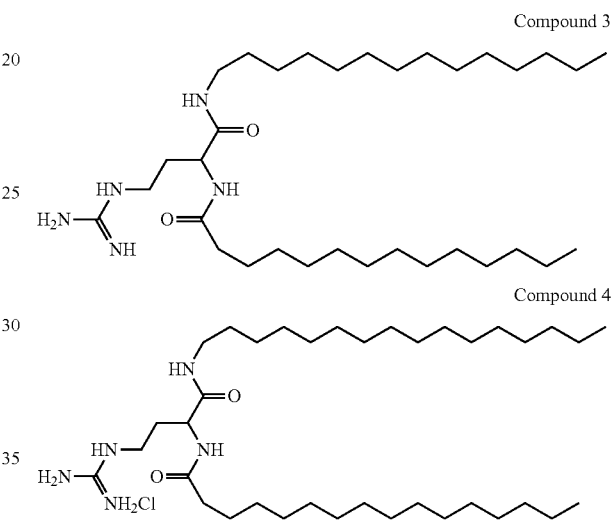

Compound 3

Compound 4

Examples of amino acid lipids include the following structures:

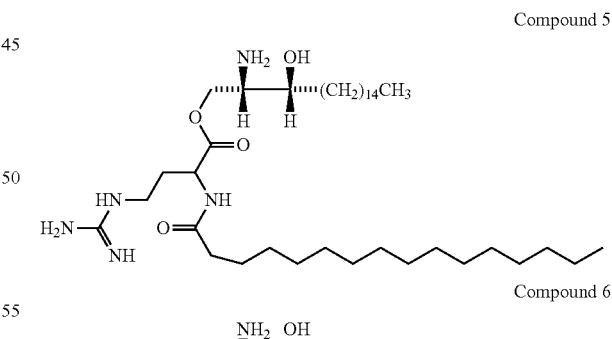

Compound 5

Compound 6

Examples of amino acid lipids include the following structures:

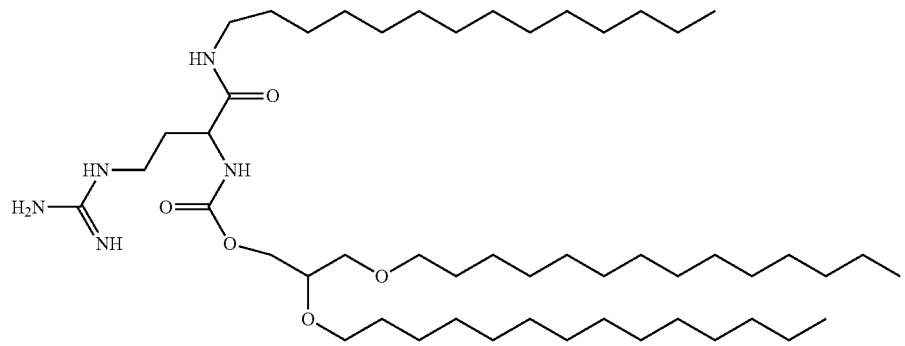
Compound 7
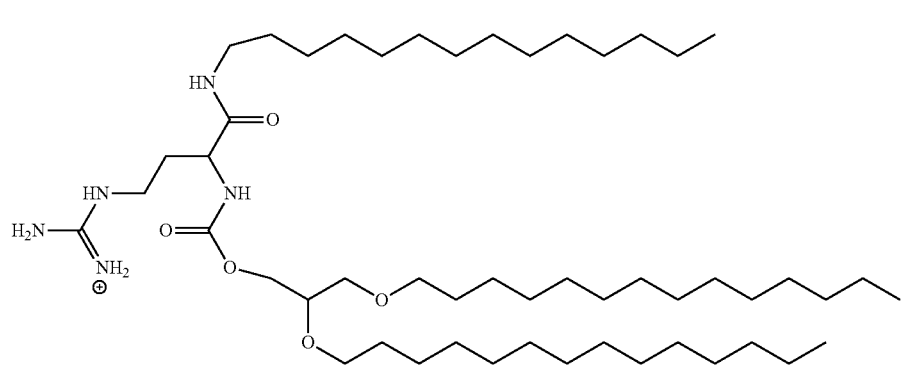
Compound 8
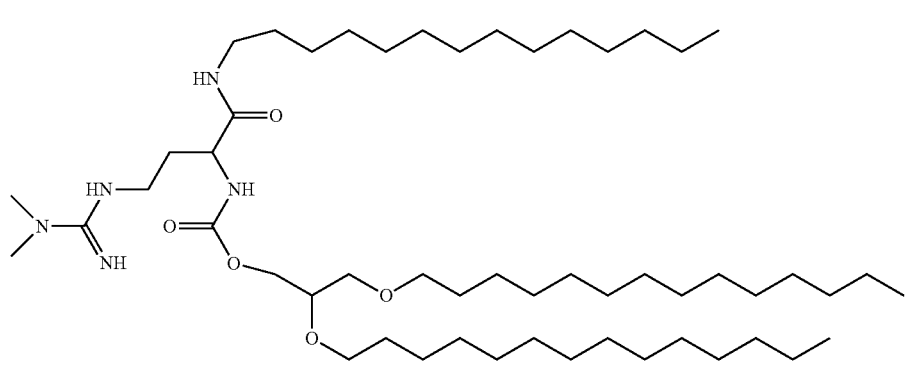
Compound 9
Examples of amino acid lipids include $R^3$—(C=O)-norArg-NH—$R^4$ wherein norArg is D- or L-norarginine, and $R^3$ and $R^4$ are independently alkyl or alkenyl.
Examples of amino acid lipids include the following structures:
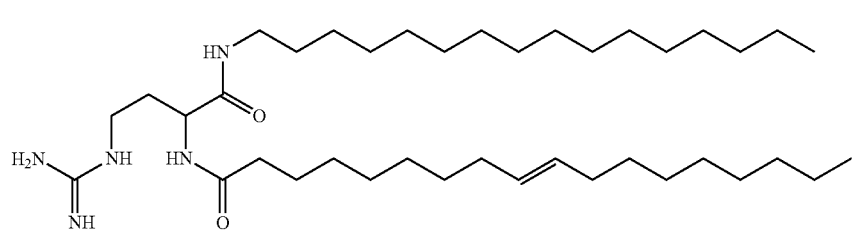
Compound 10

-continued
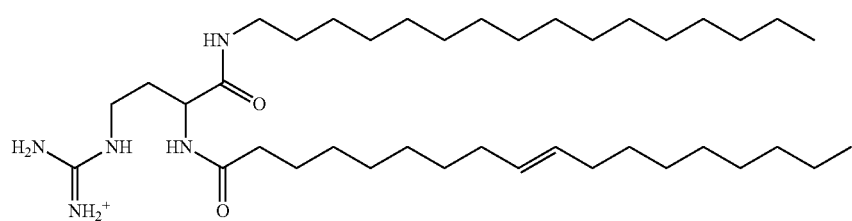
Compound 11
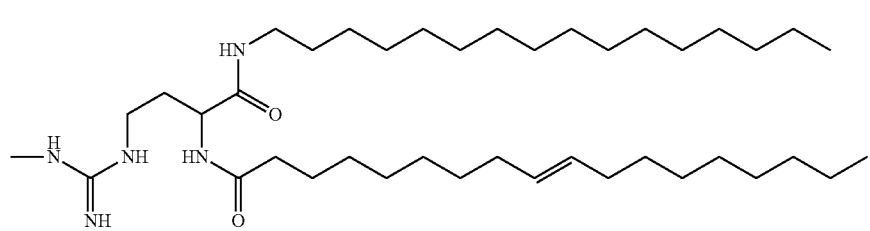
Compound 12
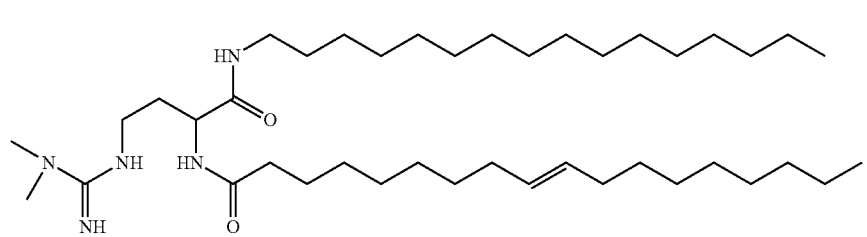
Compound 13
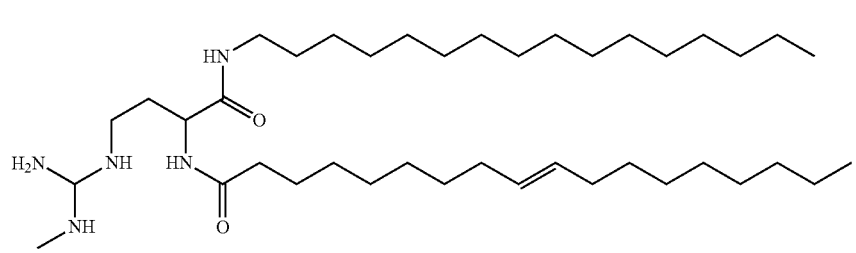
Compound 14
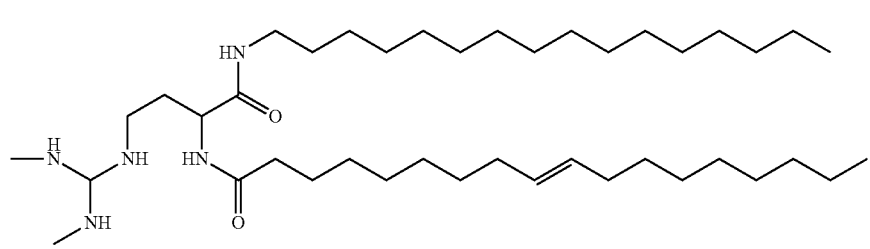
Compound 15
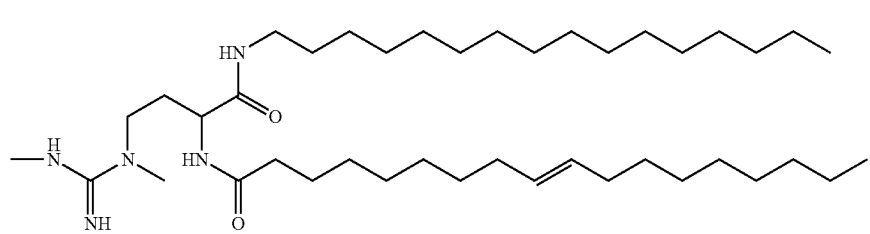
Compound 16
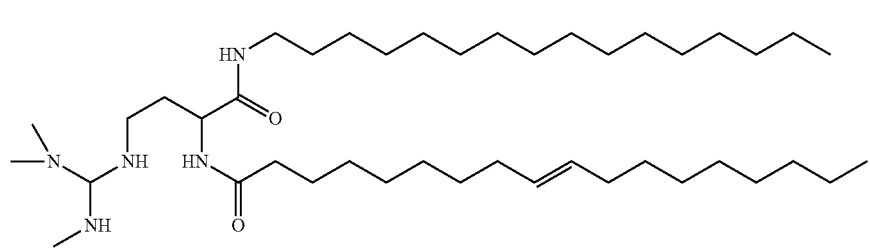
Compound 17

-continued

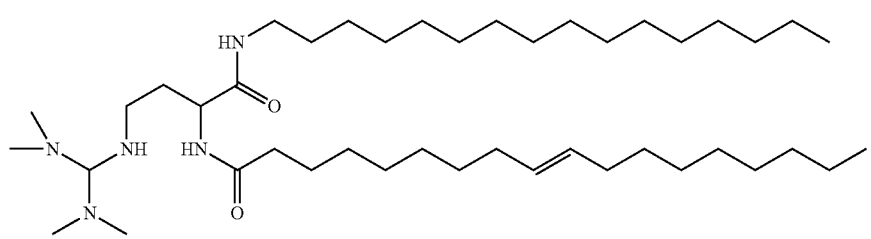
Compound 18

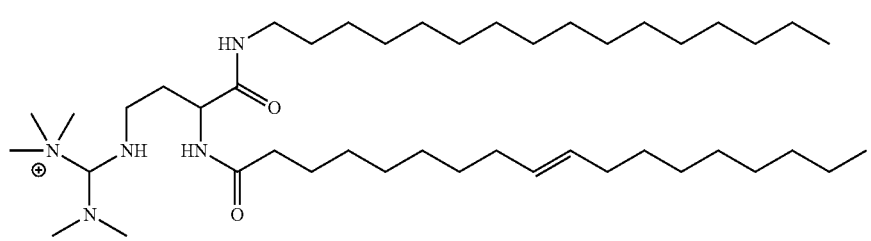
Compound 19

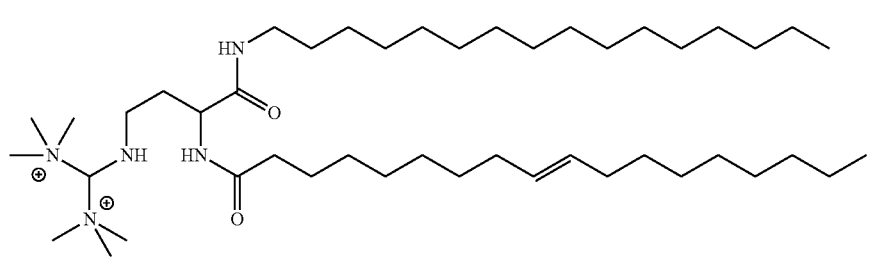
Compound 20

Examples of amino acid lipids include $R^3$—(C=O)-nornorArg-NH—$R^4$ wherein nornorArg is D- or L-nornorarginine, and $R^3$ and $R^4$ are independently alkyl such as heptyl, octyl, nonyl, decyl, and undecyl.

Examples of amino acid lipids include the following structures:

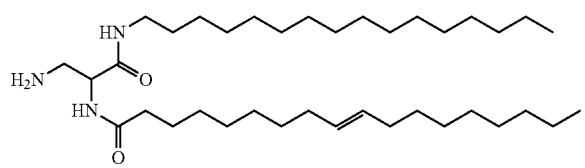
Compound 21

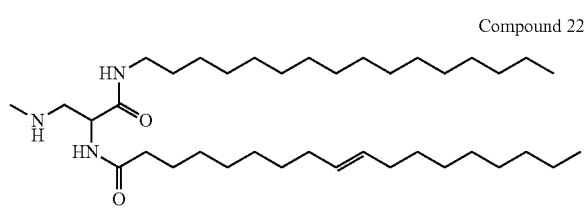
Compound 22

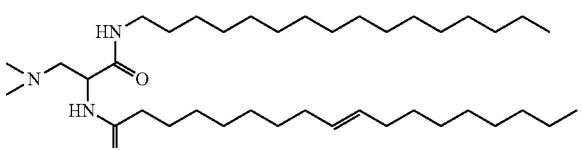
Compound 23

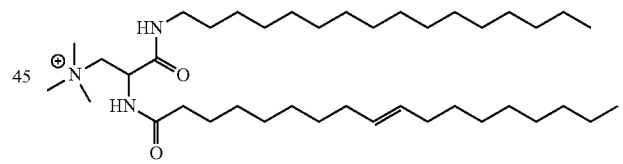
Compound 24

Examples of amino acid lipids include $R^3$—(C=O)-homoArg-NH—$R^4$ wherein homoArg is D- or L-homoarginine, and $R^3$ and $R^4$ are independently alkyl such as heptyl, octyl, nonyl, decyl, and undecyl.

Examples of amino acid lipids include $R^3$—(C=O)-4-pyridylalanine-NH—$R^4$ wherein the pyridylalanine is D- or L-pyridylalanine, and $R^3$ and $R^4$ are independently alkyl such as heptyl, octyl, nonyl, decyl, and undecyl. Examples of $R^3$—(C=O)-pyridylalanine-NH—$R^4$ amino acid lipids include pharmaceutically-acceptable pyridyl salts, such as 4-[N-methylpyridyl]alanine chloride. Examples of pyridylalanine amino acid lipids include the following structures:

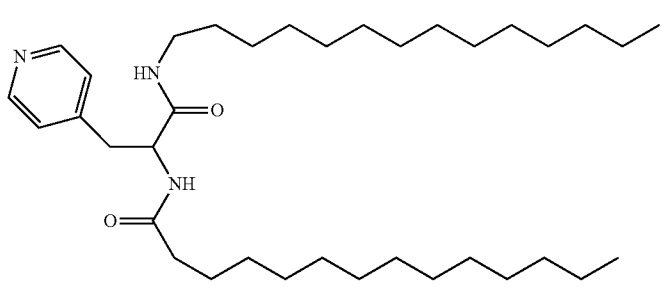
Compound 25
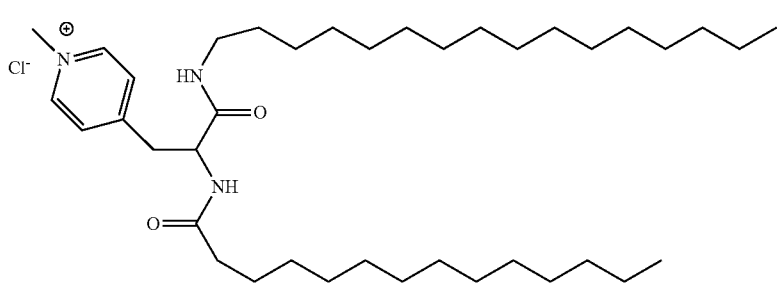
Compound 26
Examples of amino acid lipids include $R^3$—(C=O)-Lys-NH—$R^4$ wherein $R^3$ and $R^4$ are independently alkyl or alkenyl.
Examples of amino acid lipids include the following structures:
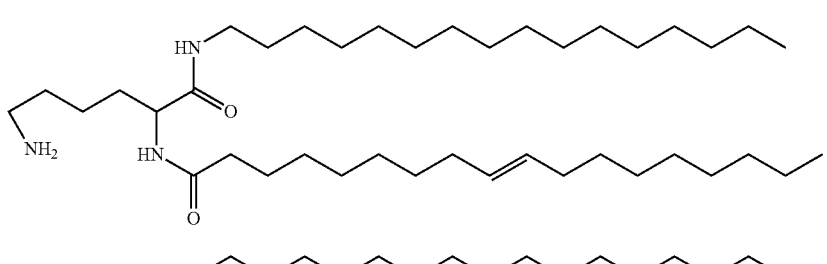
Compound 27
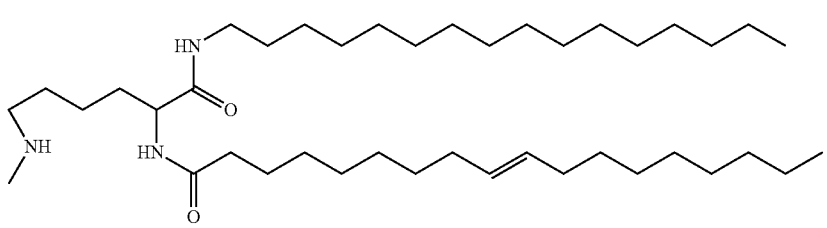
Compound 28
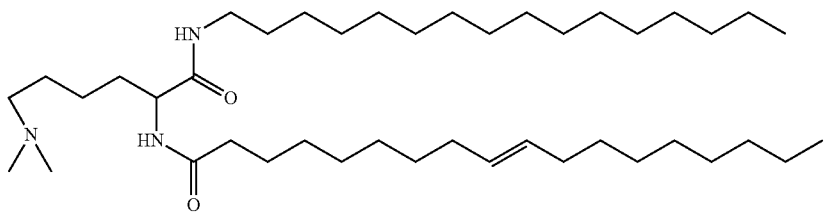
Compound 29
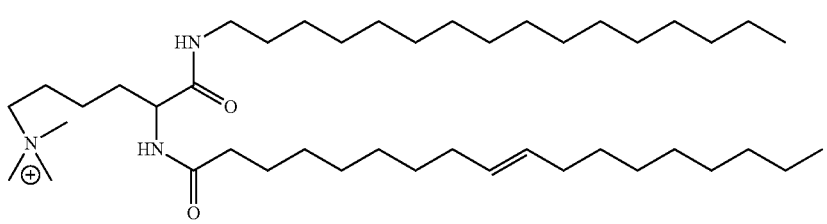
Compound 30

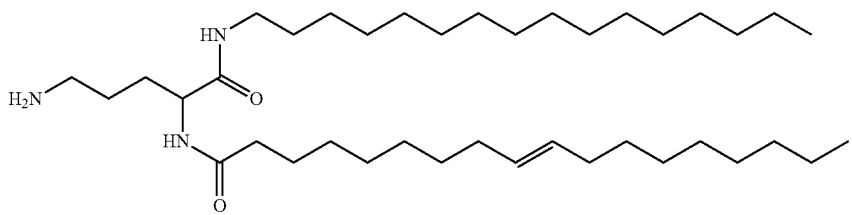
Compound 31
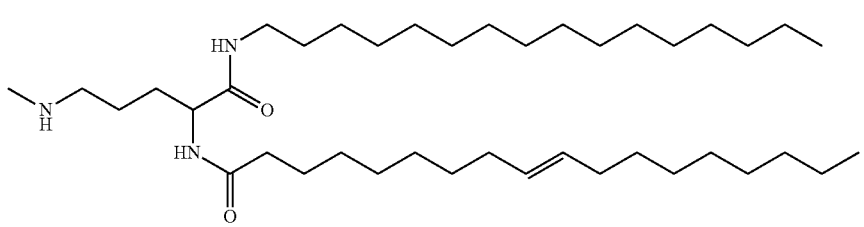
Compound 32
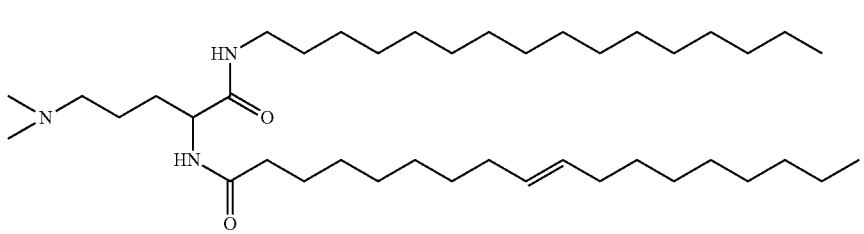
Compound 33
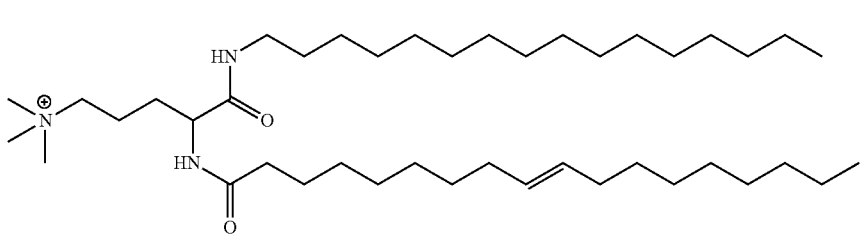
Compound 34
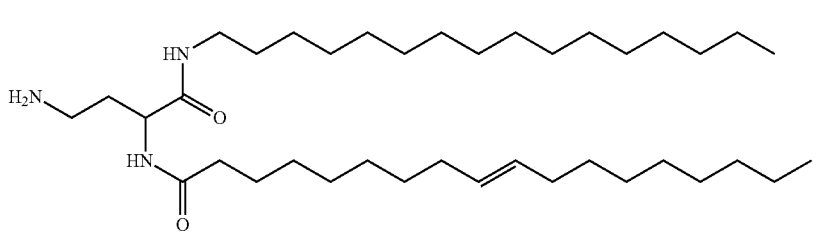
Compound 35
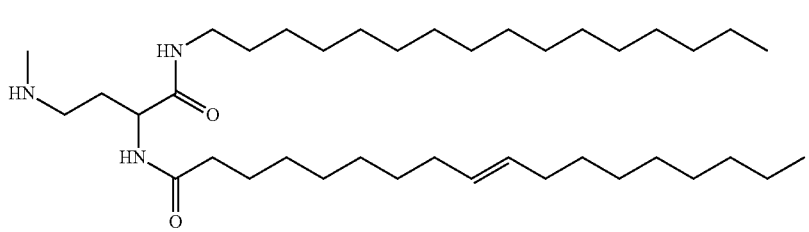
Compound 36
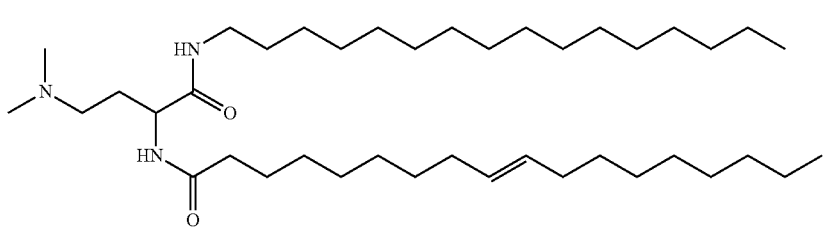
Compound 37

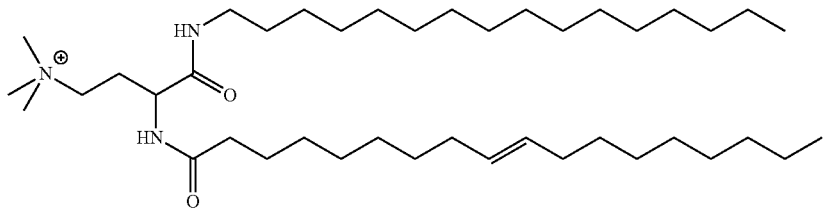

Compound 38

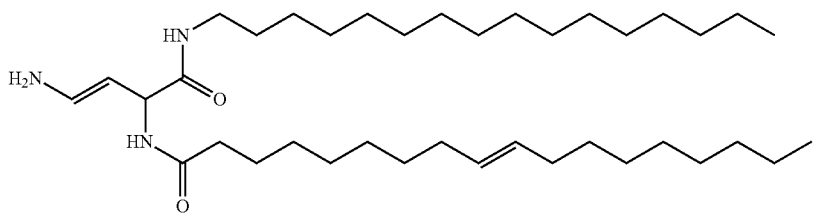

Compound 39

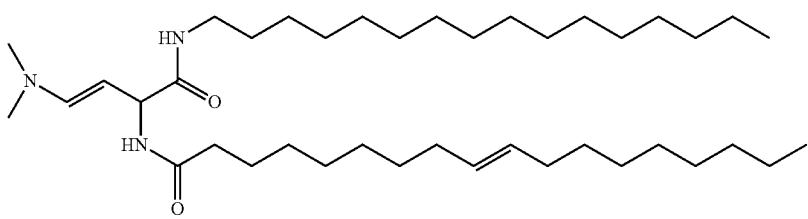

Compound 40

Examples of amino acid lipids include $R^3$—(C=O)-His-NH—$R^4$ wherein $R^3$ and $R^4$ are independently alkyl or alkenyl. Examples of His amino acid lipids include the following structures:

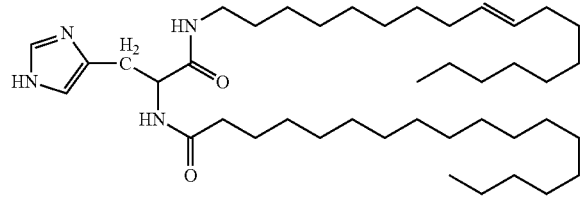

Compound 41

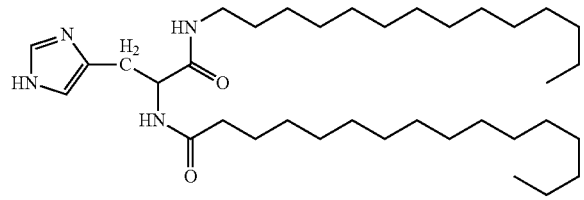

Compound 42

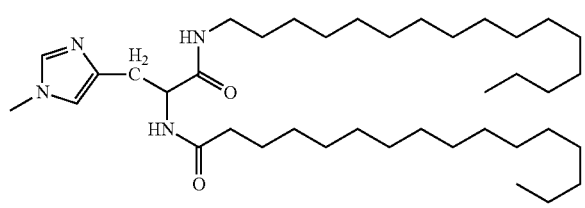

Compound 43

Examples of amino acid lipids include $R^3$—(C=O)-Xaa-O—$R^4$ wherein $R^3$ is alkyl and $R^4$ is a sphingoid. Examples of amino acid lipids include the following structures:

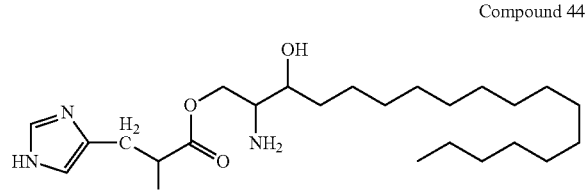

Compound 44

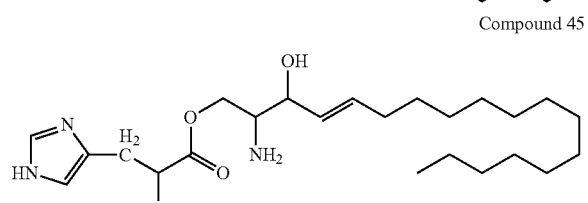

Compound 45

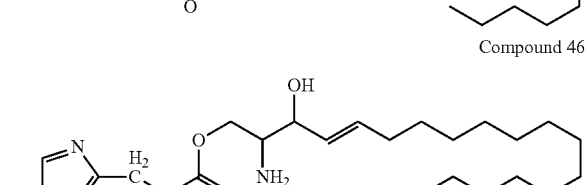

Compound 46

Examples of amino acid lipids include R³—(C=O)-Xaa-NH—R⁴ wherein R³ and R⁴ are alkyl or alkenyl. Examples of amino acid lipids include the following structure:

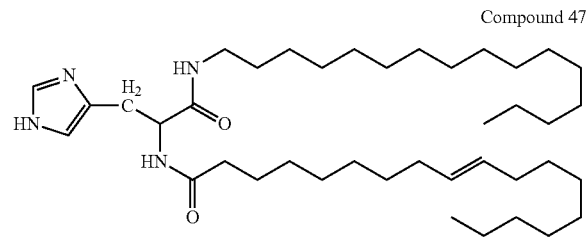 [SMILES: CCCCCCCC/C=C/CCCCCCCC(=O)NC(Cc1c[nH]cn1)C(=O)NCCCCCCCCCCCCCCCC]

Compound 47

Examples of amino acid lipids include (C10acyl)-Arg-NH—(C10alkyl), (C12acyl)-Arg-NH—(C12alkyl), (C14acyl)-Arg-NH—(C14alkyl), (C16acyl)-Arg-NH—(C16alkyl), (C18acyl)-Arg-NH—(C18alkyl), (C10acyl)-homoArg-NH—(C10alkyl), (C12acyl)-homoArg-NH—(C12alkyl), (C14acyl)-homoArg-NH—(C14alkyl), (C16acyl)-homoArg-NH—(C16alkyl), (C18acyl)-homoArg-NH—(C18alkyl), (C10acyl)-norArg-NH—(C10alkyl), (C12acyl)-norArg-NH—(C12alkyl), (C14acyl)-norArg-NH—(C14alkyl), (C16acyl)-norArg-NH—(C16alkyl), (C18acyl)-norArg-NH—(C18alkyl), (C10acyl)-nornorArg-NH—(C10alkyl), (C12acyl)-nornorArg-NH—(C12alkyl), (C14acyl)-nornorArg-NH—(C14alkyl), (C16acyl)-nornorArg-NH—(C16alkyl), (C18acyl)-nornor-Arg-NH—(C18alkyl), (C10acyl)-4-Pal-NH—(C10alkyl), (C12acyl)-4-Pal-NH—(C12alkyl), (C14acyl)-4-Pal-NH—(C14alkyl), (C16acyl)-4-Pal-NH—(C16alkyl), (C18acyl)-4-Pal-NH—(C18alkyl), (C10acyl)-4-Pal(Me)-NH—(C10alkyl), (C12acyl)-4-Pal(Me)-NH—(C12alkyl), (C14acyl)-4-Pal(Me)-NH—(C14alkyl), (C16acyl)-4-Pal(Me)-NH—(C16alkyl), and (C18acyl)-4-Pal(Me)-NH—(C18alkyl).

In general, the designation "C14-norArg-C14," for example, refers to (C13alkyl)-(C=O)-norArg-NH—(C14alkyl) which is the same as (C14acyl)-norArg-NH—(C14alkyl).

Examples of amino acid lipids include (C10acyl)-D-Arg-L-Arg-NH—(C10alkyl), (C12acyl)-D-Arg-L-Arg-NH—(C12alkyl), (C14acyl)-D-Arg-L-Arg-NH—(C14alkyl), (C16acyl)-D-Arg-L-Arg-NH—(C16alkyl), (C18acyl)-D-Arg-L-Arg-NH—(C18alkyl), (C10acyl)-D-homoArg-L-homoArg-NH—(C10alkyl), (C12acyl)-D-homoArg-L-homoArg-NH—(C12alkyl), (C14acyl)-D-homoArg-L-homoArg-NH—(C14alkyl), (C16acyl)-D-homoArg-L-homoArg-NH—(C16alkyl), (C18acyl)-D-homoArg-L-homoArg-NH—(C18alkyl), (C10acyl)-D-norArg-L-norArg-NH—(C10alkyl), (C12acyl)-D-norArg-L-norArg-NH—(C12alkyl), (C14acyl)-D-norArg-L-norArg-NH—(C14alkyl), (C16acyl)-D-norArg-L-norArg-NH—(C16alkyl), (C18acyl)-D-norArg-L-norArg-NH—(C18alkyl), (C10acyl)-D-nornorArg-L-nornorArg-NH—(C10alkyl), (C12acyl)-D-nornorArg-L-nornorArg-NH—(C12alkyl), (C14acyl)-D-nornorArg-L-nornorArg-NH—(C14alkyl), (C16acyl)-D-nornorArg-L-nornorArg-NH—(C16alkyl), (C18acyl)-D-nornorArg-L-nornorArg-NH—(C18alkyl).

Examples of amino acid lipids include (C10acyl)-His-Arg-NH—(C10alkyl), (C12acyl)-His-Arg-NH—(C12alkyl), (C14acyl)-His-Arg-NH—(C14alkyl), (C16acyl)-His-Arg-NH—(C16alkyl), (C18acyl)-His-Arg-NH—(C18alkyl), (C10acyl)-His-Arg-NH—(C10alkyl), (C12acyl)-His-Arg-NH—(C12alkyl), (C14acyl)-His-Arg-NH—(C14alkyl), (C16acyl)-His-Arg-NH—(C16alkyl), (C18acyl)-His-Arg-NH—(C18alkyl), (C10acyl)-His-Arg-(C10alkyl), (C12acyl)-His-Arg-NH—(C12alkyl), (C14acyl)-His-Arg-NH—(C14alkyl), (C16acyl)-His-Arg-NH—(C16alkyl), (C18acyl)-His-Arg-NH—(C18alkyl), (C10acyl)-His-Arg-NH—(C10alkyl), (C12acyl)-His-Arg-NH—(C12alkyl), (C14acyl)-His-Arg-NH—(C14alkyl), (C16acyl)-His-Arg-NH—(C16alkyl), (C18acyl)-His-Arg-NH—(C18alkyl).

Examples of amino acid lipids include (C10acyl)-His-Asp-NH—(C10alkyl), (C12acyl)-His-Asp-NH—(C12alkyl), (C14acyl)-His-Asp-NH—(C14alkyl), (C16acyl)-His-Asp-NH—(C16alkyl), (C18acyl)-His-Asp-NH—(C18alkyl), (C10acyl)-His-Asp-NH—(C10alkyl), (C12acyl)-His-Asp-NH—(C12alkyl), (C14acyl)-His-Asp-NH—(C14alkyl), (C16acyl)-His-Asp-NH—(C16alkyl), (C18acyl)-His-Asp-NH—(C18alkyl), (C10acyl)-His-Asp-NH—(C10alkyl), (C12acyl)-His-Asp-NH—(C12alkyl), (C14acyl)-His-Asp-NH—(C14alkyl), (C16acyl)-His-Asp-NH—(C16alkyl), (C18acyl)-His-Asp-NH—(C18alkyl), (C10acyl)-His-Asp-NH—(C10alkyl), (C12acyl)-His-Asp-NH—(C12alkyl), (C14acyl)-His-Asp-NH—(C14alkyl), (C16acyl)-His-Asp-NH—(C16alkyl), (C18acyl)-His-Asp-NH—(C18alkyl).

Examples of amino acid lipids include (C10acyl)-Pal-Arg-NH—(C10alkyl), (C12acyl)-Pal-Arg-NH—(C12alkyl), (C14acyl)-Pal-Arg-NH—(C14alkyl), (C16acyl)-Pal-Arg-NH—(C16alkyl), (C18acyl)-Pal-Arg-NH—(C18alkyl), (C10acyl)-Pal-Arg-NH—(C10alkyl), (C12acyl)-Pal-Arg-NH—(C12alkyl), (C14acyl)-Pal-Arg-NH—(C14alkyl), (C16acyl)-Pal-Arg-NH—(C16alkyl), (C18acyl)-Pal-Arg-NH—(C18alkyl), (C10acyl)-Pal-Arg-(C10alkyl), (C12acyl)-Pal-Arg-NH—(C12alkyl), (C14acyl)-Pal-Arg-NH—(C14alkyl), (C16acyl)-Pal-Arg-NH—(C16alkyl), (C18acyl)-Pal-Arg-NH—(C18alkyl), (C10acyl)-Pal-Arg-NH—(C10alkyl), (C12acyl)-Pal-Arg-NH—(C12alkyl), (C14acyl)-Pal-Arg-NH—(C14alkyl), (C16acyl)-Pal-Arg-NH—(C16alkyl), (C18acyl)-Pal-Arg-NH—(C18alkyl).

Amino acid lipids can be prepared as poly-mer or multi-mer species, such as dimers, trimers, or tetramers. The poly-mer or multi-mer species can be prepared from a single amino acid lipid, or from more than one species. Poly-mer or multi-mer amino acid lipids species can be prepared in some embodiments by providing a sulfhydryl group or other cross-linkable group on a side chain of the amino acid, or with linked or tethered amino acid structures such as desmosine or citrulline. In other embodiments, a poly-mer or multi-mer amino acid lipid species can be prepared with bioconjugate linker chemistries.

Examples of amino acid lipids include the following structures:

Compound 48

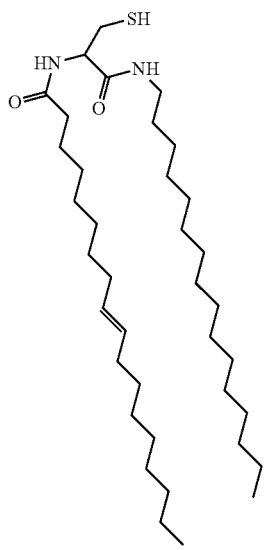

Compound 49

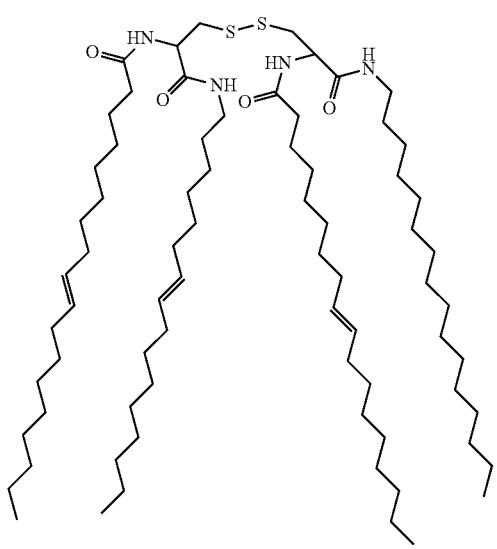

An amino acid lipid can be prepared as a conjugate having a peptide or polymer chain covalently attached to the amino acid side chain. The peptide or polymer chain can be attached using a reactive group of the amino acid side chain, for example, using the thiol or methylmercaptan group of cysteine or methionine, respectively, or the alcohol group of serine, or the amino group of lysine. The peptide or polymer chain can be attached using any reactive group of a substituted or modified amino acid side chain. Various linker groups such as NHS, maleimido, and bioconjugate techniques and linkers can be used.

Amino acid lipids can be prepared as constructs attached to an oligomeric or polymeric framework. For example, an amino acid lipid can be attached to polyethylene glycol, polypropylene glycol, an oligonucleotide network or lattice, a poly(amino acid), a carbohydrate, a dextran, a hydrogel, or a starch.

Amino acid lipids can be prepared as constructs attached to a pharmaceutical drug compound or composition, or a biologically active agent. For example, an amino acid lipid can be conjugated to a nucleic acid drug such as a regulatory or interfering RNA.

Examples of amino acid lipids include the following structures:

where R is any amino acid side chain.

The compounds and compositions of this disclosure may incorporate solubilizing or functionalizing groups or structures including polymeric structures. See, e.g., R. L. Dunn and R. M. Ottenbrite, Polymeric Drugs and Drug Delivery Systems, ACS Symp. Ser. 469 (1991). Amino acid lipids can be derivatized to enhance solubility such as, for example, to attach a diol, to prepare a quaternary ammonium or charged group, to attach hydroxyl or amine groups such as alcohols, polyols, or polyethers, or to attach a polyethyleneimine, a polyethyleneglycol or a polypropyleneglycol. The molecular mass of an attached polymeric component such as a polyethyleneglycol can be any value, for example, 200, 300, 400, 500, 600, 750, 1000, 1250, 1500, 2000, 3000, 4000, 5000, 7500, 10,000, 15,000, 20,000, 25,000, or 30,000 Da, or greater. For example, a polyethyleneglycol chain can be attached through an amino group or other reactive group of an amino acid side chain.

In general, as used herein, general chemical terms refer to all groups of a specified type, including groups having any number and type of atoms, unless otherwise specified. For example "alkenyl" refers broadly to alkyls having 2 to 22 carbon atoms, as defined below, while (C18:1)alkenyl refers to alkenyls having 18 carbon atoms and one double bond.

The term "alkyl" as used herein refers to a saturated, branched or unbranched, substituted or unsubstituted aliphatic group containing from 1-22 carbon atoms. This definition applies to the alkyl portion of other groups such as, for example, alkoxy, alkanoyl, aralkyl, and other groups defined below. The term "cycloalkyl" as used herein refers to a saturated, substituted or unsubstituted cyclic alkyl ring containing from 3 to 12 carbon atoms. As used herein, the term "C(1-5)alkyl," for example, includes C(1)alkyl, C(2)alkyl, C(3)alkyl, C(4)alkyl, and C(5)alkyl. Likewise, the term "C(3-22)alkyl," for example, includes C(1)alkyl, C(2)alkyl, C(3)alkyl, C(4)alkyl, C(5)alkyl, C(6)alkyl, C(7)alkyl, C(8)alkyl, C(9)alkyl, C(10)alkyl, C(11)alkyl, C(12)alkyl, C(13)alkyl, C(14)alkyl, C(15)alkyl, C(16)alkyl, C(17)alkyl, C(18)alkyl, C(19)alkyl, C(20)alkyl, C(21)alkyl, and C(22) alkyl.

The term "alkenyl" as used herein refers to an unsaturated, branched or unbranched, substituted or unsubstituted alkyl or cycloalkyl having 2 to 22 carbon atoms and at least one carbon-carbon double bond. The term "alkynyl" as used herein refers to an unsaturated, branched or unbranched, substituted or unsubstituted alkyl or cycloalkyl having 2 to 22 carbon atoms and at least one carbon-carbon triple bond.

The term "alkoxy" as used herein refers to an alkyl, cycloalkyl, alkenyl, or alkynyl group covalently bonded to an oxygen atom. The term "alkanoyl" as used herein refers to —C(=O)-alkyl, which may alternatively be referred to as "acyl." The term "alkanoyloxy" as used herein refers to —O—C(=O)-alkyl groups. The term "alkylamino" as used herein refers to the group —NRR', where R and R' are each either hydrogen or alkyl, and at least one of R and R' is alkyl. Alkylamino includes groups such as piperidino wherein R and R' form a ring. The term "alkylaminoalkyl" refers to -alkyl-NRR'.

The term "aryl" as used herein refers to any stable monocyclic, bicyclic, or polycyclic carbon ring system of from 4 to 12 atoms in each ring, wherein at least one ring is aromatic. Some examples of an aryl include phenyl, naphthyl, tetrahydro-naphthyl, indanyl, and biphenyl. Where an aryl substituent is bicyclic and one ring is non-aromatic, it is understood that attachment is to the aromatic ring. An aryl may be substituted or unsubstituted.

The term "heteroaryl" as used herein refers to any stable monocyclic, bicyclic, or polycyclic carbon ring system of from 4 to 12 atoms in each ring, wherein at least one ring is aromatic and contains from 1 to 4 heteroatoms selected from oxygen, nitrogen and sulfur. Some examples of a heteroaryl include acridinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, and tetrahydroquinolinyl. A heteroaryl includes the N-oxide derivative of a nitrogen-containing heteroaryl.

The term "heterocycle" or "heterocyclyl" as used herein refers to an aromatic or nonaromatic ring system of from five to twenty-two atoms, wherein from 1 to 4 of the ring atoms are heteroatoms selected from oxygen, nitrogen, and sulfur. Thus, a heterocycle may be a heteroaryl or a dihydro or tetrathydro version thereof.

The term "aroyl" as used herein refers to an aryl radical derived from an aromatic carboxylic acid, such as a substituted benzoic acid. The term "aralkyl" as used herein refers to an aryl group bonded to an alkyl group, for example, a benzyl group.

The term "carboxyl" as used herein represents a group of the formula —C(=O)OH or —C(=O)O$^-$. The terms "carbonyl" and "acyl" as used herein refer to a group in which an oxygen atom is double-bonded to a carbon atom >C=O. The term "hydroxyl" as used herein refers to —OH or —O$^-$. The term "nitrile" or "cyano" as used herein refers to —CN. The term "halogen" or "halo" refers to fluoro (—F), chloro (—Cl), bromo (—Br), and iodo (—I).

The term "substituted" as used herein refers to an atom having one or more substitutions or substituents which can be the same or different and may include a hydrogen substituent. Thus, the terms alkyl, cycloalkyl, alkenyl, alkynyl, alkoxy, alkanoyl, alkanoyloxy, alkylamino, alkylaminoalkyl, aryl, heteroaryl, heterocycle, aroyl, and aralkyl as used herein refer to groups which include substituted variations. Substituted variations include linear, branched, and cyclic variations, and groups having a substituent or substituents replacing one or more hydrogens attached to any carbon atom of the group. Substituents that may be attached to a carbon atom of the group include alkyl, cycloalkyl, alkenyl, alkynyl, alkoxy, alkanoyl, alkanoyloxy, alkylamino, alkylaminoalkyl, aryl, heteroaryl, heterocycle, aroyl, aralkyl, acyl, hydroxyl, cyano, halo, haloalkyl, amino, aminoacyl, alkylaminoacyl, acyloxy, aryloxy, aryloxyalkyl, mercapto, nitro, carbamyl, carbamoyl, and heterocycle. For example, the term ethyl includes without limitation —CH$_2$CH$_3$, —CHFCH$_3$, —CF$_2$CH$_3$, —CHFCH$_2$F, —CHFCHF$_2$, —CHFCF$_3$, —CF$_2$CH$_2$F, —CF$_2$CHF$_2$, —CF$_2$CF$_3$, and other variations as described above. In general, substituents may be further substituted with any atom or group of atoms.

Amino acid lipids of this invention or variants thereof can be synthesized by methods known in the art.

Methods to prepare various organic groups and protective groups are known in the art and their use and modification is generally within the ability of one of skill in the art. See, e.g., Stanley R. Sandler and Wolf Karo, Organic Functional Group Preparations (1989); Greg T. Hermanson, Bioconjugate Techniques (1996); Leroy G. Wade, Compendium Of Organic Synthetic Methods (1980); examples of protective groups are found in T. W. Greene and P. G. M. Wuts, Protective Groups In Organic Synthesis (3rd ed. 1991).

A pharmaceutically acceptable salt of a peptide or protein composition of this invention which is sufficiently basic may be an acid-addition salt with, for example, an inorganic or organic acid such as hydrochloric, hydrobromic, sulfuric, nitric, phosphoric, chlorosulfonic, trifluoroacetic, citric, maleic, acetic, propionic, oxalic, malic, maleic, malonic, fumaric, or tartaric acids, and alkane- or arenesulfonic acids such as methanesulfonic, ethanesulfonic, benzenesulfonic, chlorobenzenesulfonic, toluenesulfonic, naphthalenesulfonic, naphthalenedisulfonic, and camphorsulfonic acids.

A pharmaceutically acceptable salt of a peptide or protein composition of this invention which is sufficiently acidic may be an alkali metal salt, for example, a sodium or potassium salt, or an alkaline earth metal salt, for example, a calcium or magnesium salt, or a zinc or manganese salt, or an ammonium salt or a salt with an organic base which provides a physiologically-acceptable cation, for example, a salt with methylamine, dimethylamine, trimethylamine, triethylamine, ethanolamine, diethanolamine, triethanolamine, ethylenediamine, tromethamine, N-methylglucamine, piperidine, morpholine or tris-(2-hydroxyethyl)amine, and including salts of amino acids such as arginate, and salts of organic acids such as glucuronic or galactunoric acids. See, for example, Berge et al., J. Pharm. Sci. 66:1-19, 1977.

A salt or pharmaceutically-acceptable salt of a composition of this disclosure which contains an interfering-RNA agent and a lipid, peptide, or protein, among other components, may contain a salt complex of the interfering-RNA agent and the lipid, peptide, or protein. A salt complex of the interfering-RNA agent and the lipid, peptide, or protein may be formed from a pharmaceutically-acceptable salt of an interfering-RNA agent, or from a pharmaceutically-acceptable salt of the lipid, peptide, or protein.

Some compounds of this disclosure may contain both basic and acidic functionalities that may allow the compounds to be made into either a base or acid addition salt.

Some compounds, peptides and/or protein compositions of this invention may have one or more chiral centers and/or geometric isomeric centers (E- and Z-isomers), and it is to be understood that the invention encompasses all such optical isomers, diastereoisomers, geometric isomers, and mixtures thereof.

This invention encompasses any and all tautomeric, solvated or unsolvated, hydrated or unhydrated forms, as well as any atom isotope forms of the compounds, peptides and/or protein compositions disclosed herein.

Additional Delivery Lipids

In some aspects of this invention, amino acid lipids and additional non-amino acid lipids may be employed for delivery and administration of regulatory RNA components, RNA antagonists, interfering RNA, or nucleic acids. More particularly, a composition of this invention may include one or more amino acid lipids along with non-amino acid cationic lipids and non-amino acid non-cationic lipids.

Non-amino acid cationic lipids may be monocationic or polycationic. Some non-amino acid cationic lipids include neutral lipids and lipids having approximately zero net charge at a particular pH, for example, a zwitterionic lipid. Non-amino acid non-cationic lipids also include anionic lipids.

In some embodiments, a composition is a mixture or complex of an RNA component with an amino acid lipid and a non-amino acid cationic lipid. In some embodiments, a composition may be a mixture or complex of one or more regulatory or interfering RNA agents with one or more amino acid lipids and one or more non-amino acid cationic lipids.

The compounds and compositions of this disclosure can be admixed with, or attached to various targeting ligands or agents to deliver an active agent to a cell, tissue, organ or region of an organism. Examples of targeting agents include antibodies, ligands for receptors, peptides, proteins, lectins, (poly)saccharides, galactose, mannose, cyclodextrins, nucleic acids, DNA, RNA, aptamers, and polyamino acids.

Examples of non-amino acid cationic lipids include N-[1-(2,3-dioleoyloxy)propyl]-N,N,N-trimethylammonium chloride (DOTMA); 1,2-bis(oleoyloxy)-3-3-(trimethylammonium)propane (DOTAP), 1,2-bis(dimyrstoyloxy)-3-3-(trimethylammonia)propane (DMTAP); 1,2-dimyristyloxypropyl-3-dimethylhydroxyethylammonium bromide (DMRIE); dimethyldioctadecylammonium bromide (DDAB); 3-(N—(N',N'-dimethylaminoethane)carbamoyl)cholesterol (DC-Chol); 3β-[N',N'-diguanidinoethylaminoethane)carbamoyl cholesterol (BGTC); 2-(2-(3-(bis(3-aminopropyl)amino)propylamino)acetamido)-N,N-ditetradecylacetamide (RPR209120); pharmaceutically acceptable salts thereof, and mixtures thereof.

Examples of non-amino acid cationic lipids include 1,2-dialkenoyl-sn-glycero-3-ethylphosphocholines (EPCs), such as 1,2-dioleoyl-sn-glycero-3-ethylphosphocholine, 1,2-distearoyl-sn-glycero-3-ethylphosphocholine, 1,2-dipalmitoyl-sn-glycero-3-ethylphosphocholine, pharmaceutically acceptable salts thereof, and mixtures thereof.

Examples of non-amino acid cationic lipids include 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (DLinDMA), and 1,2-dilinolenyloxy-N,N-dimethyl-3-aminopropane (DLenDMA).

Examples of non-amino acid polycationic lipids include tetramethyltetrapalmitoyl spermine (TMTPS), tetramethyltetraoleyl spermine (TMTOS), tetramethlytetralauryl spermine (TMTLS), tetramethyltetramyristyl spermine (TMTMS), tetramethyldioleyl spermine (TMDOS), pharmaceutically acceptable salts thereof, and mixtures thereof.

Examples of non-amino acid polycationic lipids include 2,5-bis(3-aminopropylamino)-N-(2-(dioctadecylamino)-2-oxoethyl) pentanamide (DOGS); 2,5-bis(3-aminopropylamino)-N-(2-(di(Z)-octadeca-9-dienylamino)-2-oxoethyl) pentanamide (DOGS-9-en); 2,5-bis(3-aminopropylamino)-N-(2-(di(9Z,12Z)-octadeca-9,12-dienylamino)-2-oxoethyl) pentanamide (DLinGS); 3-beta-($N^4$—($N^1$,$N^8$-dicarbobenzoxyspermidine)carbamoyl)cholesterol (GL-67); (9Z,9'Z)-2-(2,5-bis(3-aminopropylamino)pentanamido)propane-1,3-diyl-dioctadec-9-enoate (DOSPER); 2,3-dioleyloxy-N-[2(sperminecarboxamido)ethyl]-N,N-dimethyl-1-propanaminium trifluoro-acetate (DOSPA); pharmaceutically acceptable salts thereof, and mixtures thereof.

Examples of non-amino acid cationic lipids include DS404-28 BGTC (CAS 182056-06-0), DOSPER (CAS 178532-92-8), GL-67 (179075-30-0), RPR209120 (CAS 433292-13-8), DOGS (12050-77-7), DOGS (9-en, C18:1), DLinGS (C18:2), and DOTMA (104162-48-3).

Examples of non-amino acid cationic lipids are described in U.S. Pat. Nos. 4,897,355; 5,279,833; 6,733,777; 6,376,248; 5,736,392; 5,334,761; 5,459,127; 2005/0064595; 5,208,036; 5,264,618; 5,279,833; 5,283,185; 5,753,613; and 5,785,992.

In some embodiments, the composition is a mixture or complex of an RNA component with an amino acid lipid and a non-amino acid non-cationic lipid. In some embodiments, the composition is a mixture or complex of one or more RNA components with one or more amino acid lipids and one or more non-amino acid non-cationic lipids.

Non-amino acid non-cationic lipids include neutral, zwitterionic, and anionic lipids. Thus, a non-cationic zwitterionic lipid may contain a cationic head group.

Examples of non-amino acid non-cationic lipids include 1,2-Dilauroyl-sn-glycerol (DLG); 1,2-Dimyristoyl-sn-glycerol (DMG); 1,2-Dipalmitoyl-sn-glycerol (DPG); 1,2-Distearoyl-sn-glycerol (DSG); 1,2-Dilauroyl-sn-glycero-3-phosphatidic acid (sodium salt; DLPA); 1,2-Dimyristoyl-sn-glycero-3-phosphatidic acid (sodium salt; DMPA); 1,2-Dipalmitoyl-sn-glycero-3-phosphatidic acid (sodium salt; DPPA); 1,2-Distearoyl-sn-glycero-3-phosphatidic acid (sodium salt; DSPA); 1,2-Diarachidoyl-sn-glycero-3-phosphocholine (DAPC); 1,2-Dilauroyl-sn-glycero-3-phosphocholine (DLPC); 1,2-Dimyristoyl-sn-glycero-3-phosphocholine (DMPC); 1,2-Dipalmitoyl-sn-glycero-0-ethyl-3-phosphocholine (chloride or triflate; DPePC); 1,2-Dipalmitoyl-sn-glycero-3-phosphocholine (DPPC); 1,2-Distearoyl-sn-glycero-3-phosphocholine (DSPC); 1,2-Dilauroyl-sn-glycero-3-phosphoethanolamine (DLPE); 1,2-Dimyristoyl-sn-glycero-3-phosphoethanolamine (DMPE); 1,2-Dipalmitoyl-sn-glycero-3-phosphoethanolamine (DPPE); 1,2-Distearoyl-sn-glycero-3-phosphoethanolamine (DSPE); 1,2-Dilauroyl-sn-glycero-3-phosphoglycerol (sodium salt; DLPG); 1,2-Dimyristoyl-sn-glycero-3-phosphoglycerol (sodium salt; DMPG); 1,2-Dimyristoyl-sn-glycero-3-phospho-sn-1-glycerol (ammonium salt; DMP-sn-1-G); 1,2-Dipalmitoyl-sn-glycero-3-phosphoglycerol (sodium salt; DPPG); 1,2-Distearoyl-sn-glycero-3-phosphoglycero (sodium salt; DSPG); 1,2-Distearoyl-sn-glycero-3-phospho-sn-1-glycerol (sodium salt; DSP-sn-1-G); 1,2-Dipalmitoyl-sn-glycero-3-phospho-L-serine (sodium salt; DPPS); 1-Palmitoyl-2-linoleoyl-sn-glycero-3-phosphocholine (PLinoPC); 1-Palmitoyl-2-oleoyl-sn-glycero-3-phosphocholine (POPC); 1-Palmitoyl-2-oleoyl-sn-glycero-3-phosphoglycerol (sodium salt; POPG); 1-Palmitoyl-2-oleoyl-sn-glycero-3-phosphoglycerol (sodium salt; POPG); 1-Palmitoyl-2-oleoyl-sn-glycero-3-phosphoglycerol (ammonium salt; POPG); 1-Palmitoyl-2-4o-sn-glycero-3-phosphocholine (P-lyso-PC); 1-Stearoyl-2-lyso-sn-glycero-3-phosphocholine (S-lyso-PC); and mixtures thereof.

Examples of non-amino acid non-cationic lipids include polymeric compounds and polymer-lipid conjugates or polymeric lipids, such as pegylated lipids having PEG regions of 300, 500, 1000, 1500, 2000, 3500, or 5000 molecular weight, including polyethyleneglycols, N-(Carbonyl-methoxypolyethyleneglycol-2000)-1,2-dimyristoyl-sn-glycero-3-phosphoethanolamine (sodium salt; DMPE-MPEG-2000); N-(Carbonyl-methoxypolyethyleneglycol-5000)-1,2-dimyristoyl-sn-glycero-3-phosphoethanolamine (sodium salt; DMPE-MPEG-5000); N-(Carbonyl-methoxypolyethyleneglycol 2000)-1,2-dipalmitoyl-sn-glycero-3-phosphoethanolamine (sodium salt; DPPE-MPEG-2000); N-(Carbonyl-methoxypolyethyleneglycol 5000)-1,2-dipalmitoyl-sn-glycero-3-phosphoethanolamine (sodium salt; DPPE-MPEG-5000); N-(Carbonyl-methoxypolyethyleneglycol 750)-1,2-distearoyl-sn-glycero-3-phosphoethanolamine (sodium salt; DSPE-MPEG-750); N-(Carbonyl-methoxypolyethyleneglycol 2000)-1,2-distearoyl-sn-glycero-3-phosphoethanolamine (sodium salt; DSPE-MPEG-2000); N-(Carbonyl-methoxypolyethyleneglycol 5000)-1,2-distearoyl-sn-glycero-3-phosphoethanolamine (sodium salt; DSPE-MPEG-5000); sodium cholesteryl sulfate (SCS); pharmaceutically acceptable salts thereof, and mixtures thereof.

Examples of non-amino acid non-cationic lipids include polymeric lipids such as DOPE-PEG, DLPE-PEG, DDPE-PEG DLinPE-PEG, and diacylglycerol-PEG-2000 or -5000.

Examples of non-amino acid non-cationic lipids include polymeric lipids such as multi-branched pegylated compounds, for example DSPE-PTE020 and DSPE-AM0530K.

Examples of non-amino acid non-cationic lipids include polymeric lipids such as DSPE-PG8G polyglycerine lipids.

Examples of non-amino acid non-cationic lipids include dioleoylphosphatidylethanolamine (DOPE), diphytanoylphosphatidylethanolamine (DPhPE), 1,2-Dioleoyl-sn-Glycero-3-Phosphocholine (DOPC), and 1,2-Diphytanoyl-sn-Glycero-3-Phosphocholine (DPhPC).

Examples of non-amino acid non-cationic lipids include cholesterols, sterols, and steroids such as gonanes, estranes, androstanes, pregnanes, cholanes, cholestanes, ergostanes, campestanes, poriferastanes, stigmastanes, gorgostanes, lanostanes, cycloartanes, as well as sterol or zoosterol derivatives of any of the foregoing, and their biological intermediates and precursors, which may include, for example, cholesterol, lanosterol, stigmastanol, dihydrolanosterol, zymosterol, zymostenol, desmosterol, 7-dehydrocholesterol, and mixtures and derivatives thereof.

Examples of non-amino acid non-cationic lipids include pegylated cholesterols, and cholestane 3-oxo(C1-22acyl) derivatives such as cholesteryl acetate, cholesteryl arachidonate, cholesteryl butyrate, cholesteryl hexanoate, cholesteryl caprylate, cholesteryl n-decanoate, cholesteryl dodecanoate, cholesteryl myristate, cholesteryl palmitate, cholesteryl behenate, cholesteryl stearate, cholesteryl nervonate, cholesteryl pelargonate, cholesteryl n-valerate, cholesteryl oleate, cholesteryl elaidate, cholesteryl erucate, cholesteryl heptanoate, cholesteryl linolelaidate, cholesteryl linoleate, and mixtures and derivatives thereof.

Examples of non-amino acid non-cationic lipids include compounds derived from plant sterols including phytosterols, beta-sitosterol, campesterol, ergosterol, brassicasterol, delta-7-stigmasterol, delta-7-avenasterol, and mixtures and derivatives thereof.

Examples of non-amino acid non-cationic lipids include bile acids, cholic acid, chenodeoxycholic acid, glycocholic acid, taurocholic acid, deoxycholic acid, lithocholic acid, methyl-lithocholic acid, and mixtures and derivatives thereof.

Examples of non-amino acid non-cationic lipids include compounds derived from steroids including glucocorticoids, cortisol, hydrocortisone, corticosterone, $\Delta^5$-pregnenolone, progesterone, deoxycorticosterone, 17-OH-pregnenolone, 17-OH-progesterone, 11-dioxycortisol, dehydroepiandrosterone, dehydroepiandrosterone sulfate, androstenedione, aldosterone, 18-hydroxycorticosterone, tetrahydrocortisol, tetrahydrocortisone, cortisone, prednisone, 6α-methylpredisone, 9α-fluoro-16α-hydroxyprednisolone, 9α-fluoro-16α-methylprednisolone, 9α-fluorocortisol, and mixtures and derivatives thereof.

Examples of non-amino acid non-cationic lipids include compounds derived from steroids including adrogens, testosterone, dihydrotestosterone, androstenediol, androstenedione, androstenedione, 3α,5α-androstanediol, and mixtures and derivatives thereof.

Examples of non-amino acid non-cationic lipids include compounds derived from steroids including estrogens, estriols, estrones, estradiols, and mixtures and derivatives thereof.

Examples of non-amino acid non-cationic lipids include compounds derived from lumisterol and vitamin D compounds.

Examples of non-amino acid non-cationic lipids include lipids having tails ranging from C10:0 to C22:6, for example, DDPE (C10:0) (CAS 253685-27-7), DLPE (C12:0) (CAS 59752-57-7), DSPE (C18:0) (CAS 1069-79-0), DOPE (C18:1) (CAS 4004-05-1), DLinPE (C18:2) (CAS 20707-71-5), DLenPE (C18:3) (CAS 34813-40-6), DARAPE (C20:4) (CAS 5634-86-6), DDHAPE (C22:6) (CAS 123284-81-1), DPhPE (16:0[$(CH_3)_4$]) (CAS 201036-16-0).

Examples of non-amino acid anionic lipids include phosphatidylserine, phosphatidic acid, phosphatidylcholine, platelet-activation factor (PAF), phosphatidylethanolamine, phosphatidyl-DL-glycerol, phosphatidylinositol, phosphatidylinositol (pi(4)p, pi(4,5)p2), cardiolipin (sodium salt), lysophosphatides, hydrogenated phospholipids, sphingolipids, gangliosides, phytosphingosine, sphinganines, pharmaceutically acceptable salts thereof, and mixtures thereof.

Uses for Regulatory RNA and RNA Interference

In some aspects, this disclosure relates generally to the fields of regulatory RNA and RNA interference, antisense therapeutics, and delivery of RNA therapeutics. More particularly, this invention relates to compositions and formulations for ribonucleic acids, and their uses for medicaments and for delivery as therapeutics. This invention relates generally to methods of using ribonucleic acids in RNA interference for gene-specific inhibition of gene expression in cells, or in mammals to alter a disease state or a phenotype.

RNA interference refers to methods of sequence-specific post-transcriptional gene silencing which is mediated by a double-stranded RNA (dsRNA) called a short interfering RNA (siRNA). See Fire, et al., *Nature* 391:806, 1998, and Hamilton, et al., *Science* 286:950-951, 1999. RNAi is shared by diverse flora and phyla and is believed to be an evolutionarily-conserved cellular defense mechanism against the expression of foreign genes. See Fire, et al., *Trends Genet.* 15:358, 1999.

RNAi is therefore a ubiquitous, endogenous mechanism that uses small noncoding RNAs to silence gene expression. See Dykxhoorn, D. M. and J. Lieberman, *Annu. Rev.*

Biomed. Eng. 8:377-402, 2006. RNAi can regulate important genes involved in cell death, differentiation, and development. RNAi may also protect the genome from invading genetic elements, encoded by transposons and viruses. When a siRNA is introduced into a cell, it binds to the endogenous RNAi machinery to disrupt the expression of mRNA containing complementary sequences with high specificity. Any disease-causing gene and any cell type or tissue can potentially be targeted. This technique has been rapidly utilized for gene-function analysis and drug-target discovery and validation. Harnessing RNAi also holds great promise for therapy, although introducing siRNAs into cells in vivo remains an important obstacle.

The mechanism of RNAi, although not yet fully characterized, is through cleavage of a target mRNA. The RNAi response involves an endonuclease complex known as the RNA-induced silencing complex (RISC), which mediates cleavage of a single-stranded RNA complementary to the antisense strand of the siRNA duplex. Cleavage of the target RNA takes place in the middle of the region complementary to the antisense strand of the siRNA duplex (Elbashir, et al., *Genes Dev.* 15:188, 2001).

One way to carry out RNAi is to introduce or express a siRNA in cells. Another way is to make use of an endogenous ribonuclease III enzyme called dicer. One activity of dicer is to process a long dsRNA into siRNAs. See Hamilton, et al., *Science* 286:950-951, 1999; Berstein, et al., *Nature* 409:363, 2001. A siRNA derived from dicer is typically about 21-23 nucleotides in overall length with about 19 base pairs duplexed. See Hamilton, et al., supra; Elbashir, et al., *Genes Dev.* 15:188, 2001. In essence, a long dsRNA can be introduced in a cell as a precursor of a siRNA.

This invention provides a range of compositions, formulations and methods which include a regulatory RNA, an interfering nucleic acid or a precursor thereof in combination with various components including lipids, amino acid lipids, and natural or synthetic polymers.

The term "dsRNA" as used herein refers to any nucleic acid molecule comprising at least one ribonucleotide molecule and capable of inhibiting or down regulating gene expression, for example, by promoting RNA interference ("RNAi") or gene silencing in a sequence-specific manner. The dsRNAs of this disclosure may be suitable substrates for Dicer or for association with RISC to mediate gene silencing by RNAi. One or both strands of the dsRNA can further comprise a terminal phosphate group, such as a 5'-phosphate or 5',3'-diphosphate. As used herein, dsRNA molecules, in addition to at least one ribonucleotide, can further include substitutions, chemically-modified nucleotides, and non-nucleotides. In certain embodiments, dsRNA molecules comprise ribonucleotides up to about 100% of the nucleotide positions.

Examples of dsRNA molecules can be found in, for example, U.S. patent application Ser. No. 11/681,725, U.S. Pat. Nos. 7,022,828 and 7,034,009, and PCT International Application Publication No. WO/2003/070897.

Examples of modified nucleosides are found in U.S. Pat. Nos. 6,403,566, 6,509,320, 6,479,463, 6,191,266, 6,083,482, 5,712,378, and 5,681,940. A modified nucleoside may have the following structure:

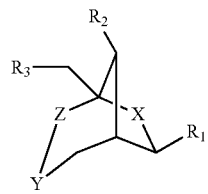

wherein, X is O or $CH_2$, Y is O, and Z is $CH_2$; $R_1$ is selected from the group of adenine, cytosine, guanine, hypoxanthine, uracil, thymine, and a heterocycle wherein the heterocycle is selected from the group of a substituted 1,3-diazine, an unsubstituted 1,3-diazine, and an unsubstituted 7H imidazo [4,5]1,3 diazine; and $R_2$, $R_3$ are independently selected from the group of H, OH, DMTO, TBDMSO, BnO, THPO, AcO, BzO, $OP(NiPr_2)O(CH_2)_2CN$, $OPO_3H$, diphosphate, and triphosphate, wherein $R_2$ and $R_3$ together may be $PhCHO_2$, $TIPDSO_2$ or $DTBSO_2$. As used herein, the abbreviation "Ac" refers to acetyl; the abbreviation "Bn" refers to benzyl; the abbreviation "Bz" refers to benzoyl; the abbreviation "DMT" refers to dimethoxytrityl; the abbreviation "THP" refers to tetrahydropyranyl; the abbreviation "TBDMS" refers to t-butyldimethylsilyl; the abbreviation "TIPDS" refers to tetraisopropyldisilyl; and the abbreviation "DTBS" refers to di(t-butyl)silyl.

In addition, as used herein, the terms "dsRNA," "RNAi-inducing agent," and "RNAi-agent" are meant to be synonymous with other terms used to describe nucleic acid molecules that are capable of mediating sequence specific RNAi including meroduplex RNA (mdRNA), nicked dsRNA (ndsRNA), gapped dsRNA (gdsRNA), short interfering nucleic acid (siRNA), siRNA, microRNA (miRNA), single strand RNA, short hairpin RNA (shRNA), short interfering oligonucleotide, short interfering substituted oligonucleotide, short interfering modified oligonucleotide, chemically-modified dsRNA, and post-transcriptional gene silencing RNA (ptgsRNA), as well as precursors of any of the above.

The term "large double-stranded (ds) RNA" refers to any double-stranded RNA longer than about 40 base pairs (bp) to about 100 bp or more, particularly up to about 300 bp to about 500 bp. The sequence of a large dsRNA may represent a segment of an mRNA or an entire mRNA. A double-stranded structure may be formed by self-complementary nucleic acid molecule or by annealing of two or more distinct complementary nucleic acid molecule strands.

In some aspects, a dsRNA comprises two separate oligonucleotides, comprising a first strand (antisense) and a second strand (sense), wherein the antisense and sense strands are self-complementary (i.e., each strand comprises a nucleotide sequence that is complementary to a nucleotide sequence in the other strand and the two separate strands form a duplex or double-stranded structure, for example, wherein the double-stranded region is about 15 to about 24 base pairs or about 26 to about 40 base pairs); the antisense strand comprises a nucleotide sequence that is complementary to a nucleotide sequence in a target nucleic acid molecule or a portion thereof (e.g., a human mRNA); and the sense strand comprises a nucleotide sequence corresponding (i.e., homologous) to the target nucleic acid sequence or a portion thereof (e.g., a sense strand of about 15 to about 25 nucleotides or about 26 to about 40 nucleotides corresponds to the target nucleic acid or a portion thereof).

In some embodiments, the dsRNA may be assembled from a single oligonucleotide in which the self-complementary sense and antisense strands of the dsRNA are linked by together by a nucleic acid based-linker or a non-nucleic acid-based linker. In some embodiments, the first (antisense) and second (sense) strands of the dsRNA molecule are covalently linked by a nucleotide or non-nucleotide linker as described herein and known in the art. In some embodiments, a first dsRNA molecule is covalently linked to at least one second dsRNA molecule by a nucleotide or non-nucleotide linker known in the art, wherein the first dsRNA molecule can be linked to a plurality of other dsRNA molecules that can be the same or different, or any combination thereof. In some embodiments, the linked dsRNA may include a third strand that forms a meroduplex with the linked dsRNA.

In some respects, dsRNA molecules described herein form a meroduplex RNA (mdRNA) having three or more strands, for example, an 'A' (first or antisense) strand, 'S1' (second) strand, and 'S2' (third) strand in which the 'S1' and 'S2' strands are complementary to and form base pairs (bp) with non-overlapping regions of the 'A' strand (e.g., an mdRNA can have the form of A:S1S2). The S1, S2, or more strands together essentially comprise a sense strand to the 'A' strand. The double-stranded region formed by the annealing of the 'S1' and 'A' strands is distinct from and non-overlapping with the double-stranded region formed by the annealing of the 'S2' and 'A' strands. An mdRNA molecule is a "gapped" molecule, meaning a "gap" ranging from 0 nucleotides up to about 10 nucleotides. In some embodiments, the A:S1 duplex is separated from the A:S2 duplex by a gap resulting from at least one unpaired nucleotide (up to about 10 unpaired nucleotides) in the 'A' strand that is positioned between the A:S1 duplex and the A:S2 duplex and that is distinct from any one or more unpaired nucleotide at the 3'-end of one or more of the 'A', 'S1', or 'S2' strands. In some embodiments, the A:S1 duplex is separated from the A:B2 duplex by a gap of zero nucleotides (i.e., a nick in which only a phosphodiester bond between two nucleotides is broken or missing in the polynucleotide molecule) between the A:S1 duplex and the A:S2 duplex—which can also be referred to as nicked dsRNA (ndsRNA). For example, A:S1S2 may be comprised of a dsRNA having at least two double-stranded regions that combined total about 14 base pairs to about 40 base pairs and the double-stranded regions are separated by a gap of about 0 to about 10 nucleotides, optionally having blunt ends, or A:S1S2 may comprise a dsRNA having at least two double-stranded regions separated by a gap of up to 10 nucleotides wherein at least one of the double-stranded regions comprises between about 5 base pairs and 13 base pairs.

As described herein, a dsRNA molecule which contains three or more strands may be referred to as a "meroduplex" RNA (mdRNA). Examples of mdRNA molecules can be found in U.S. Provisional Patent Application Nos. 60/934,930 and 60/973,398.

A dsRNA or large dsRNA may include a substitution or modification in which the substitution or modification may be in a phosphate backbone bond, a sugar, a base, or a nucleoside. Such nucleoside substitutions can include natural non-standard nucleosides (e.g., 5-methyluridine or 5-methylcytidine or a 2-thioribothymidine), and such backbone, sugar, or nucleoside modifications can include an alkyl or heteroatom substitution or addition, such as a methyl, alkoxyalkyl, halogen, nitrogen or sulfur, or other modifications known in the art.

In addition, as used herein, the term "RNAi" is meant to be equivalent to other terms used to describe sequence specific RNA interference, such as post transcriptional gene silencing, translational inhibition, or epigenetics. For example, dsRNA molecules of this disclosure can be used to epigenetically silence genes at the post-transcriptional level or the pre-transcriptional level or any combination thereof.

In some aspects, this invention provides compositions containing one or more RNAi-inducing agents which are targeted to one or more genes or target transcripts, along with one or more delivery components. Examples of delivery components include lipids, peptides, polymers, polymeric lipids, and conjugates thereof.

The compositions and formulations of this disclosure may be used for delivery of RNAi-inducing entities such as dsRNA, siRNA, mdRNA, miRNA, shRNA, or RNAi-inducing vectors to cells in intact mammalian subjects including humans, and may also be used for delivery of these agents to cells in culture.

This disclosure also provides methods for the delivery of one or more RNAi-inducing agents or entities to cells, organs and tissues within the body of a mammal. In some respects, compositions containing an RNAi-inducing entity may be introduced by various routes to be transported within the body and taken up by cells in one or more organs or tissues, where expression of a target transcript is modulated.

In general, this disclosure encompasses RNAi-inducing agents that are useful therapeutics to prevent and treat diseases or disorders characterized by various aberrant processes. For instance, viruses that infect mammals can replicate by taking control of cellular machinery of the host cell. See, e.g., Fields Virology (2001). Thus, dsRNAs are useful to disrupt viral pathways which control virus production or replication.

This disclosure includes methods for treating or preventing a viral infection in a subject by use of one or more therapeutic RNAi-inducing agents having a broad spectrum of efficacy against strains of a target virus. An RNAi-inducing agent of this invention can be targeted to a sequence of a viral gene in a known variant strain or variants of a virus, and exhibit sequence-specific gene silencing of the targeted viral gene in those variants. For example, an RNAi-inducing agent may be targeted to, and exhibit efficacy against a seasonal strain of influenza virus, as well as variant strains of influenza.

Compositions and formulations of this disclosure may be used for delivery of drug agents or biologically active agents to a variety of cells in vitro. Examples of cells for which in vitro delivery is encompassed include epithelial cells such as A549, immortal cell lines such as HeLa, hepatoma cells such as HepG2, rat gliosarcoma cells such as 9L/LacZ, human monocyte cells such as THP-1, Madin-Darby canine kidney cells (MDCK), various fibroblast cell lines, and primary cells in culture in the presence or absence of various sera, among others.

Compositions and formulations of this disclosure may be used for delivery of drug agents or biologically active agents to a variety of cells, tissues or organs in vivo. Modalities for delivering an agent in vivo include topical, enteral, and parenteral routes. Examples of modalities for delivering an agent in vivo include inhalation of particles or droplets, delivery of nasal or nasal-pharngyl drops, particles, or suspensions, transdermal and transmucosal routes, as well as injection or infusion by intramuscular, subcutaneous, intravenous, intraarterial, intracardiac, intrathecal, intraosseus, intraperitoneal, and epidural routes.

In some embodiments, an agent can be administered ex vivo by direct exposure to cells, tissues or organs originating from a mammalian subject.

A drug agent or biologically active agent to be delivered using a composition or formulation of this disclosure may be found in any form including, for example, a pure form, a crystalline form, a solid form, a nanoparticle, a condensed form, a complexed form, or a conjugated form.

This invention also provides methods for the delivery of one or more RNAi-inducing entities to organs and tissues within the body of a mammal. In some embodiments, compositions containing an RNAi-inducing entity, one or more amino acid lipids, and one or more additional lipid components are introduced by various routes to be transported within the body and taken up by cells in one or more organs or tissues, where expression of a target transcript is modulated.

This disclosure provides pharmaceutically acceptable nucleic acid compositions with various lipids useful for therapeutic delivery of nucleic acids and gene-silencing RNAs. In particular, this invention provides compositions and methods for in vitro and in vivo delivery of dsRNAs for decreasing, downregulating, or silencing the translation of a target nucleic acid sequence or expression of a gene. These compositions and methods may be used for prevention and/or treatment of diseases in a mammal. In exemplary methods of this invention, a ribonucleic acid molecule such as an siRNA or shRNA is contacted with an amino acid lipid to formulate a composition which can be administered to cells or subjects such as mammals. In some embodiments, this invention provides methods for delivering an siRNA or shRNA intracellularly by contacting a nucleic acid-containing composition with a cell.

In exemplary embodiments, this invention includes compositions containing a nucleic acid molecule, such as a double-stranded RNA (dsRNA), a short interfering RNA (siRNA), or a short hairpin RNA (shRNA), admixed or complexed with an amino acid lipid, and a polymeric lipid to form a composition that enhances intracellular delivery of the nucleic acid molecule. In some embodiments, a delivery composition of this invention may contain a dsRNA and one, two, or more amino acid lipids, which may be cationic or non-cationic. In some variations, a delivery composition may contain a dsRNA, amino acid lipids, and one or more polymeric lipids. In some embodiments, a delivery composition may contain a dsRNA, amino acid lipids, one or more additional lipids, and one or more polymeric lipids. The compositions of this invention can form stable particles which may incorporate a dsRNA as an interfering RNA agent. Compositions and formulations of this invention may include further delivery-enhancing components or excipients.

In some embodiments, compositions of this invention contain stable RNA-lipid particles having diameters from about 5 nm to about 400 nm. In some embodiments, the particles may have a uniform diameter of from about 10 nm to about 300 nm. In some embodiments, the particles may have a uniform diameter of from about 50 nm to about 150 nm.

Within exemplary compositions of this invention, a double-stranded RNA may be admixed or complexed with amino acid lipids to form a composition that enhances intracellular delivery of the dsRNA as compared to contacting target cells with naked dsRNA.

In some embodiments, a composition of this invention may contain one or more amino acid lipids which are from about 0.5% to about 70% (mol %) of the total amount of lipid and delivery-enhancing components, including any polymeric component, but not including the RNA component. In some embodiments, a composition of this invention may contain one or more amino acid lipids from about 10% to about 55%. In some embodiments, a composition of this invention may contain one or more amino acid lipids from about 15% to about 35%.

In certain embodiments, a composition of this invention may contain one or more non-amino acid non-cationic lipids, where the non-amino acid non-cationic lipids are from about 2% to about 95% (mol %) of the total amount of lipid and delivery-enhancing components, including any polymeric component, but not including the RNA component. In some embodiments, a composition of this invention may contain one or more non-cationic lipids from about 20% to about 75%, or from about 45% to about 75%, or from about 45% to about 55%. In some embodiments, a composition of this invention may contain one or more non-cationic lipids from about 10% to about 50%.

In some embodiments, a composition of this invention may contain one or more polymeric lipids, where the polymeric lipids are from about 0.2% to about 20% (mol %) of the total amount of lipid and delivery-enhancing components, including any polymeric component, but not including the RNA component. In some embodiments, a composition of this invention may contain one or more polymeric lipids from about 0.5% to about 10%. In some embodiments, a composition of this invention may contain one or more polymeric lipids from about 1% to about 5% of the composition.

Compositions and Uses for Nucleic Acid Therapeutics

In some embodiments, this invention provides a method of treating a disease or disorder in a mammalian subject. A therapeutically effective amount of a composition of this invention containing an interfering RNA, an amino acid lipid, a non-amino acid non-cationic lipid, a polymeric lipid, and one or more delivery-enhancing components or excipients may be administered to a subject having a disease or disorder associated with expression or overexpression of a gene that can be reduced, decreased, downregulated, or silenced by the composition.

This invention encompasses methods for treating a disease of the lung such as respiratory distress, asthma, cystic fibrosis, pulmonary fibrosis, chronic obstructive pulmonary disease, bronchitis, or emphysema, by administering to the subject a therapeutically effective amount of a composition.

This invention encompasses methods for treating rheumatoid arthritis, liver disease, encephalitis, bone fracture, heart disease, viral disease including hepatitis and influenza, or cancer.

Methods for making liposomes are given in, for example, G. Gregoriadis, Liposome Technology (CRC Press 1984), M. J. Ostro, Liposomes (Marcel Dekker 1987); Subhash C. Basu and Manju Basu, Liposome Methods and Protocols (2002).

The nucleic acid component, amino acid lipids, and any additional components may be mixed together first in a suitable medium such as a cell culture medium, after which one or more additional lipids or compounds may be added to the mixture. Alternatively, the amino acid lipids can be mixed together first in a suitable medium such as a cell culture medium, after which the nucleic acid component can be added.

Within certain embodiments of the invention, a dsRNA is admixed with one or more amino acid lipids, or a combination of one or more amino acid lipids and non-amino acid non-cationic lipids.

In some embodiments, an amino acid lipid transfection/delivery formulation can be prepared by rehydration of a dried preparation. The lipids may be solubilized in CHCl$_3$, dried under nitrogen, and rehydrated in 10 mM HEPES, 5% dextrose at pH 7.4, for example, and sonicated to form liposomes. Liposomes can be diluted in HEPES dextrose. The dsRNA may be diluted in 10 mM HEPES, 5% dextrose, pH 7.4, at 0.0008 mol/mL. One volume of liposome can be added to one volume dsRNA and vortexed (self assembly), providing a final dsRNA concentration of 100 nM to 6.25 nM dsRNA. This mixture can be diluted one to four in the presence of cell culture media.

The interfering RNA agent may also be complexed with, or conjugated to an amino acid lipid or polymeric lipid, and admixed with one or more non-amino acid non-cationic lipids, or a combination of one or more non-amino acid non-cationic and non-amino acid cationic lipids.

An interfering RNA agent and an amino acid lipid may be mixed together first, followed by the addition of one or more non-amino acid non-cationic lipids, or a combination of non-amino acid non-cationic and non-amino acid cationic lipids added in a suitable medium such as a cell culture medium. Alternatively, the amino acid lipids and non-amino acid lipid components may be mixed first, followed by the addition of the RNA agent in a suitable medium.

In some embodiments, this disclosure includes micellar dispersion compositions containing a drug or active agent admixed or complexed with an amino acid lipid and a dispersant to form a composition that provides intracellular delivery of the drug or active agent.

In certain embodiments, a dispersion composition of this disclosure may contain one or more drugs or active agents, one or more amino acid lipids, and one or more dispersants. In some variations, a delivery composition may contain a drug or active agent, a dispersant, an amino acid lipid, and an optional polymeric lipid. The dispersion compositions of this disclosure can form stable particles which may incorporate the drug or active agent.

In some aspects, a dispersion composition of this disclosure may contain stable nucleic acid dispersion particles having diameters from about 5 nm to about 400 nm. In some embodiments, the particles may have a uniform diameter of from about 10 nm to about 300 nm. In some embodiments, the particles may have a uniform diameter of from about 50 nm to about 150 nm.

A micellar dispersion can be used to formulate and improve the bioavailability of a drug or active agent, including RNAi therapeutics. While a conventional lipid-drug complex may contain a lipid bilayer or liposomal structure which maintains a hydrophilic or aqueous core, a micellar dispersion can provide dispersion droplets or nanoparticles having a hydrophobic oil-like core. The dispersion nanoparticles can be suspended in a continuous aqueous phase. A dispersion structure can avoid some disadvantages inherent in using a liposomal structure for delivery of active agents, and can provide advantages in delivery because of the lipophilic core.

This disclosure provides a range of micellar dispersion compositions containing lipids and dispersants for drugs or medicaments, and for delivery and administration of RNA agents.

Examples of dispersants include synthetic compounds including polyoxyglycerides such as polyglycolated capryl glycerides, ethoxy diglycol, pegylated fatty glycerides, diethylene glycol monoethyl ethers, and mixtures thereof. Examples of dispersants include LABRAFIL, LABRASOL, ARLATONE, TRANSCUTOL, and mixtures thereof.

Examples of dispersants include synthetic compounds such as alkylphospho-N-methylethanolamines and alkoylsarcosines. Examples of dispersants include FOS-MEA and CRODASINIC.

In some embodiments, a delivery composition of this disclosure may contain a drug or active agent, one or more oils, one or more amino acid lipids, and emulsifier and stabilizer lipids. In some variations, a delivery composition may contain a drug or active agent, an oil, a lipid emulsifier, an amino acid lipid, a non-cationic lipid, and a polymeric lipid.

The compositions of this disclosure can form stable particles which may incorporate a drug or active agent. In some aspects, compositions of this disclosure contain stable drug or active agent emulsion particles having diameters from about 5 nm to about 400 nm. In some embodiments, the particles may have a uniform diameter of from about 10 nm to about 300 nm. In some embodiments, the particles may have a uniform diameter of from about 50 nm to about 150 nm.

Within exemplary compositions of this disclosure, a drug or active agent may be admixed or complexed with an oil, an emulsifier, an amino acid lipid, and a polymeric stabilizing lipid, to form a composition that enhances intracellular delivery of the drug or active agent.

An oil-in-water emulsion can be used to formulate and improve the bioavailability of a drug or active agent, including RNAi therapeutics.

While a conventional lipid-drug complex may contain a lipid bilayer or liposomal structure which maintains a hydrophilic or aqueous core, an oil-in-water emulsion can provide emulsion droplets or nanoparticles having a lipid layer surrounding a hydrophobic oil core. The emulsion droplets or nanoparticles can be suspended in a continuous aqueous phase. An emulsion structure can avoid some disadvantages inherent in using a liposomal structure for delivery of active agents, and can provide advantages in delivery because of the lipophilic core.

A range of novel emulsion compositions are provided in this disclosure including novel compositions and uses of oils, emulsifiers, and lipid components with interfering-RNA agents.

Examples of oils include synthetic oils, fatty acid esters of propylene glycols, ethers of ethylene glycols, glyceryl oils, cholesteryl oils, vegetable oils, nut oils, essential oils, mineral oil, lipid-soluble compounds such as tocopherols and Vitamin E, and mixtures thereof. Examples of oils include synthetic oils such as CAPRYOL 90 (propylene glycol monoester), CAPRYOL PGMC (propylene glycol monoester), LABRAFAC PC (propylene glycol monoester), LABRAFAC PG (propylene glycol diester), LAUROGLYCOL 90 (propylene glycol monoester), LAUROGLYCOL FCC (propylene glycol monoester), PLUROL OLEIQUE CC 497 (propylene glycol monoester), LABRAFAC LIPOPHILE WL 1349 (triglyceride), PECEOL (glyceryl monoester), MAISINE 35-1 (glyceryl monoester), and mixtures thereof.

Compositions and Methods for RNA Therapeutics

This invention provides compositions and methods for modulating gene expression using regulatory RNA such as by RNA interference. A composition of this invention can deliver a ribonucleic acid agent to a cell which can produce the response of RNAi. Examples of nucleic acid agents useful for this invention include double-stranded nucleic acids, modified or degradation-resistant nucleic acids, RNA, siRNA, siRNA, shRNA, miRNA, piRNA, RNA antagonists, single-stranded nucleic acids, DNA-RNA chimeras, antisense nucleic acids, and ribozymes. As used herein, the terms siRNA, siRNA, and shRNA include precursors of siRNA, siRNA, and shRNA, respectively. For example, the term siRNA includes an RNA or double-stranded RNA that is suitable as a substrate of dicer enzyme.

Ribonucleic acid agents useful for this invention may be targeted to various genes. Examples of human genes suitable as targets include TNF, FLT1, the VEGF family, the ERBB family, the PDGFR family, BCR-ABL, and the MAPK family, among others. Examples of human genes suitable as targets and nucleic acid sequences thereto include those disclosed in PCT/US08/55333, PCT/US08/55339, PCT/US08/55340, PCT/US08/55341, PCT/US08/55350, PCT/US08/55353, PCT/US08/55356, PCT/US08/55357, PCT/US08/55360, PCT/US08/55362, PCT/US08/55365, PCT/US08/55366, PCT/US08/55369, PCT/US08/55370, PCT/US08/55371, PCT/US08/55372, PCT/US08/55373, PCT/US08/55374, PCT/US08/55375, PCT/US08/55376, PCT/US08/55377, PCT/US08/55378, PCT/US08/55380, PCT/US08/55381, PCT/US08/55382, PCT/US08/55383, PCT/US08/55385, PCT/US08/55386, PCT/US08/55505, PCT/US08/55511, PCT/US08/55515, PCT/US08/55516, PCT/US08/55519, PCT/US08/55524, PCT/US08/55526, PCT/US08/55527, PCT/US08/55532, PCT/US08/55533, PCT/US08/55542, PCT/US08/55548, PCT/US08/55550, PCT/US08/55551, PCT/US08/55554, PCT/US08/55556, PCT/US08/55560, PCT/US08/55563, PCT/US08/55597, PCT/US08/55599, PCT/US08/55601, PCT/US08/55603, PCT/US08/55604, PCT/US08/55606, PCT/US08/55608, PCT/US08/55611, PCT/US08/55612, PCT/US08/55615, PCT/US08/55618, PCT/US08/55622, PCT/US08/55625, PCT/US08/55627, PCT/US08/55631, PCT/US08/55635, PCT/US08/55644, PCT/US08/55649, PCT/US08/55651, PCT/US08/55662, PCT/US08/55672, PCT/US08/55676, PCT/US08/55678, PCT/US08/55695, PCT/US08/55697, PCT/US08/55698, PCT/US08/55701, PCT/US08/55704, PCT/US08/55708, PCT/US08/55709, and PCT/US08/55711.

An RNA of this disclosure to be delivered may have a sequence that is complementary to a region of a viral gene. For example, some compositions and methods of this invention are useful to regulate expression of the viral genome of an influenza virus. In some embodiments, this invention provides compositions and methods for modulating expression and infectious activity of an influenza by RNA interference. Expression and/or activity of an influenza can be modulated by delivering to a cell, for example, a short interfering RNA molecule having a sequence that is complementary to a region of a RNA polymerase subunit of an influenza. Examples of RNAs targeted to an influenza virus are given in U.S. Patent Publication No. 20070213293 A1.

In some embodiments, this invention provides compositions and methods for inhibiting expression of a target transcript in a subject by administering to the subject a composition containing an effective amount of an RNAi-inducing compound such as a short interfering oligonucleotide molecule, or a precursor thereof. RNAi uses small interfering RNAs (siRNAs) to target messenger RNA (mRNAs) and attenuate translation. A siRNA as used in this invention may be a precursor for dicer processing such as, for example, a long dsRNA processed into a siRNA. This invention provides methods of treating or preventing diseases or conditions associated with expression of a target transcript or activity of a peptide or protein encoded by the target transcript.

A therapeutic strategy based on RNAi can be used to treat a wide range of diseases by shutting down the growth or function of a virus or microorganism, as well as by shutting down the function of an endogenous gene product in the pathway of the disease.

In some embodiments, this invention provides novel compositions and methods for delivery of RNAi-inducing entities such as short interfering oligonucleotide molecules, and precursors thereof. In particular, this invention provides compositions containing an RNAi-inducing entity which is targeted to one or more transcripts of a cell, tissue, and/or organ of a subject.

A siRNA can be two RNA strands having a region of complementarity about 19 nucleotides in length. A siRNA optionally includes one or two single-stranded overhangs or loops.

A shRNA can be a single RNA strand having a region of self-complementarity. The single RNA strand may form a hairpin structure with a stem and loop and, optionally, one or more unpaired portions at the 5' and/or 3' portion of the RNA.

The active therapeutic agent can be a chemically-modified RNA with improved resistance to nuclease degradation in vivo, and/or improved cellular uptake, which retains RNAi activity.

A siRNA agent of this invention may have a sequence that is complementary to a region of a target gene. A siRNA of this invention may have 29-50 base pairs, for example, a dsRNA having a sequence that is complementary to a region of a target gene. Alternately, the double-stranded nucleic acid can be a dsDNA.

In certain embodiments, the active agent can be a short interfering nucleic acid (siRNA), short interfering RNA (siRNA), double-stranded RNA (dsRNA), micro-RNA, or short hairpin RNA (shRNA) that can modulate expression of a gene product.

Comparable methods and compositions are provided that target expression of one or more different genes associated with a particular disease condition in a subject, including any of a large number of genes whose expression is known to be aberrantly increased as a causal or contributing factor associated with the selected disease condition.

The RNAi-inducing compound of this invention can be administered in conjunction with other known treatments for a disease condition.

In some embodiments, this invention features compositions containing a small nucleic acid molecule, such as short interfering nucleic acid, a short interfering RNA, a double-stranded RNA, a micro-RNA, or a short hairpin RNA, admixed or complexed with, or conjugated to, a delivery-enhancing compound.

As used herein, the terms "regulatory RNA," "short interfering nucleic acid," "siRNA," "short interfering RNA," "short interfering oligonucleotide molecule," and "chemically-modified short interfering nucleic acid molecule," refer to any nucleic acid molecule capable of regulating, inhibiting or down regulating gene expression or, for example, viral replication, by mediating RNA interference (RNAi) or gene silencing in a sequence-specific manner. Regulatory RNA includes single-stranded RNA antagonists.

In some embodiments, the siRNA is a double-stranded polynucleotide molecule comprising self-complementary sense and antisense regions, wherein the antisense region comprises a nucleotide sequence that is complementary to a nucleotide sequence in a target ribonucleic acid molecule for down regulating expression, or a portion thereof, and the sense region comprises a nucleotide sequence corresponding to (i.e., which is substantially identical in sequence to) the target ribonucleic acid sequence or portion thereof.

As used herein, "siRNA" means a small interfering ribonucleic acid that is a relatively short-length double-stranded nucleic acid, or optionally a longer precursor thereof. The length of useful siRNAs within this invention will in some embodiments be preferred at a length of approximately 20 to 50 bp. However, there is no particular limitation to the length of useful siRNAs, including siRNAs. For example, siRNAs can initially be presented to cells in a precursor form that is substantially different than a final or processed form of the siRNA that will exist and exert gene silencing activity upon delivery, or after delivery, to the target cell. Precursor forms of siRNAs may, for example, include precursor sequence elements that are processed, degraded, altered, or cleaved at or after the time of delivery to yield a siRNA that is active within the cell to mediate gene silencing. In some embodiments, useful siRNAs will have a precursor length, for example, of approximately 100-200 base pairs, or 50-100 base pairs, or less than about 50 base pairs, which will yield an active, processed siRNA within the target cell. In other embodiments, a useful siRNA or siRNA precursor will be approximately 10 to 49 bp, or 15 to 35 bp, or about 21 to 30 bp in length.

In certain embodiments of this invention, polynucleotide delivery-enhancing polypeptides may be used to facilitate delivery of nucleic acid molecules, including large nucleic acid precursors of siRNAs. For example, the methods and compositions herein may be employed for enhancing delivery of larger nucleic acids that represent "precursors" to desired siRNAs, wherein the precursor amino acids may be cleaved or otherwise processed before, during or after delivery to a target cell to form an active siRNA for modulating gene expression within the target cell.

For example, a dsRNA precursor polynucleotide may be selected as a circular, single-stranded polynucleotide, having two or more loop structures and a stem comprising self-complementary sense and antisense regions, wherein the antisense region comprises a nucleotide sequence that is complementary to a nucleotide sequence in a target nucleic acid molecule or a portion thereof, and the sense region having nucleotide sequence corresponding to the target nucleic acid sequence or a portion thereof, and wherein the circular polynucleotide can be processed either in vivo or in vitro to generate an active dsRNA molecule capable of inducing RNAi.

siRNA molecules of this invention, particularly non-precursor forms, can be less than 30 base pairs, or about 17-19 bp, or 19-21 bp, or 21-23 bp.

siRNAs can mediate selective gene silencing in the mammalian system. Hairpin RNAs, with a short loop and 19 to 27 base pairs in the stem, also selectively silence expression of genes that are homologous to the sequence in the double-stranded stem. Mammalian cells can convert short hairpin RNA into siRNA to mediate selective gene silencing.

RISC mediates cleavage of single stranded RNA having sequence complementary to the antisense strand of the siRNA duplex. Cleavage of the target RNA takes place within the region complementary to the antisense strand of the siRNA duplex. siRNA duplexes of 21 nucleotides are typically most active when containing two-nucleotide 3'-overhangs.

Replacing the 3'-overhanging segments of a 21-mer siRNA duplex having 2-nucleotide 3' overhangs with deoxyribonucleotides may not have an adverse effect on RNAi activity. Replacing up to 4 nucleotides on each end of the siRNA with deoxyribonucleotides can be tolerated.

Alternatively, siRNAs can be delivered as single or multiple transcription products expressed by a polynucleotide vector encoding the single or multiple siRNAs and directing their expression within target cells. In these embodiments the double-stranded portion of a final transcription product of the siRNAs to be expressed within the target cell can be, for example, 15 to 49 bp, 15 to 35 bp, or about 21 to 30 bp long.

In some embodiments of this invention, the double-stranded region of siRNAs in which two strands are paired may contain bulge or mismatched portions, or both. Double-stranded portions of siRNAs in which two strands are paired are not limited to completely paired nucleotide segments, and may contain nonpairing portions due to, for example, mismatch (the corresponding nucleotides not being complementary), bulge (lacking in the corresponding complementary nucleotide on one strand), or overhang. Nonpairing portions can be contained to the extent that they do not interfere with siRNA formation. In some embodiments, a "bulge" may comprise 1 to 2 nonpairing nucleotides, and the double-stranded region of siRNAs in which two strands pair up may contain from about 1 to 7, or about 1 to 5 bulges. In addition, "mismatch" portions contained in the double-stranded region of siRNAs may be present in numbers from about 1 to 7, or about 1 to 5. Most often in the case of mismatches, one of the nucleotides is guanine, and the other is uracil. Such mismatching may be attributable, for example, to a mutation from C to T, G to A, or mixtures thereof, in a corresponding DNA coding for sense RNA, but other causes are also contemplated.

The terminal structure of siRNAs of this invention may be either blunt or cohesive (overhanging) as long as the siRNA retains its activity to silence expression of target genes. The cohesive (overhanging) end structure is not limited to the 3' overhang, but includes the 5' overhanging structure as long as it retains activity for inducing gene silencing. In addition, the number of overhanging nucleotides is not limited to 2 or 3 nucleotides, but can be any number of nucleotides as long as it retains activity for inducing gene silencing. For example, overhangs may comprise from 1 to about 8 nucleotides, or from 2 to 4 nucleotides.

The length of siRNAs having overhang end structure may be expressed in terms of the paired duplex portion and any overhanging portion at each end. For example, a 25/27-mer siRNA duplex with a 2-bp 3' antisense overhang has a 25-mer sense strand and a 27-mer antisense strand, where the paired portion has a length of 25 bp.

Any overhang sequence may have low specificity to a target gene, and may not be complementary (antisense) or identical (sense) to the target gene sequence. As long as the siRNA retains activity for gene silencing, it may contain in the overhang portion a low molecular weight structure, for example, a natural RNA molecule such as a tRNA, an rRNA, a viral RNA, or an artificial RNA molecule.

The terminal structure of the siRNAs may have a stem-loop structure in which ends of one side of the double-stranded nucleic acid are connected by a linker nucleic acid, for example, a linker RNA. The length of the double-stranded region (stem portion) can be, for example, 15 to 49 bp, or 15 to 35 bp, or about 21 to 30 bp long. Alternatively, the length of the double-stranded region that is a final transcription product of siRNAs to be expressed in a target cell may be, for example, approximately 15 to 49 bp, or 15 to 35 bp, or about 21 to 30 bp long.

The siRNA can contain a single stranded polynucleotide having a nucleotide sequence complementary to a nucleotide sequence in a target nucleic acid molecule, or a portion thereof, wherein the single stranded polynucleotide can contain a terminal phosphate group, such as a 5'-phosphate (see e.g. Martinez, et al., *Cell.* 110:563-574, 2002, and Schwarz, et al., *Molecular Cell* 10:537-568, 2002, or 5',3'-diphosphate.

As used herein, the term siRNA is not limited to molecules containing only naturally-occurring RNA or DNA, but also encompasses chemically-modified nucleotides and non-nucleotides. In some embodiments, the short interfering nucleic acid molecules of the invention lack 2'-hydroxy (2'-OH) containing nucleotides. In some embodiments, short interfering nucleic acids do not require the presence of nucleotides having a 2'-hydroxy group for mediating RNAi and as such, short interfering nucleic acid molecules of this invention optionally do not include any ribonucleotides (e.g., nucleotides having a 2'-OH group). siRNA molecules that do not require the presence of ribonucleotides within the siRNA molecule to support RNAi can, however, have an attached linker or linkers or other attached or associated groups, moieties, or chains containing one or more nucleotides with 2'-OH groups. siRNA molecules can comprise ribonucleotides in at least about 5, 10, 20, 30, 40, or 50% of the nucleotide positions.

As used herein, the term siRNA encompasses nucleic acid molecules that are capable of mediating sequence specific RNAi such as, for example, short interfering RNA (siRNA) molecules, double-stranded RNA (dsRNA) molecules, micro-RNA molecules, short hairpin RNA (shRNA) molecules, short interfering oligonucleotide molecules, short interfering nucleic acid molecules, short interfering modified oligonucleotide molecules, chemically-modified siRNA molecules, and post-transcriptional gene silencing RNA (ptgsRNA) molecules, among others.

In some embodiments, siRNA molecules comprise separate sense and antisense sequences or regions, wherein the sense and antisense regions are covalently linked by nucleotide or non-nucleotide linker molecules, or are non-covalently linked by ionic interactions, hydrogen bonding, van der waals interactions, hydrophobic interactions, and/or stacking interactions.

"Antisense RNA" is an RNA strand having a sequence complementary to a target gene mRNA, that can induce RNAi by binding to the target gene mRNA.

"Sense RNA" is an RNA strand having a sequence complementary to an antisense RNA, and anneals to its complementary antisense RNA to form a siRNA.

As used herein, the term "RNAi construct" or "RNAi precursor" refers to an RNAi-inducing compound such as small interfering RNAs (siRNAs), hairpin RNAs, and other RNA species which can be cleaved in vivo to form a siRNA. RNAi precursors herein also include expression vectors (also referred to as RNAi expression vectors) capable of giving rise to transcripts which form dsRNAs or hairpin RNAs in cells, and/or transcripts which can produce siRNAs in vivo.

A siHybrid molecule is a double-stranded nucleic acid that has a similar function to siRNA. Instead of a double-stranded RNA molecule, a siHybrid is comprised of an RNA strand and a DNA strand. Preferably, the RNA strand is the antisense strand which binds to a target mRNA. The siHybrid created by the hybridization of the DNA and RNA strands have a hybridized complementary portion and preferably at least one 3' overhanging end.

siRNAs for use within the invention can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure, for example wherein the double stranded region is about 19 base pairs). The antisense strand may comprise a nucleotide sequence that is complementary to a nucleotide sequence in a target nucleic acid molecule or a portion thereof, and the sense strand may comprise a nucleotide sequence corresponding to the target nucleic acid sequence or a portion thereof. Alternatively, the siRNA can be assembled from a single oligonucleotide, where the self-complementary sense and antisense regions of the siRNA are linked by means of a nucleic acid-based or non-nucleic acid-based linker(s).

In some embodiments, siRNAs for intracellular delivery can be a polynucleotide with a duplex, asymmetric duplex, hairpin or asymmetric hairpin secondary structure, having self-complementary sense and antisense regions, wherein the antisense region comprises a nucleotide sequence that is complementary to a nucleotide sequence in a separate target nucleic acid molecule or a portion thereof, and the sense region comprises a nucleotide sequence corresponding to the target nucleic acid sequence or a portion thereof.

Examples of chemical modifications that can be made in an siRNA include phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation.

The antisense region of a siRNA molecule can include a phosphorothioate internucleotide linkage at the 3'-end of said antisense region. The antisense region can comprise about one to about five phosphorothioate internucleotide linkages at the 5'-end of said antisense region. The 3'-terminal nucleotide overhangs of a siRNA molecule can include ribonucleotides or deoxyribonucleotides that are chemically-modified at a nucleic acid sugar, base, or backbone. The 3'-terminal nucleotide overhangs can include one or more universal base ribonucleotides. The 3'-terminal nucleotide overhangs can comprise one or more acyclic nucleotides.

For example, a chemically-modified siRNA can have 1, 2, 3, 4, 5, 6, 7, 8, or more phosphorothioate internucleotide linkages in one strand, or can have 1 to 8 or more phosphorothioate internucleotide linkages in each strand. The phosphorothioate internucleotide linkages can be present in one or both oligonucleotide strands of the siRNA duplex, for example in the sense strand, the antisense strand, or both strands.

siRNA molecules can comprise one or more phosphorothioate internucleotide linkages at the 3'-end, the 5'-end, or both of the 3'- and 5'-ends of the sense strand, the antisense strand, or in both strands. For example, an exemplary siRNA molecule can include 1, 2, 3, 4, 5, or more consecutive phosphorothioate internucleotide linkages at the 5'-end of the sense strand, the antisense strand, or both strands.

In certain embodiments, a siRNA molecule includes 1, 2, 3, 4, 5, 6, 7, 8, 9, 10, or more pyrimidine phosphorothioate internucleotide linkages in the sense strand, the antisense strand, or in both strands.

In some embodiments, a siRNA molecule includes 1, 2, 3, 4, 5, 6, 7, 8, 9, 10, or more purine phosphorothioate internucleotide linkages in the sense strand, the antisense strand, or in both strands.

A siRNA molecule can include a circular nucleic acid molecule, wherein the siRNA is about 38 to about 70, for example, about 38, 40, 45, 50, 55, 60, 65, or 70 nucleotides in length, having about 18 to about 23, for example, about 18, 19, 20, 21, 22, or 23 base pairs, wherein the circular oligonucleotide forms a dumbbell-shaped structure having about 19 base pairs and 2 loops.

A circular siRNA molecule can contain two loop motifs, wherein one or both loop portions of the siRNA molecule is biodegradable. For example, the loop portions of a circular siRNA molecule may be transformed in vivo to generate a double-stranded siRNA molecule with 3'-terminal overhangs, such as 3'-terminal nucleotide overhangs comprising about 2 nucleotides.

Modified nucleotides in a siRNA molecule can be in the antisense strand, the sense strand, or both. For example, modified nucleotides can have a Northern conformation (e.g., Northern pseudorotation cycle; see e.g., Saenger, *Principles of Nucleic Acid Structure*, Springer-Verlag ed., 1984). Examples of nucleotides having a Northern configuration include locked nucleic acid (LNA) nucleotides (e.g., 2'-O, 4'-C-methylene-(D-ribofuranosyl) nucleotides), 2'-methoxyethoxy (MOE) nucleotides, 2'-methyl-thio-ethyl, 2'-deoxy-2'-fluoro nucleotides, 2'-deoxy-2'-chloro nucleotides, 2'-azido nucleotides, and 2'-O-methyl nucleotides.

Chemically modified nucleotides can be resistant to nuclease degradation while at the same time maintaining the capacity to mediate RNAi.

The sense strand of a double stranded siRNA molecule may have a terminal cap moiety such as an inverted deoxyabasic moiety, at the 3'-end, 5'-end, or both 3' and 5'-ends of the sense strand.

Examples of conjugates include conjugates and ligands described in Vargeese, et al., U.S. application Ser. No. 10/427,160, filed Apr. 30, 2003, incorporated by reference herein in its entirety, including the drawings.

In some embodiments of this invention, the conjugate may be covalently attached to the chemically-modified siRNA molecule via a biodegradable linker. For example, the conjugate molecule may be attached at the 3'-end of either the sense strand, the antisense strand, or both strands of the chemically-modified siRNA molecule.

In certain embodiments, the conjugate molecule is attached at the 5'-end of either the sense strand, the antisense strand, or both strands of the chemically-modified siRNA molecule. In some embodiments, the conjugate molecule is attached both the 3'-end and 5'-end of either the sense strand, the antisense strand, or both strands of the chemically-modified siRNA molecule, or any combination thereof.

In some embodiments, a conjugate molecule comprises a molecule that facilitates delivery of a chemically-modified siRNA molecule into a biological system, such as a cell.

In some embodiments, a conjugate molecule attached to the chemically-modified siRNA molecule is a polyethylene glycol, human serum albumin, or a ligand for a cellular receptor that can mediate cellular uptake. Examples of specific conjugate molecules contemplated by the instant invention that can be attached to chemically-modified siRNA molecules are described in Vargeese, et al., U.S. Patent Publication Nos. 20030130186 and 20040110296.

A siRNA may be contain a nucleotide, non-nucleotide, or mixed nucleotide/non-nucleotide linker that joins the sense region of the siRNA to the antisense region of the siRNA. In some embodiments, a nucleotide linker can be 3, 4, 5, 6, 7, 8, 9, or 10 nucleotides in length. In some embodiments, the nucleotide linker can be a nucleic acid aptamer. As used herein, the terms "aptamer" or "nucleic acid aptamer" encompass a nucleic acid molecule that binds specifically to a target molecule, wherein the nucleic acid molecule contains a sequence that is recognized by the target molecule in its natural setting. Alternately, an aptamer can be a nucleic acid molecule that binds to a target molecule where the target molecule does not naturally bind to a nucleic acid.

For example, the aptamer can be used to bind to a ligand-binding domain of a protein, thereby preventing interaction of the naturally occurring ligand with the protein. See, for example, Gold, et al., *Annu. Rev. Biochem.* 64:763, 1995; Brody and Gold, *J. Biotechnol.* 74:5, 2000; Sun, *Curr. Opin. Mol. Ther.* 2:100, 2000; Kusser, *J. Biotechnol.* 74:27, 2000; Hermann and Patel, *Science* 287:820, 2000; and Jayasena, *Clinical Chemistry* 45:1628, 1999.

A non-nucleotide linker can be an abasic nucleotide, polyether, polyamine, polyamide, peptide, carbohydrate, lipid, polyhydrocarbon, or other polymeric compounds (e.g., polyethylene glycols such as those having between 2 and 100 ethylene glycol units). Specific examples include those described by Seela and Kaiser, *Nucleic Acids Res.* 18:6353, 1990, and *Nucleic Acids Res.* 15:3113, 1987; Cload and Schepartz, *J. Am. Chem. Soc.* 113:6324, 1991; Richardson and Schepartz, *J. Am. Chem. Soc.* 113:5109, 1991; Ma, et al., *Nucleic Acids Res.* 21:2585, 1993, and *Biochemistry* 32:1751, 1993; Durand, et al., *Nucleic Acids Res.* 18:6353, 1990; McCurdy, et al., *Nucleosides & Nucleotides* 10:287, 1991; Jaschke, et al., *Tetrahedron Lett.* 34:301-304, 1993; Ono, et al., *Biochemistry* 30:9914, 1991; Arnold, et al., International Publication No. WO 89/02439; Usman, et al., International Publication No. WO 95/06731; Dudycz, et al., International Publication No. WO 95/11910, and Ferentz and Verdine, *J. Am. Chem. Soc.* 113:4000, 1991.

A "non-nucleotide linker" refers to a group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

In some embodiments, modified siRNA molecule can have phosphate backbone modifications including one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl substitutions. Examples of oligonucleotide backbone modifications are given in Hunziker and Leumann, *Nucleic Acid Analogues: Synthesis and Properties, in Modern Synthetic Methods, VCH*, pp. 331-417, 1995, and Mesmaeker, et al., *Novel Backbone Replacements for Oligonucleotides, in Carbohydrate Modifications in Antisense Research, ACS*, pp. 24-39, 1994.

siRNA molecules, which can be chemically-modified, can be synthesized by: (a) synthesis of two complementary strands of the siRNA molecule; and (b) annealing the two complementary strands together under conditions suitable to obtain a double-stranded siRNA molecule. In some embodiments, synthesis of the complementary portions of the siRNA molecule is by solid phase oligonucleotide synthesis, or by solid phase tandem oligonucleotide synthesis.

Oligonucleotides (e.g., certain modified oligonucleotides or portions of oligonucleotides lacking ribonucleotides) are synthesized using protocols known in the art, for example, as described in Caruthers, et al., *Methods in Enzymology* 211:3-19, 1992; Thompson, et al., International PCT Publication No. WO 99/54459; Wincott, et al., *Nucleic Acids Res.* 23:2677-2684, 1995; Wincott, et al., *Methods Mol. Bio.* 74:59, 1997; Brennan, et al., *Biotechnol Bioeng.* 61:33-45, 1998; and Brennan, U.S. Pat. No. 6,001,311. Synthesis of RNA, including certain siRNA molecules of the invention, follows general procedures as described, for example, in Usman, et al., *J. Am. Chem. Soc.* 109:7845, 1987; Scaringe, et al., *Nucleic Acids Res.* 18:5433, 1990; and Wincott, et al., *Nucleic Acids Res.* 23:2677-2684, 1995; Wincott, et al., *Methods Mol. Bio.* 74:59, 1997.

An "asymmetric hairpin" as used herein is a linear siRNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop.

An "asymmetric duplex" as used herein is a siRNA molecule having two separate strands comprising a sense region and an antisense region, wherein the sense region comprises fewer nucleotides than the antisense region to the extent that the sense region has enough complementary nucleotides to base pair with the antisense region and form a duplex.

To "modulate gene expression" as used herein is to upregulate or downregulate expression of a target gene, which can include upregulation or downregulation of mRNA levels present in a cell, or of mRNA translation, or of synthesis of protein or protein subunits, encoded by the target gene.

The terms "inhibit," "down-regulate," or "reduce expression," as used herein mean that the expression of the gene, or level of RNA molecules or equivalent RNA molecules encoding one or more proteins or protein subunits, or level or activity of one or more proteins or protein subunits encoded by a target gene, is reduced below that observed in the absence of the nucleic acid molecules (e.g., siRNA) of the invention.

"Gene silencing" as used herein refers to partial or complete inhibition of gene expression in a cell and may also be referred to as "gene knockdown." The extent of gene silencing may be determined by methods known in the art, some of which are summarized in International Publication No. WO 99/32619.

As used herein, the terms "ribonucleic acid" and "RNA" refer to a molecule containing at least one ribonucleotide residue. A ribonucleotide is a nucleotide with a hydroxyl group at the 2' position of a beta-D-ribo-furanose moiety. These terms include double-stranded RNA, single-stranded RNA, isolated RNA such as partially purified RNA, essentially pure RNA, synthetic RNA, recombinantly produced RNA, as well as modified and altered RNA that differs from naturally occurring RNA by the addition, deletion, substitution, modification, and/or alteration of one or more nucleotides. Alterations of an RNA can include addition of non-nucleotide material, such as to the end(s) of a siRNA or internally, for example at one or more nucleotides of an RNA.

Nucleotides in an RNA molecule include non-standard nucleotides, such as non-naturally occurring nucleotides or chemically synthesized nucleotides or deoxynucleotides. These altered RNAs can be referred to as analogs.

By "highly conserved sequence region" is meant, a nucleotide sequence of one or more regions in a target gene does not vary significantly from one generation to the other or from one biological system to the other.

By "sense region" is meant a nucleotide sequence of a siRNA molecule having complementarity to an antisense region of the siRNA molecule. In addition, the sense region of a siRNA molecule can comprise a nucleic acid sequence having homology with a target nucleic acid sequence.

By "antisense region" is meant a nucleotide sequence of a siRNA molecule having complementarity to a target nucleic acid sequence. In addition, the antisense region of a siRNA molecule can include a nucleic acid sequence having complementarity to a sense region of the siRNA molecule.

By "target nucleic acid" is meant any nucleic acid sequence whose expression or activity is to be modulated. A target nucleic acid can be DNA or RNA.

By "complementarity" is meant that a nucleic acid can form hydrogen bond(s) with another nucleic acid sequence either by traditional Watson-Crick or by other non-traditional modes of binding.

The term "biodegradable linker" as used herein, refers to a nucleic acid or non-nucleic acid linker molecule that is designed as a biodegradable linker to connect one molecule to another molecule, for example, a biologically active molecule to a siRNA molecule or the sense and antisense strands of a siRNA molecule. The biodegradable linker is designed such that its stability can be modulated for a particular purpose, such as delivery to a particular tissue or cell type. The stability of a nucleic acid-based biodegradable linker molecule can be variously modulated, for example, by combinations of ribonucleotides, deoxyribonucleotides, and chemically-modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

In connection with 2'-modified nucleotides as described herein, by "amino" is meant 2'-$NH_2$ or 2'-O—$NH_2$, which can be modified or unmodified. Such modified groups are described, for example, in Eckstein, et al., U.S. Pat. No. 5,672,695 and Matulic-Adamic, et al., U.S. Pat. No. 6,248,878.

Supplemental or complementary methods for delivery of nucleic acid molecules for use within then invention are described, for example, in Akhtar et al., *Trends Cell Bio.* 2:139, 1992; "Delivery Strategies for Antisense Oligonucleotide Therapeutics," ed. Akhtar, 1995, Maurer et al., *Mol. Membr. Biol.* 16:129-140, 1999; Hofland and Huang, *Handb. Exp. Pharmacol.* 137:165-192, 1999; and Lee et al., *ACS Symp. Ser.* 752:184-192, 2000. Sullivan, et al., International PCT Publication No. WO 94/02595, further describes general methods for delivery of enzymatic nucleic acid molecules.

Nucleic acid molecules can be administered within formulations that include one or more additional components, such as a pharmaceutically acceptable carrier, diluent, excipient, adjuvant, emulsifier, buffer, stabilizer, or preservative.

As used herein, the term "carrier" means a pharmaceutically acceptable solid or liquid diluent, solvent, filler, or encapsulating material. Examples of carriers include saline, biological and pharmaceutical buffer systems, and biologically acceptable media. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. Examples of ingredients of the above categories can be found in the *U.S. Pharmacopeia National Formulary,* 1990, pp. 1857-1859, as well as in Raymond C. Rowe, et al., *Handbook of Pharmaceutical Excipients,* 5th ed., 2006, and "Remington: The Science and Practice of Pharmacy," 21st ed., 2006, editor David B. Troy.

Examples of preservatives include phenol, methyl paraben, paraben, m-cresol, thiomersal, benzylalkonium chloride, and mixtures thereof.

Examples of surfactants include oleic acid, sorbitan trioleate, polysorbates, lecithin, phosphotidylcholines, various long chain diglycerides and phospholipids, and mixtures thereof.

Examples of phospholipids include phosphatidylcholine, lecithin, phosphatidylglycerol, phosphatidylinositol, phosphatidylserine, and phosphatidylethanolamine, and mixtures thereof.

Examples of dispersants include ethylenediaminetetraacetic acid.

Examples of gases include nitrogen, helium, chlorofluorocarbons (CFCs), hydrofluorocarbons (HFCs), carbon dioxide, air, and mixtures thereof.

In certain embodiments, the siRNA and/or the polypeptide can be encapsulated in liposomes, or reside either internal or external to a liposome, or exist within liposome layers, or be administered by iontophoresis, or incorporated into other vehicles, such as hydrogels, cyclodextrins, biodegradable nanocapsules, bioadhesive microspheres, or proteinaceous vectors. See, for example, O'Hare and Normand, PCT International Publication No. WO 00/53722. Alternatively, a nucleic acid composition can be locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., *Clin. Cancer Res.* 5:2330-2337, 1999, and Barry et al., International PCT Publication No. WO 99/31262.

The compositions of this invention can be effectively employed as pharmaceutical agents. Pharmaceutical agents prevent, modulate the occurrence or severity of, or treat (alleviate one or more symptom(s) to a detectable or measurable extent) of a disease state or other adverse condition in a patient.

In some embodiments, this invention provides pharmaceutical compositions and methods featuring the presence or administration of one or more polynucleic acid(s), typically one or more siRNAs, combined, complexed, or conjugated with a lipid, which may further be formulated with a pharmaceutically-acceptable carrier, such as a diluent, stabilizer, or buffer.

Typically, the siRNA will target a gene that is expressed at an elevated level as a causal or contributing factor associated with the subject disease state or adverse condition. In this context, the siRNA will effectively downregulate expression of the gene to levels that prevent, alleviate, or reduce the severity or recurrence of one or more associated disease symptoms. Alternatively, for various distinct disease models where expression of the target gene is not necessarily elevated as a consequence or sequel of disease or other adverse condition, down regulation of the target gene will nonetheless result in a therapeutic result by lowering gene expression (i.e., to reduce levels of a selected mRNA and/or protein product of the target gene). Alternatively, siRNAs of the invention may be targeted to lower expression of one gene, which can result in upregulation of a "downstream" gene whose expression is negatively regulated by a product or activity of the target gene.

This siRNAs of this disclosure may be administered in any form, for example transdermally or by local injection (e.g., local injection at sites of psoriatic plaques to treat psoriasis, or into the joints of patients afflicted with psoriatic arthritis or RA). In more detailed embodiments, the invention provides formulations and methods to administer therapeutically effective amounts of siRNAs directed against of a mRNA of TNF-α, which effectively down-regulate the TNF-α RNA and thereby reduce or prevent one or more TNF-α-associated inflammatory condition(s). Comparable methods and compositions are provided that target expression of one or more different genes associated with a selected disease condition in animal subjects, including any of a large number of genes whose expression is known to be aberrantly increased as a causal or contributing factor associated with the selected disease condition.

The compositions of the present invention may also be formulated and used as tablets, capsules or elixirs for oral administration, suppositories for rectal administration, sterile solutions, suspensions for injectable administration, and the other forms known in the art.

A pharmacological composition or formulation refers to a composition or formulation in a form suitable for administration, for example, systemic administration, into a cell or patient, including for example a human. Suitable forms, in part, depend upon the use or the route of entry, for example oral, transdermal, transepithelial, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity.

By "systemic administration" is meant in vivo systemic absorption or accumulation of drugs in the blood stream followed by distribution throughout the entire body. Administration routes which lead to systemic absorption include, without limitation: intravenous, subcutaneous, intraperitoneal, inhalation, oral, intrapulmonary and intramuscular.

Examples of agents suitable for formulation with the nucleic acid molecules of this invention include: P-glycoprotein inhibitors (such as Pluronic P85), which can enhance entry of drugs into the CNS (Jolliet-Riant and Tillement, *Fundam. Clin. Pharmacol.* 13:16-26, 1999); biodegradable polymers, such as poly (DL-lactide-coglycolide) microspheres for sustained release delivery after intracerebral implantation (Emerich, D. F., et al., *Cell Transplant* 8:47-58, 1999, Alkermes, Inc., Cambridge, Mass.); and loaded nanoparticles, such as those made of polybutylcyanoacrylate, which can deliver drugs across the blood brain barrier and can alter neuronal uptake mechanisms (*Prog. Neuropsychopharmacol Biol. Psychiatry* 23:941-949, 1999). Other examples of delivery strategies for the nucleic acid molecules of the instant invention include material described in Boado, et al., *J. Pharm. Sci.* 87:1308-1315, 1998; Tyler, et al., *FEBS Lett.* 421:280-284, 1999; Pardridge, et al., *PNAS USA.* 92:5592-5596, 1995; Boado, *Adv. Drug Delivery Rev.* 15:73-107, 1995; Aldrian-Herrada et al., *Nucleic Acids Res.* 26:4910-4916, 1998; and Tyler, et al., *PNAS USA.* 96:7053-7058, 1999.

The present invention also includes compositions prepared for storage or administration, which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro ed. 1985). For example, preservatives, stabilizers, dyes and flavoring agents may be provided. These include sodium benzoate, sorbic acid and esters of p-hydroxybenzoic acid. In addition, antioxidants and suspending agents may be used.

A pharmaceutically effective dose is that dose required to prevent, inhibit the occurrence of, treat, or alleviate a symptom to some extent of a disease state. An amount of from 0.01 mg/kg to 50 mg/kg body weight/day of active nucleic acid should be administered.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The siRNAs can also be administered in the form of suppositories, for example, for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

The siRNAs can be modified extensively to enhance stability by modification with nuclease resistant groups, for example, 2'-amino, 2'-C-allyl, 2'-fluoro, 2'-O-methyl, 2'-H. For a review see Usman and Cedergren, *TIBS* 17:34, 1992; Usman, et al., *Nucleic Acids Symp. Ser.* 31:163, 1994. siRNA constructs can be purified by gel electrophoresis using general methods or can be purified by high pressure liquid chromatography and re-suspended in water.

Chemically synthesizing nucleic acid molecules with modifications (base, sugar and/or phosphate) can prevent their degradation by serum ribonucleases, which can increase their potency. See for example, Eckstein, et al., International Publication No. WO 92/07065; Perrault et al., *Nature* 344:565, 1990; Pieken, et al., *Science* 253, 314, 1991; Usman and Cedergren, *Trends in Biochem. Sci.* 17:334, 1992; Usman, et al., International Publication No. WO 93/15187; and Rossi et al., International Publication No. WO 91/03162; Sproat, U.S. Pat. No. 5,334,711; and Gold, et al., U.S. Pat. No. 6,300,074. All of the above references describe various chemical modifications that can be made to the base, phosphate and/or sugar moieties of the nucleic acid molecules described herein.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications. For a review, see Usman and Cedergren, *TIBS* 17:34, 1992; Usman, et al., *Nucleic Acids Symp. Ser.* 31:163, 1994; Burgin, et al., *Biochemistry* 35:14090, 1996. Sugar modification of nucleic acid molecules have been extensively described in the art. See Eckstein et al., International Publication PCT No. WO 92/07065; Perrault, et al. *Nature* 344:565-568, 1990; Pieken, et al. *Science* 253:314-317, 1991; Usman and Cedergren, *Trends in Biochem. Sci.* 17:334-339, 1992; Usman et al. International Publication PCT No. WO 93/15187; Sproat, U.S. Pat. No. 5,334,711 and Beigelman, et al., *J. Biol. Chem.* 270:25702, 1995; Beigelman, et al., International PCT Publication No. WO 97/26270; Beigelman, et al., U.S. Pat. No. 5,716,824; Usman, et al., U.S. Pat. No. 5,627,053; Woolf, et al., International PCT Publication No. WO 98/13526; Thompson, et al., Karpeisky, et al., *Tetrahedron Lett.* 39:1131, 1998; Earnshaw and Gait, *Biopolymers (Nucleic Acid Sciences)* 48:39-55, 1998; Verma and Eckstein, *Annu. Rev. Biochem.* 67:99-134, 1998; and Burlina, et al., *Bioorg. Med. Chem.* 5:1999-2010, 1997. Such publications describe general methods and strategies to determine the location of incorporation of sugar, base and/or phosphate modifications and the like into nucleic acid molecules without modulating catalysis. In view of such teachings, similar modifications can be used as described herein to modify the siRNA nucleic acid molecules of the instant invention so long as the ability of siRNA to promote RNAi in cells is not significantly inhibited.

While chemical modification of oligonucleotide internucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

In some embodiments, the invention features modified siRNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, *Nucleic Acid Analogues: Synthesis and Properties, in Modern Synthetic Methods, VCH,* 1995, pp. 331-417, and Mesmaeker, et al., "Novel Backbone Replacements for Oligonucleotides, in Carbohydrate Modifications in Antisense Research," *ACS,* 1994, pp. 24-39.

Methods for the delivery of nucleic acid molecules are described in Akhtar, et al., *Trends Cell Bio.* 2:139, 1992; "Delivery Strategies for Antisense Oligonucleotide Therapeutics," ed. Akhtar, 1995; Maurer, et al., *Mol. Membr. Biol.* 16:129-140, 1999; Hofland and Huang, *Handb. Exp. Pharmacol.* 137:165-192, 1999; and Lee, et al., *ACS Symp. Ser.* 752:184-192, 2000. Beigelman, et al., U.S. Pat. No. 6,395,713, and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation internally or externally by liposomes, by iontophoresis, or by incorporation into other vehicles, such as biodegradable polymers, hydrogels, cyclodextrins (see e.g. Gonzalez, et al., *Bioconjugate Chem.* 10:1068-1074, 1999; Wang, et al., International PCT Publication Nos. WO 03/47518 and WO 03/46185), poly(lactic-co-glycolic)acid (PLGA) and PLCA microspheres (see e.g. U.S. Pat. No. 6,447,796 and U.S. Patent Application Publication No. US 2002130430), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry, et al., *Clin. Cancer Res.* 5:2330-2337, 1999, and Barry, et al., International PCT Publication No. WO 99/31262. The molecules of the instant invention can be used as pharmaceutical agents. Pharmaceutical agents prevent, modulate the occurrence, or treat (alleviate a symptom to some extent, preferably all of the symptoms) of a disease state in a subject.

By "RNA" is meant a molecule comprising at least one ribonucleotide residue. By "ribonucleotide" is meant a nucleotide with a hydroxyl group at the 2' position of a .beta.-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or internally, for example, at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "cap structure" is meant chemical modifications, which have been incorporated at either terminus of the oligonucleotide (see, e.g. Adamic, et al., U.S. Pat. No. 5,998,203, incorporated by reference herein). These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Lyer, *Tetrahedron* 49:1925, 1993; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine and therefore lacks a base at the 1'-position.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, e.g. Usman and McSwiggen, supra; Eckstein, et al., International PCT Publication No. WO 92/07065; Usman, et al, International PCT Publication No. WO 93/15187; Uhlman & Peyman, supra, all are hereby incorporated by reference herein). There are several examples of modified nucleic acid bases known in the art as summarized by Limbach, et al., *Nucleic Acids Res.* 22:2183, 1994. Some of the non-limiting examples of base modifications that can be introduced into nucleic acid molecules include, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., *Biochemistry* 35:14090, 1996; Uhlman & Peyman, supra). By "modified bases" in this aspect is meant nucleotide bases other than adenine, guanine, cytosine and uracil at 1' position or their equivalents.

By "target site" or "target sequence" or "targeted sequence" is meant a sequence within a target nucleic acid (e.g., RNA) that is "targeted" for cleavage mediated by a siRNA construct which contains sequences within its antisense region that are complementary to the target sequence.

The siRNA molecules can be complexed with cationic lipids, packaged within liposomes, or otherwise delivered to target cells or tissues. The nucleic acid or nucleic acid complexes can be locally administered to through injection, infusion pump or stent, with or without their incorporation in biopolymers. In another embodiment, polyethylene glycol (PEG) can be covalently attached to siRNA compounds of the present invention, to the polypeptide, or both. The attached PEG can be any molecular weight, preferably from about 2,000 to about 50,000 daltons (Da).

The sense region can be connected to the antisense region via a linker molecule, such as a polynucleotide linker or a non-nucleotide linker.

"Inverted repeat" refers to a nucleic acid sequence comprising a sense and an antisense element positioned so that they are able to form a double stranded siRNA when the repeat is transcribed. The inverted repeat may optionally include a linker or a heterologous sequence such as a self-cleaving ribozyme between the two elements of the repeat. The elements of the inverted repeat have a length sufficient to form a double stranded RNA. Typically, each element of the inverted repeat is about 15 to about 100 nucleotides in length, preferably about 20-30 base nucleotides, preferably about 20-25 nucleotides in length, e.g., 20, 21, 22, 23, 24, 25, 26, 27, 28, 29, or 30 nucleotides in length.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

"Large double-stranded RNA" refers to any double-stranded RNA having a size greater than about 40 bp for example, larger than 100 bp or more particularly larger than 300 bp. The sequence of a large dsRNA may represent a segment of a mRNA or the entire mRNA. The maximum size of the large dsRNA is not limited herein. The double-stranded RNA may include modified bases where the modification may be to the phosphate sugar backbone or to the nucleoside. Such modifications may include a nitrogen or sulfur heteroatom or any other modification known in the art.

The double-stranded structure may be formed by self-complementary RNA strand such as occurs for a hairpin or a micro RNA or by annealing of two distinct complementary RNA strands.

"Overlapping" refers to when two RNA fragments have sequences which overlap by a plurality of nucleotides on one strand, for example, where the plurality of nucleotides (nt) numbers as few as 2-5 nucleotides or by 5-10 nucleotides or more.

"One or more dsRNAs" refers to dsRNAs that differ from each other on the basis of primary sequence.

"Target gene or mRNA" refers to any gene or mRNA of interest. Target genes or mRNA may include developmental genes and regulatory genes as well as metabolic or structural genes or genes encoding enzymes. The target gene may be endogenous or exogenous. The target gene may be expressed in those cells in which a phenotype is being investigated or in an organism in a manner that directly or indirectly impacts a phenotypic characteristic. Such cells include any cell in the body of an adult or embryonic animal or plant including gamete or any isolated cell such as occurs in an immortal cell line or primary cell culture.

Uses for Antisepsis Effects

In some aspects, this disclosure relates generally to the fields of sepsis. More particularly, this invention relates to compositions and formulations of amino acid lipids and their uses for medicaments and as therapeutics. This invention relates generally to methods of using amino acid lipids to prevent, treat or ameliorate sepsis, septic shock, inflammatory sepsis, septicemia, or systemic inflammatory response syndrome.

Sepsis can be caused by infection when the immune system is compromised or overwhelmed, or due to certain chemotherapies. For example, endotoxins of gram-negative bacteria can induce septic shock. Gram-negative sepsis is a leading cause of deaths in intensive care. Antimicrobial therapy alone may be insufficient to prevent death in sepsis cases. Sepsis can be accompanied by widespread activation of the innate immune response, leading to uncontrolled production of a variety of inflammatory mediators. The uncontrolled systemic inflammatory response can cause death.

Amino acid lipids of this disclosure may be active toward reducing the immune response to certain endotoxins such as lipopolysaccharides. Cationic amphipathic amino acid lipids of this disclosure may bind and neutralize endotoxins, thereby reducing the immune response. Thus, this disclosure contemplates uses of amino acid lipids in medicaments and methods for preventing, treating or ameliorating sepsis, septic shock, inflammatory sepsis, septicemia, or systemic inflammatory response syndrome.

Uses for Delivery of Active Agents

The compounds and compositions of this invention may be used for delivery of any physiologically active agent, as well as any combination of active agents, as described above or known in the art. The active agent may be present in the compositions and uses of this invention in an amount sufficient to provide the desired physiological or ameliorative effect.

The compounds and compositions of this invention are directed toward enhancing delivery of a range of drug agents and biologically active agents in mammalian subjects including small molecule compounds and drugs, peptides, proteins, and vaccine agents.

Examples of active agents include a peptide, a protein, a nucleic acid, a double-stranded RNA, a hematopoietic, an antiinfective; an antidementia; an antiviral, an antitumoral, an antipyretic, an analgesic, an anti-inflammatory, an anti-ulcerative, an antiallergenic, an antidepressant, a psychotropic, a cardiotonic, an antiarrythmic, a vasodilator, an antihypertensive, a hypotensive diuretic, an antidiabetic, an anticoagulant, a cholesterol-lowering agent, a therapeutic for osteoporosis, a hormone, an antibiotic, a vaccine, a cytokine, a hormone, a growth factor, a cardiovascular factor, a cell adhesion factor, a central or peripheral nervous system factor, a humoral electrolyte factor, a hemal organic substance, a bone growth factor, a gastrointestinal factor, a kidney factor, a connective tissue factor, a sense organ factor, an immune system factor, a respiratory system factor, a genital organ factor, an androgen, an estrogen, a prostaglandin, a somatotropin, a gonadotropin, an interleukin, a steroid, a bacterial toxoid, an antibody, a monoclonal antibody, a polyclonal antibody, a humanized antibody, an antibody fragment, and an immunoglobin.

Examples of active agents include erythropoietin, granulocyte-colony stimulating factor, insulin, Factor VIII, Factor IX, interferon, heparin, hirugen, hirulos, and hirudine.

Examples of active agents include morphine, hydromorphone, oxymorphone, lovorphanol, levallorphan, codeine, nalmefene, nalorphine, nalozone, naltrexone, buprenorphine, butorphanol, or nalbufine, cortisone, hydrocortisone, fludrocortisone, prednisone, prednisolone, methylprednisolone, triamcinolone, dexamethoasone, betamethoasone, paramethosone, fluocinolone, colchicine, acetaminophen, a non-steroidal anti-inflammatory agent NSAID, acyclovir, ribavarin, trifluorothyridine, Ara-A Arabinofuranosyladenine, acylguanosine, nordeoxyguanosine, azidothymidine, dideoxyadenosine, dideoxycytidine, spironolactone, testosterone, estradiol, progestin, gonadotrophin, estrogen, progesterone, papaverine, nitroglycerin, a vasoactive intestinal peptide, calcitonin gene-related peptide, cyproheptadine, doxepin, imipramine, cimetidine, dextromethorphan, clozaril, superoxide dismutase, neuroenkephalinase, amphotericin B, griseofulvin, miconazole, ketoconazole, tioconazol, itraconazole, fluconazole, cephalosporin, tetracycline, aminoglucoside, erythromicin, gentamicin, polymyxin B, 5-fluorouracil, bleomycin, methotrexate, hydroxyurea, dideoxyinosine, floxuridine, 6-mercaptopurine, doxorubicin, daunorubicin, I-darubicin, taxol, paclitaxel, tocopherol, quinidine, prazosin, verapamil, nifedipine, diltiazem, tissue plasminogen activator TPA, epidermal growth factor EGF, fibroblast growth factor FGF-acidic or basic, platelet derived growth factor PDGF, transforming growth factor TGF-alpha or beta, vasoactive intestinal peptide, tumor necrosis factor TNF, hypothalmic releasing factor, prolactin, thyroid stimulating hormone TSH, adrenocorticotropic hormone ACTH, parathyroid hormone PTH, follicle stimulating hormone FSF, luteinizing hormone releasing hormone LHRH, endorphin, glucagon, calcitonin, oxytocin, carbetocin, aldoetecone, enkaphalin, somatostin, somatotropin, somatomedin, alpha-melanocyte stimulating hormone, lidocaine, sufentainil, terbutaline, droperidol, scopolamine, gonadorelin, ciclopirox, buspirone, cromolyn sodium, midazolam, cyclosporin, lisinopril, captopril, delapril, ranitidine, famotidine, superoxide dismutase, asparaginase, arginase, argininne deaminease, adenosine deaminase ribonuclease, trypsin, chemotrypsin, papain, bombesin, substance P, vasopressin, alpha-globulins, transferrin, fibrinogen, beta-lipoprotein, beta-globulin, prothrombin, ceruloplasmin, alpha2-glycoprotein, alpha2-globulin, fetuin, alpha1-lipoprotein, alpha1-globulin, albumin, and prealbumin.

Examples of active agents include opioids or opioid antagonists, such as morphine, hydromorphone, oxymorphone, lovorphanol, levallorphan, codeine, nalmefene, nalorphine, nalozone, naltrexone, buprenorphine, butorphanol, and nalbufine; corticosterones, such as cortisone, hydrocortisone, fludrocortisone, prednisone, prednisolone, methylprednisolone, triamcinolone, dexamethoasone, betamethoasone, paramethosone, and fluocinolone; other anti-inflammatories, such as colchicine, ibuprofen, indomethacin, and piroxicam; anti-viral agents such as acyclovir, ribavarin, trifluorothyridine, Ara-A (Arabinofuranosyladenine), acylguanosine, nordeoxyguanosine, azidothymidine, dideoxyadenosine, and dideoxycytidine; antiandrogens such as spironolactone; androgens, such as testosterone; estrogens, such as estradiol; progestins; muscle relaxants, such as papaverine; vasodilators, such as nitroglycerin, vasoactive intestinal peptide and calcitonin related gene peptide; antihistamines, such as cyproheptadine; agents with histamine receptor site blocking activity, such as doxepin, imipramine, and cimetidine; antitussives, such as dextromethorphan; neuroleptics such as clozaril; antiarrhythmics; antiepileptics; enzymes, such as superoxide dismutase and neuroenkephalinase; anti-fungal agents, such as amphotericin B, griseofulvin, miconazole, ketoconazole, tioconazol, itraconazole, and fluconazole; antibacterials, such as penicillins, cephalosporins, tetracyclines, aminoglucosides, erythromicin, gentamicins, polymyxin B; anti-cancer agents, such as 5-fluorouracil, bleomycin, methotrexate, and hydroxyurea, dideoxyinosine, floxuridine, 6-mercaptopurine, doxorubicin, daunorubicin, I-darubicin, taxol, and paclitaxel; antioxidants, such as tocopherols, retinoids, carotenoids, ubiquinones, metal chelators, and phytic acid; antiarrhythmic agents, such as quinidine; antihypertensive agents such as prazosin, verapamil, nifedipine, and diltiazem; analgesics such as acetaminophen and aspirin; monoclonal and polyclonal antibodies, including humanized antibodies, and antibody fragments; anti-sense oligonucleotides; and RNA, regulatory RNA, interfering RNA, DNA, and viral vectors comprising genes encoding therapeutic peptides and proteins.

Compositions and Formulations for Administration

As used herein, the terms "administering" and "administration" encompass all means for directly and indirectly delivering a compound or composition to a site of action. The compounds and compositions of this disclosure may be administered alone, or in combination with other compounds, compositions, or therapeutic agents which are not disclosed herein.

The compositions and methods of the invention may be administered to subjects by a variety of mucosal administration modes, including by oral, rectal, vaginal, intranasal, intrapulmonary, or transdermal delivery, or by topical delivery to the eyes, ears, skin or other mucosal surfaces. In some aspects of this invention, the mucosal tissue layer includes an epithelial cell layer. The epithelial cell can be pulmonary, tracheal, bronchial, alveolar, nasal, buccal, epidermal, or gastrointestinal. Compositions of this invention can be administered using conventional actuators such as mechanical spray devices, as well as pressurized, electrically activated, or other types of actuators.

Compositions of this invention may be administered in an aqueous solution as a nasal or pulmonary spray and may be dispensed in spray form by a variety of methods known to those skilled in the art. Pulmonary delivery of a composition of this invention may be achieved by administering the composition in the form of drops, particles, or spray, which can be, for example, aerosolized, atomized, or nebulized. Pulmonary delivery may be performed by administering the composition in the form of drops, particles, or spray, via the nasal or bronchial passages. Particles of the composition, spray, or aerosol can be in a either liquid or solid form. Preferred systems for dispensing liquids as a nasal spray are disclosed in U.S. Pat. No. 4,511,069. Such formulations may be conveniently prepared by dissolving compositions according to the present invention in water to produce an aqueous solution, and rendering said solution sterile. The formulations may be presented in multi-dose containers, for example in the sealed dispensing system disclosed in U.S. Pat. No. 4,511,069. Other suitable nasal spray delivery systems have been described in *Transdermal Systemic Medication*, Y. W. Chien ed., Elsevier Publishers, New York, 1985; and in U.S. Pat. No. 4,778,810. Additional aerosol delivery forms may include, for example, compressed air-, jet-, ultrasonic-, and piezoelectric nebulizers, which deliver the biologically active agent dissolved or suspended in a pharmaceutical solvent, for example, water, ethanol, or mixtures thereof.

Nasal and pulmonary spray solutions of the present invention typically comprise the drug or drug to be delivered, optionally formulated with a surface active agent, such as a nonionic surfactant (e.g., polysorbate-80), and one or more buffers. In some embodiments of the present invention, the nasal spray solution further comprises a propellant. The pH of the nasal spray solution may be from about pH 6.8 to 7.2. The pharmaceutical solvents employed can also be a slightly acidic aqueous buffer of pH 4-6. Other components may be added to enhance or maintain chemical stability, including preservatives, surfactants, dispersants, or gases.

In some embodiments, this invention is a pharmaceutical product which includes a solution containing a composition of this invention and an actuator for a pulmonary, mucosal, or intranasal spray or aerosol.

A dosage form of the composition of this invention can be liquid, in the form of droplets or an emulsion, or in the form of an aerosol.

A dosage form of the composition of this invention can be solid, which can be reconstituted in a liquid prior to administration. The solid can be administered as a powder. The solid can be in the form of a capsule, tablet or gel.

To formulate compositions for pulmonary delivery within the present invention, the biologically active agent can be combined with various pharmaceutically acceptable additives or delivery-enhancing components, as well as a base or carrier for dispersion of the active agent(s). Examples of additives or delivery-enhancing components include pH control agents such as arginine, sodium hydroxide, glycine, hydrochloric acid, citric acid, and mixtures thereof. Other additives or delivery-enhancing components include local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione). When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the mucosa at the site of administration. Generally, the tonicity of the solution is adjusted to a value of about ⅓ to 3, more typically ½ to 2, and most often ¾ to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g., maleic anhydride) with other monomers (e.g., methyl (meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. A biodegradable polymer may be selected as a base or carrier, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters, etc., can be employed as carriers. Hydrophilic polymers and other carriers can be used alone or in combination, and enhanced structural integrity can be imparted to the carrier by partial crystallization, ionic bonding, cross-linking and the like. The carrier can be provided in a variety of forms, including, fluid or viscous solutions, gels, pastes, powders, microspheres and films for direct application to the nasal mucosa. The use of a selected carrier in this context may result in promotion of absorption of the biologically active agent.

The biologically active agent can be combined with the base or carrier according to a variety of methods, and release of the active agent may be by diffusion, disintegration of the carrier, or associated formulation of water channels. In some circumstances, the active agent is dispersed in microcapsules (microspheres) or nanocapsules (nanospheres) prepared from a suitable polymer, e.g., isobutyl 2-cyanoacrylate (see, e.g., Michael, et al., *J. Pharmacy Pharmacol.* 43:1-5, 1991), and dispersed in a biocompatible dispersing medium applied to the nasal mucosa, which yields sustained delivery and biological activity over a protracted time.

Formulations for mucosal, nasal, or pulmonary delivery may contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10,000 and preferably not more than 3000. Examples of hydrophilic low molecular weight compounds include polyol compounds, such as oligo-, di- and monosaccarides including sucrose, mannitol, lactose, L-arabinose, D-erythrose, D-ribose, D-xylose, D-mannose, D-galactose, lactulose, cellobiose, gentibiose, glycerin, polyethylene glycol, and mixtures thereof. Further examples of hydrophilic low molecular weight compounds include N-methylpyrrolidone, alcohols (e.g., oligovinyl alcohol, ethanol, ethylene glycol, propylene glycol, etc.), and mixtures thereof.

The compositions of this invention may alternatively contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the invention, the biologically active agent may be administered in a time release formulation, for example in a composition which includes a slow release polymer. The active agent can be prepared with carriers that will protect against rapid release, for example a controlled release vehicle such as a polymer, microencapsulated delivery system or bioadhesive gel. Prolonged delivery of the active agent, in various compositions of the invention can be brought about by including in the composition agents that delay absorption, for example, aluminum monosterate hydrogels and gelatin.

Within certain embodiments of this invention, a composition may contain one or more natural or synthetic surfactants. Certain natural surfactants are found in human lung (pulmonary surfactant), and are a complex mixture of phospholipids and proteins that form a monolayer at the alveolar air-liquid interface and reduces surface tension to near zero at expiration and prevents alveolar collapse. Over 90% (by weight) of pulmonary surfactant is composed of phospholipids with approximately 40-80% being DPPC and the remainder being unsaturated phosphatidylcholines POPG, POPC and phosphatidylglycerols. The remaining 10% (by weight) of surfactant is composed of plasma proteins and apoproteins, such as surface proteins (SP)-A, SP-B, SP-C and SP-D.

Examples of natural surfactants that may be used in this invention include SURVANTA™ (beractant), CUROSURF™ (poractant alfa) and INFASURF™ (calfactant), and mixtures thereof.

Examples of synthetic surfactants include sinapultide; a combination of dipalmitoylphosphatidylcholine, palmitoyloleoyl phosphatidylglycerol and palmitic acid; SURFAXIN™ (lucinactant); and EXOSURF™ (colfosceril); components which may contain tyloxapol, DPPC, and hexadecanol; and mixtures thereof.

Compositions of this invention can be prepared by methods known in the art. Methods of making the lipid compositions include ethanol injection methods and extrusion methods using a Northern Lipids Lipex Extruder system with stacked polycarbonate membrane filters of defined pore size. Sonication using probe tip and bath sonicators can be employed to produce lipid particles of uniform size. Homogenous and monodisperse particle sizes can be obtained without the addition of the nucleic acid component. For in vitro transfection compositions, the nucleic acid component can be added after the transfection agent is made and stabilized by additional buffer components. For in vivo delivery compositions, the nucleic acid component is part of the formulation.

The compositions and formulations of this invention may be administered by various routes, for example, to effect systemic delivery via intravenous, parenteral, or intraperitoneal routes. In some embodiments, an agent may be delivered intracellularly, for example, in cells of a target tissue such as lung or liver, or in inflamed tissues. Included within this disclosure are compositions and methods for delivery of an agent by removing cells of a subject, delivering an agent to the removed cells, and reintroducing the cells into a subject.

In some embodiments, this invention provides a method for delivery of an agent in vivo. A composition may be administered intravenously, subcutaneously, or intraperitoneally to a subject. In some embodiments, the invention provides methods for in vivo delivery of an agent to the lung of a mammalian subject.

Additional Embodiments

All publications, references, patents, patent publications and patent applications cited herein are each hereby specifically incorporated by reference in entirety.

While this invention has been described in relation to certain embodiments, and many details have been set forth for purposes of illustration, it will be apparent to those skilled in the art that this invention includes additional embodiments, and that some of the details described herein may be varied considerably without departing from this invention. This invention includes such additional embodiments, modifications and equivalents. In particular, this invention includes any combination of the features, terms, or elements of the various illustrative components and examples.

The use herein of the terms "a," "an," "the" and similar terms in describing the invention, and in the claims, are to be construed to include both the singular and the plural.

The terms "comprising," "having," "including" and "containing" are to be construed as open-ended terms which mean, for example, "including, but not limited to." Thus, terms such as "comprising," "having," "including" and "containing" are to be construed as being inclusive, not exclusive.

Recitation of a range of values herein refers individually to each and any separate value falling within the range as if it were individually recited herein, whether or not some of the values within the range are expressly recited. For example, the range "4 to 12" includes without limitation the values 5, 5.1, 5.35 and any other whole, integer, fractional, or rational value greater than or equal to 4 and less than or equal to 12. Specific values employed herein will be understood as exemplary and not to limit the scope of the invention.

Recitation of a range of number of carbon atoms herein refers individually to each and any separate value falling within the range as if it were individually recited herein, whether or not some of the values within the range are expressly recited. For example, the term "C1-22" includes without limitation the species C1, C2, C3, C4, C5, C6, C7, C8, C9, C10, C11, C12, C13, C14, C15, C16, C17, C18, C19, C20, C21, and C22.

Definitions of technical terms provided herein should be construed to include without recitation those meanings associated with these terms known to those skilled in the art, and are not intended to limit the scope of the invention. Definitions of technical terms provided herein shall be construed to dominate over alternative definitions in the art or definitions which become incorporated herein by reference to the extent that the alternative definitions conflict with the definition provided herein.

The examples given herein, and the exemplary language used herein are solely for the purpose of illustration, and are not intended to limit the scope of the invention.

When a list of examples is given, such as a list of compounds or molecules suitable for this invention, it will be apparent to those skilled in the art that mixtures of the listed compounds or molecules are also suitable.

EXAMPLES

Example 1

Preparation of C10-Arg-C10

N-(5-guanidino-1-oxo-1-(decylamino)pentan-2-yl) decanamide

Fmoc-Arg(Pbf)-resin. To 3 g of 2-chlorotrityl chloride resin with 1.3 mmol/g substitution (Novabiochem, (01-64-0114) in 30 ml of dry DCM in 30 ml reaction vessel for solid phase synthesis, 5.06 g (11.7 mmol, 3 eq) of Fmoc-Arg(Pbf)-OH (Mw=648.8, Novabiochem, 04-12-1145) and 2.23 ml (12.87 mmol, 3.3 eq) of DIPEA (Aldrich, Mw=129.2, d=0.74) were added.

Arg(Pbf)-resin. After 2 hrs the resin was washed 3× with DCM/MeOH/DIPEA (17:2:1), 3×DCM, 2×DMF, 3×DCM and Fmoc group was deprotected with 30 ml of 20% piperidine/DMF for 30 min.

C10-Arg(Pbf)-resin. After Fmoc deprotection the resin was washed with 3×DCM, 2×MeOH and 3×DCM and for the coupling reaction 1.48 g (11.7 mmol) of decanoic acid (Sigma, Mw=127.27), 5.54 g (11.7 mmol) of HCTU (Mw=473.7) and 2.23 ml (12.87 mmol) of DIPEA (Mw=129.2, d=0.74) in 30 ml of DMF were added.

After 1 hr of reaction the resin was washed with 3×DCM, 2×MeOH and 3×DCM and progress of reaction was checked by Kaiser test which was negative (no free amine groups present).

C10-Arg(Pbf)-OH (Mw=580.83) was cleaved from the resin by 1% TFA/DCM (5×30 ml for 2 min was filtered to flask with 2 ml 10% pyridine/MeOH) and solvent was evaporated.

C10-Arg(Pbf)-C10 (Mw=720.13). Second coupling was carried out in solution. To the oily residue from the previous reaction 2.32 ml (11.7 mmol) of C10-amine (Sigma, Mw=157.3, d=0.792), 5.54 g (11.7 mmol) of HCTU (Mw=473.7) and 2.23 ml (12.87 mmol) of DIPEA (Mw=129.2, d=0.74) in 50 ml of DMF were added. After 1 hr 100 ml of AcOEt was added and organic layer was washed in separatory funnel with 3×0.5 M HCl, 3×10% NaCO3 and 3×NaCl. AcOEt layer was dried with anhydrous MgSO$_4$ and evaporated.

C10-Arg-C10 (Mw=467.8) To the oily residue from the previous reaction 100 ml of 95% TFA/DCM 2.5% TIS was added and after 3 hrs solvent was evaporated. Residue was dissolved in AcCN/0.5 M HCl 1:1 and purified by RP_Akta Explorer on C18 Phenomenex column (Phenomenex RP, 250×21.2 mm, Serial No.: 234236-1, Column volume 83 ml) and eluted with 0-100% acetonitrile gradient using water as mobile phase within 3 CV; λ=215 nm. Acetonitrile was evaporated and the product was lyophilized.

Example 2

Preparation of C10-D-Arg-C10

N-(5-guanidino-1-oxo-1-(decylamino)pentan-2-yl) decanamide

Fmoc-D-Arg(Pmc)-resin. To 3 g of 2-chlorotrityl chloride resin with 1.3 mmol/g substitution (Novabiochem, (01-64-0114) in 30 ml of dry DCM in 30 ml reaction vessel for solid phase synthesis, 5.06 g (11.7 mmol, 3 eq) of Fmoc-D-Arg(Pmc)-OH ($M_w$=662.8, Novabiochem, 04-12-1145) and 2.23 ml (12.87 mmol, 3.3 eq) of DIPEA (Aldrich, $M_w$=129.2, d=0.74) were added.

D-Arg(Pmc)-resin. After 2 hrs the resin was washed 3× with DCM/MeOH/DIPEA (17:2:1), 3×DCM, 2×DMF, 3×DCM and Fmoc group was deprotected with 30 ml of 20% piperidine/DMF for 30 min.

C10-D-Arg(Pmc)-resin. After Fmoc deprotection the resin was washed with 3×DCM, 2×MeOH and 3×DCM and for the coupling reaction 1.48 g (11.7 mmol) of decanoic acid (Sigma, $M_w$=127.27), 5.54 g (11.7 mmol) of HCTU ($M_w$=473.7) and 2.23 ml (12.87 mmol) of DIPEA ($M_w$=129.2, d=0.74) in 30 ml of DMF were added.

After 1 hr of reaction the resin was washed with 3×DCM, 2×MeOH and 3×DCM and progress of reaction was checked by Kaiser test which was negative (no free amine groups present).

C10-D-Arg(Pmc)-OH ($M_w$=591.84) was cleaved from the resin by 1% TFA/DCM (5×30 ml for 2 min was filtered to flask with 2 ml 10% pyridine/MeOH) and solvent was evaporated.

C10-D-Arg(Pmc)-C10 ($M_w$=732.14). Second coupling was carried out in solution. To the oily residue from the previous reaction 2.32 ml (11.7 mmol) of C10-amine (Sigma, $M_w$=157.3, d=0.792), 5.54 g (11.7 mmol) of HCTU ($M_w$=473.7) and 2.23 ml (12.87 mmol) of DIPEA ($M_w$=129.2, d=0.74) in 50 ml of DMF were added. After 1 hr 100 ml of AcOEt was added and organic layer was washed in separatory funnel with 3×0.5 M HCl, 3×10% NaCO$_3$ and 3×NaCl. AcOEt layer was dried with anhydrous MgSO$_4$ and evaporated.

C10-D-Arg-C10 ($M_w$=467.8) To the oily residue from the previous reaction 100 ml of 95% TFA/DCM 2.5% TIS was added and after 3 hrs solvent was evaporated. Residue was dissolved in AcCN/0.5 M HCl 1:1 and purified by RP_Akta Explorer on C18 Phenomenex column (Phenomenex RP, 250×21.2 mm, Serial No.: 234236-1, Column volume 83 ml) and eluted with 0-100% acetonitrile gradient using water as mobile phase within 3 CV; λ=215 nm. Acetonitrile was evaporated and the product was lyophilized.

Example 3

Preparation of C12-Arg-C12

N-(5-guanidino-1-oxo-1-(dodecylamino)pentan-2-yl) dodecanamide

Fmoc-Arg(Pbf)-resin. To 5 g of 2-chlorotrityl chloride resin with 1.3 mmol/g substitution (Novabiochem, (01-64-0114) in 50 ml of dry DCM in 200 ml reaction vessel for solid phase synthesis, 8.434 g (13 mmol, 2 eq) of Fmoc- Arg(Pbf)-OH ($M_w$=648.8, Novabiochem, 04-12-1145) and 2.26 ml (13 mmol, 2 eq) of DIPEA (Aldrich, $M_w$=129.2, d=0.74) were added.

Arg(Pbf)-resin. After 2 hrs the resin was washed 3× with DCM/MeOH/DIPEA (17:2:1), 3×DCM, 2×DMF, 3×DCM and Fmoc group was deprotected 2× with 50 ml of 20% piperidine/DMF for 15 min.

C12-Arg(Pbf)-resin. After Fmoc deprotection the resin was washed with 3×DCM, 2×MeOH and 3×DCM and for the coupling reaction 1.95 g (9.75 mmol) of dodecanoic acid (Sigma, $M_w$=200.32), 4.033 (9.75 mmol) of HCTU ($M_w$=417.7) and 1.7 ml (9.75 mmol) of DIPEA ($M_w$=129.2, d=0.74) in 50 ml of DMF were added.

After 1 hr of reaction the resin was washed with 3×DCM, 2×MeOH and 3×DCM and progress of reaction was checked by Kaiser test which was negative (no free amine groups present).

C12-Arg(Pbf)-OH ($M_w$=608.9) was cleaved from the resin by 1% TFA/DCM (5×30 ml for 2 min was filtered to flask with 2 ml 10% pyridine/MeOH) and solvent was evaporated.

C12-Arg(Pbf)-C12 ($M_w$=776.13). Second coupling was carried out in solution. To the oily residue from the previous step 1.246 g (6.5 mmol) of EDC*HCl ($M_w$=191.7), 1.06 g (7.15 mmol, 1.1 eq) of HOBt*$H_2O$ ($M_w$=153), and 5.65 ml (31.5 mmol, 5 eq) of DIPEA ($M_w$=129.2, d=0.74) in 50 ml of DCM were added to preactivate —COOH followed by 1.32 g (7.15 mmol) of C12-amine (Sigma, $M_w$=185.36) 20 min later. After 1 hr 100 ml of AcOEt was added and organic layer was washed in separatory funnel with 3×0.5 M HCl, 3×10% $NaCO_3$ and 3×NaCl. AcOEt layer was dried with anhydrous $MgSO_4$ and evaporated. The product was purified on TELEDYNE Isco CombiFlash $R_f$ instrument, 40 g normal phase silica gel column, 100% DCM for 5 CV (column volume) and 0-5% MeOH for 10 CV, detection 254 nm, flow 40 ml/min.

C12-Arg-C12 ($M_w$=523.8) To the oily residue from the previous reaction 50 ml of 85% TFA/DCM 2.5% TIS was added and after 3 hrs solvent was evaporated. The product was precipitated with 0.5 M HCl.

Example 4

Preparation of C12-Arg-C14

N-(5-guanidino-1-oxo-1-(tetradecylamino)pentan-2-yl)dodecanamide

Fmoc-Arg(Pbf)-resin. To 5 g of 2-chlorotrityl chloride resin with 1.3 mmol/g substitution (Novabiochem, (01-64-0114) in 50 ml of dry DCM in 200 ml reaction vessel for solid phase synthesis, 8.434 g (13 mmol, 2 eq) of Fmoc-Arg(Pbf)-OH ($M_w$=648.8, Novabiochem, 04-12-1145) and 2.26 ml (13 mmol, 2 eq) of DIPEA (Aldrich, $M_w$=129.2, d=0.74) were added.

Arg(Pbf)-resin. After 2 hrs the resin was washed 3× with DCM/MeOH/DIPEA (17:2:1), 3×DCM, 2×DMF, 3×DCM and Fmoc group was deprotected 2* with 50 ml of 20% piperidine/DMF for 15 min.

C12-Arg(Pbf)-resin. After Fmoc deprotection the resin was washed with 3×DCM, 2×MeOH and 3×DCM and for the coupling reaction 1.95 g (9.75 mmol) of dodecanoic acid (Sigma, $M_w$=200.32), 4.033 (9.75 mmol) of HCTU ($M_w$=417.7) and 1.7 ml (9.75 mmol) of DIPEA ($M_w$=129.2, d=0.74) in 50 ml of DMF were added.

After 1 hr of reaction the resin was washed with 3×DCM, 2×MeOH and 3×DCM and progress of reaction was checked by Kaiser test which was negative (no free amine groups present).

C12-Arg(Pbf)-OH ($M_w$=608.9) was cleaved from the resin by 1% TFA/DCM (5×30 ml for 2 min was filtered to flask with 2 ml 10% pyridine/MeOH) and solvent was evaporated.

C12-Arg(Pbf)-C14 ($M_w$=804.13). Second coupling was carried out in solution. To the oily residue from the previous step 1.246 g (6.5 mmol) of EDC*HCl ($M_w$=191.7), 1.06 g (7.15 mmol, 1.1 eq) of HOBt*$H_2O$ ($M_w$=153), and 5.65 ml (31.5 mmol, 5 eq) of DIPEA ($M_w$=129.2, d=0.74) in 50 ml of DCM were added to preactivate —COOH followed by 1.52 g (7.15 mmol) of C14-amine (Sigma, $M_w$=213.41) 20 min later. After 1 hr 100 ml of AcOEt was added and organic layer was washed in separatory funnel with 3×0.5 M HCl, 3×10% $NaCO_3$ and 3×NaCl. AcOEt layer was dried with anhydrous $MgSO_4$ and evaporated. The product was purified on TELEDYNE Isco CombiFlash $R_f$ instrument, 40 g normal phase silica gel column, 100% DCM for 5 CV (column volume) and 0-5% MeOH for 10 CV, detection 254 nm, flow 40 ml/min.

C12-Arg-C14 ($M_w$=551.8) To the oily residue from the previous reaction 50 ml of 85% TFA/DCM 2.5% TIS was added and after 3 hrs solvent was evaporated. The product was precipitated with 0.5 M HCl.

Example 5

In like fashion to Examples 1-4 were made C14-Arg-C14 (Yield: 1.6 g), C16-Arg-C16, and C18-Arg-C18.

Example 6

Preparation of C18(oleic)-Arg-C16

N-(5-guanidino-1-oxo-1-(hexadecylamino)pentan-2-yl)octadec-9-enamide

Fmoc-Arg(Pbf)-resin. To 5 g of 2-chlorotrityl chloride resin with 1.3 mmol/g substitution (Novabiochem, (01-64-0114) in 50 ml of dry DCM in 60 ml reaction vessel for solid phase synthesis, 8.4 g (13 mmol, 2 eq) of Fmoc-Arg(Pbf)-OH ($M_w$=648.8, Novabiochem, 04-12-1145) and 2.26 ml (13 mmol, 2 eq) of DIPEA (Aldrich, $M_w$=129.2, d=0.74) were added.

Arg(Pbf)-resin. After 2 hrs the resin was washed 3× with DCM/MeOH/DIPEA (17:2:1), 3×DCM, 2×DMF, 3×DCM and Fmoc group was deprotected 2 times with 50 ml of 20% piperidine/DMF for 15 min.

$C18_{oleic}$-Arg(Pbf)-resin. After Fmoc deprotection the resin was washed with 3×DCM, 2×MeOH and 3×DCM and for the coupling reaction 3.1 ml (9.75 mmol) of oleic acid (Sigma, $M_w$=282.47; d=0.891), 4 g (9.75 mmol) of HCTU ($M_w$=413.7) and 1.7 ml (9.75 mmol) of DIPEA ($M_w$=129.2, d=0.74) in 50 ml of DMF were added.

After 1 hr of reaction the resin was washed with 3×DCM, 2×MeOH and 3×DCM and progress of reaction was checked by Kaiser test which was negative (no free amine groups present).

$C18_{oleic}$-Arg(Pbf)-OH ($M_w$=690.83) was cleaved from the resin by 1% TFA/DCM (5×50 ml for 2 min was filtered to flask with 2 ml 10% pyridine/MeOH) and solvent was evaporated.

$C18_{oleic}$-Arg(Pbf)-C16 ($M_w$=850.13). Second coupling was carried out in solution. To the oily residue from the previous step 1.437 g (7.5 mmol) of EDC*HCl ($M_w$=191.7), 1.178 g (7.7 mmol) of HOBt*$H_2O$ ($M_w$=153), and 6.5 ml (37.5 mmol, 5 eq) of DIPEA ($M_w$=129.2, d=0.74) in 50 ml of DCM were added to preactivate —COOH followed by addition of 1.86 g (7.7 mmol) of C16-amine (Sigma, $M_w$=241.46) 20 min later. After overnight reaction organic layer was washed in separatory funnel with 3×0.5 M HCl, 3×10% $NaCO_3$ and 3×NaCl. DCM layer was dried with anhydrous $MgSO_4$ and evaporated. The product was purified on TELEDYNE Isco CombiFlash $R_f$ instrument, 40 g normal phase silica gel column, 100% DCM for 5 CV (column volume) and 0-5% MeOH for 10 CV, detection 215 nm, flow 40 ml/min.

$C18_{oleic}$-Arg-C16 ($M_w$=661.8) To the oily residue from the previous reaction, 100 ml of 95% TFA/DCM 2.5% TIS was added and after 3 hrs solvent was evaporated. Product was precipitated with 0.5 M HCl and repurified. Yield: 1.8 g.

Example 7

Preparation of C8-homoArg-C8

N-(6-guanidino-1-oxo-1-(octylamino)hexan-2-yl) octanamide

Fmoc-hArg(diBoc)-resin. To 3 g of 2-chlorotrityl chloride resin with 1.3 mmol/g substitution (Novabiochem, (01-64-0114) in 30 ml of dry DCM in 30 ml reaction vessel for solid phase synthesis, 3.57 g (5.85 mmol, 1.5 eq) of Fmoc-hArg (diBoc)-OH ($M_w$=610.69, Novabiochem) and 2.04 ml (11.7 mmol, 3.0 eq) of DIPEA (Aldrich, $M_w$=129.2, d=0.74) were added.

hArg(diBoc)-resin. After 2 hrs the resin was washed 3× with DCM/MeOH/DIPEA (17:2:1), 3×DCM, 2×DMF, 3×DCM and Fmoc group was deprotected with 30 ml of 20% piperidine/DMF for 30 min.

C8-hArg(diBoc)-resin. After Fmoc deprotection the resin was washed with 3×DCM, 2×MeOH and 3×DCM and for the coupling reaction 1.854 ml (11.7 mmol) of C8 acid (Sigma, $M_w$=144.22, d=0.91), 4.84 g (11.7 mmol) of HCTU ($M_w$=413.7) and 2.23 ml (12.87 mmol) of DIPEA ($M_w$=129.2, d=0.74) in 30 ml of DMF were added.

After 1 hr of reaction the resin was washed with 3×DCM, 2×MeOH and 3×DCM and progress of reaction was checked by Kaiser test which was negative (no free amine groups present).

C8-hArg(diBoc)-OH ($M_w$=514.68) was cleaved from the resin by 1% TFA/DCM (5×30 ml for 2 min was filtered to flask with 2 ml 10% pyridine/MeOH) and solvent was evaporated.

C8-hArg(diBoc)-C8 ($M_w$=625.93). Second coupling was carried out in solution. To the oily residue from the previous reaction 1.93 ml (11.7 mmol) of C8-amine (Sigma, $M_w$=129.25, d=0.782), 4.84 g (11.7 mmol) of HCTU ($M_w$=473.7) and 2.23 ml (12.87 mmol) of DIPEA ($M_w$=129.2, d=0.74) in 50 ml of DMF were added. After 1 hr 100 ml of AcOEt was added and organic layer was washed in separatory funnel with 3×0.5 M HCl, 3×10% $NaCO_3$ and 3×NaCl. AcOEt layer was dried with anhydrous $MgSO_4$ and evaporated.

C8-hArg-C8 ($M_w$=426.8) To the oily residue from the previous reaction 100 ml of 95% TFA/DCM 2.5% TIS was added and after 1 hr solvent was evaporated. Residue was dissolved in MeOH/AcCN/0.5 M HCl 1:1:1 and purified by RP_Akta Explorer on C18 Phenomenex column (Phenomenex RP, 250×21.2 mm, Serial No.: 234236-1, Column volume 83 ml) and eluted with 50-100% acetonitrile gradient using water as mobile phase within 3 CV; λ=215 nm. Acetonitrile was evaporated and the product was lyophilized.

Example 8

Preparation of C10-homoArg-C10

N-(6-guanidino-1-oxo-1-(decylamino)hexan-2-yl) decanamide

Fmoc-hArg(diBoc)-resin. To 3 g of 2-chlorotrityl chloride resin with 1.3 mmol/g substitution (Novabiochem, (01-64-0114) in 30 ml of dry DCM in 30 ml reaction vessel for solid phase synthesis, 3.57 g (5.85 mmol, 1.5 eq) of Fmoc-hArg (diBoc)-OH ($M_w$=610.69, Novabiochem) and 2.04 ml (11.7 mmol, 3.0 eq) of DIPEA (Aldrich, $M_w$=129.2, d=0.74) were added.

hArg(diBoc)-resin. After 2 hrs the resin was washed 3× with DCM/MeOH/DIPEA (17:2:1), 3×DCM, 2×DMF, 3×DCM and Fmoc group was deprotected with 30 ml of 20% piperidine/DMF for 30 min.

C10-hArg(diBoc)-resin. After Fmoc deprotection the resin was washed with 3×DCM, 2×MeOH and 3×DCM and for the coupling reaction 1.48 g (11.7 mmol) of decanoic acid (Sigma, $M_w$=127.27), 5.54 g (11.7 mmol) of HCTU ($M_w$=473.7) and 2.23 ml (12.87 mmol) of DIPEA ($M_w$=129.2, d=0.74) in 30 ml of DMF were added.

After 1 hr of reaction the resin was washed with 3×DCM, 2×MeOH and 3×DCM and progress of reaction was checked by Kaiser test which was negative (no free amine groups present).

C10-hArg(diBoc)-OH ($M_w$=541.78) was cleaved from the resin by 1% TFA/DCM (5×30 ml for 2 min was filtered to flask with 2 ml 10% pyridine/MeOH) and solvent was evaporated.

C10-hArg(diBoc)-C10 ($M_w$=682.08). Second coupling was carried out in solution. To the oily residue from the previous reaction 2.32 ml (11.7 mmol) of C10-amine (Sigma, $M_w$=157.3, d=0.792), 5.54 g (11.7 mmol) of HCTU ($M_w$=473.7) and 2.23 ml (12.87 mmol) of DIPEA ($M_w$=129.2, d=0.74) in 50 ml of DMF were added. After 1 hr 100 ml of AcOEt was added and organic layer was washed in separatory funnel with 3×0.5 M HCl, 3×10% $NaCO_3$ and 3×NaCl. AcOEt layer was dried with anhydrous $MgSO_4$ and evaporated.

C10-hArg-C10 ($M_w$=481.8) To the oily residue from the previous reaction 100 ml of 95% TFA/DCM 2.5% TIS was added and after 1 hr solvent was evaporated. Residue was dissolved in MeOH/0.5 M HCl 1:1 and precipitated with $H_2O$.

Example 9

Preparation of C12-homoArg-C12

N-(6-guanidino-1-oxo-1-(dodecylamino)hexan-2-yl) dodecanamide

In like fashion to Example 8 was made C12-homoArg-C12 (Yield: 1 g).

Example 10

Preparation of C8-nor-norArg-C8

N-(3-guanidino-1-oxo-1-(octylamino)propan-2-yl)octanamide

Fmoc-Dap(Boc)-resin. To 3 g of 2-chlorotrityl chloride resin with 1.3 mmol/g substitution (Novabiochem, (01-64-0114) in 30 ml of dry DCM in 30 ml reaction vessel for solid phase synthesis, 2.5 g (5.85 mmol, 1.5 eq) of Fmoc-Dap (Boc)-OH ($M_w$=426.5, (Fmoc-(N-β-Boc)-L-α,β-diaminopropionic acid), AnaSpec, 22140) and 2.03 ml (11.7 mmol, 3.0 eq) of DIPEA (Aldrich, $M_w$=129.2, d=0.74) were added.

Dap-(Boc)-resin. After 2 hrs the resin was washed 3× with DCM/MeOH/DIPEA (17:2:1), 3×DCM, 2×DMF, 3×DCM and Fmoc group was deprotected with 30 ml of 20% piperidine/DMF for 30 min.

C8-Dap(Boc)-resin. After Fmoc deprotection the resin was washed with 3×DCM, 2×MeOH and 3×DCM and for the coupling reaction 1.236 ml (11.7 mmol) of C8 acid (Sigma, $M_w$=144.22, d=0.910), 4.84 g (11.7 mmol) of HCTU ($M_w$=413.7) and 2.23 ml (12.87 mmol) of DIPEA ($M_w$=129.2, d=0.74) in 30 ml of DMF were added.

After 1 hr of reaction the resin was washed with 3×DCM, 2×MeOH and 3×DCM and progress of reaction was checked by Kaiser test which was negative (no free amine groups present).

C8-Dap(Boc)-OH ($M_w$=330.49) was cleaved from the resin by 1% TFA/DCM (5×30 ml for 2 min was filtered to flask with 2 ml 10% pyridine/MeOH) and solvent was evaporated.

C8-Dap(Boc)-C8 ($M_w$=441.74). Second coupling was carried out in solution. To the oily residue from the previous reaction 2.32 ml (11.7 mmol) of C8-amine (Sigma, $M_w$=129.25, d=0.782), 4.84 g (11.7 mmol) of HCTU ($M_w$=473.7) and 2.23 ml (12.87 mmol) of DIPEA ($M_w$=129.2, d=0.74) in 50 ml of DMF were added. After 1 hr 100 ml of AcOEt was added and organic layer was washed in separatory funnel with 3×0.5 M HCl, 3×10% NaCO$_3$ and 3×NaCl. AcOEt layer was dried with anhydrous MgSO$_4$ and evaporated.

C8-Dap-C8 ($M_w$=341.74). To the oily residue from the previous reaction, 100 ml of 80% TFA/DCM 2.5% TIS was added and after 1 hr solvent was evaporated.

C8-nor-norArg(diBoc)-C8 ($M_w$=583.74). The residue was dissolved in 50 ml of DCM and pH was adjusted to 9 with TEA. 2.23 g (5.85 mM, 1.5 eq) of 1,3-Di-Boc-2-(trifluoromethylsulfonyl)guanidine ($M_w$=391.36, Aldrich 15033) was added and after 4 hrs DCM was evaporated.

C8-nor-norArg-C8 ($M_w$=384.8) To the oily residue from the previous reaction 100 ml of 95% TFA/DCM 2.5% TIS was added and after 3 hrs solvent was evaporated. Residue was dissolved in MeOH/AcCN/0.5 M HCl 1:1:1 and purified by RP_Akta Explorer on C18 Phenomenex column (Phenomenex RP, 250×21.2 mm, Serial No.: 234236-1, Column volume 83 ml) and eluted with 50-100% acetonitrile gradient using water as mobile phase within 3 CV; λ=215 nm. Acetonitrile was evaporated and the product was lyophilized.

Example 11

Preparation of C10-nor-norArg-C10

N-(3-guanidino-1-oxo-1-(decylamino)propan-2-yl)decanamide

Fmoc-Dap(Boc)-resin. To 3 g of 2-chlorotrityl chloride resin with 1.3 mmol/g substitution (Novabiochem, (01-64-0114) in 30 ml of dry DCM in 30 ml reaction vessel for solid phase synthesis, 2.5 g (5.85 mmol, 1.5 eq) of Fmoc-Dap (Boc)-OH ($M_w$=426.5, (Fmoc-(N-β-Boc)-L-α,β-diaminopropionic acid), AnaSpec, 22140) and 2.03 ml (11.7 mmol, 3.0 eq) of DIPEA (Aldrich, $M_w$=129.2, d=0.74) were added.

Dap(Boc)-resin. After 2 hrs the resin was washed 3× with DCM/MeOH/DIPEA (17:2:1), 3×DCM, 2×DMF, 3×DCM and Fmoc group was deprotected with 30 ml of 20% piperidine/DMF for 30 min.

C10-Dap(Boc)-resin. After Fmoc deprotection the resin was washed with 3×DCM, 2×MeOH and 3×DCM and for the coupling reaction 1.48 g (11.7 mmol) of decanoic acid (Sigma, $M_w$=172.27), 4.83 g (11.7 mmol) of HCTU ($M_w$=413.7) and 2.23 ml (12.87 mmol) of DIPEA ($M_w$=129.2, d=0.74) in 30 ml of DMF were added.

After 1 hr of reaction the resin was washed with 3×DCM, 2×MeOH and 3×DCM and progress of reaction was checked by Kaiser test which was negative (no free amine groups present).

C10-Dap(Boc)-OH ($M_w$=357.54) was cleaved from the resin by 1% TFA/DCM (5×30 ml for 2 min was filtered to flask with 2 ml 10% pyridine/MeOH) and solvent was evaporated.

C10-Dap(Boc)-C10 ($M_w$=496.84). Second coupling was carried out in solution. To the oily residue from the previous reaction 2.32 ml (11.7 mmol) of C10-amine (Sigma, $M_w$=157.3, d=0.792), 4.83 g (11.7 mmol) of HCTU ($M_w$=473.7) and 2.23 ml (12.87 mmol) of DIPEA ($M_w$=129.2, d=0.74) in 50 ml of DMF were added. After 2 hr 100 ml of AcOEt was added and organic layer was washed in separatory funnel with 3×0.5 M HCl, 3×10% NaCO$_3$ and 3×NaCl. AcOEt layer was dried with anhydrous MgSO$_4$ and evaporated.

C10-Dap-C10 ($M_w$=397.8). To the oily residue from the previous reaction, 100 ml of 80% TFA/DCM 2.5% TIS was added and after 1 hr solvent was evaporated.

C10-nor-norArg(diBoc)-C10 ($M_w$=640.8). The residue was dissolved in 50 ml of DCM and pH was adjusted to 9 with TEA. 2.23 g (5.85 mM, 1.5 eq) of 1,3-Di-Boc-2-(trifluoromethylsulfonyl)guanidine ($M_w$=391.36, Aldrich 15033) was added and after 4 hrs DCM was evaporated.

C10-nor-norArg-C10 ($M_w$=439.8) To the oily residue from the previous reaction, 100 ml of 80% TFA/DCM 2.5% TIS was added and after 1 hr solvent was evaporated. Residue was dissolved in AcCN/MeOH/0.5 M HCl 1:1:1 and purified by RP_Akta Explorer on C18 Phenomenex column (Phenomenex RP, 250×21.2 mm, Serial No.: 234236-1, Column volume 83 ml) and eluted with 50-100% acetonitrile gradient using water as mobile phase within 3 CV; λ=215 nm. Acetonitrile was evaporated and the product was lyophilized. Yield: 1.6 g.

Example 12

Preparation of C12-nor-norArg-C12

N-(3-guanidino-1-oxo-1-(dodecylamino)propan-2-yl)dodecanamide

Fmoc-Dap(Boc)-resin. To 3 g of 2-chlorotrityl chloride resin with 1.3 mmol/g substitution (Novabiochem, (01-64-0114) in 30 ml of dry DCM in 30 ml reaction vessel for solid phase synthesis, 2.5 g (5.85 mmol, 1.5 eq) of Fmoc-Dap (Boc)-OH ($M_w$=426.5, (Fmoc-(N-β-Boc)-L-α,β-diaminopropionic acid), AnaSpec, 22140) and 2.03 ml (11.7 mmol, 3.0 eq) of DIPEA (Aldrich, $M_w$=129.2, d=0.74) were added.

Dap(Boc)-resin. After 2 hrs the resin was washed 3× with DCM/MeOH/DIPEA (17:2:1), 3×DCM, 2×DMF, 3×DCM and Fmoc group was deprotected with 30 ml of 20% piperidine/DMF for 30 min.

C12-Dap(Boc)-resin. After Fmoc deprotection the resin was washed with 3×DCM, 2×MeOH and 3×DCM and for the coupling reaction 2.34 g (11.7 mmol) of C12-acid (Sigma, $M_w$=200.32), 4.48 g (11.7 mmol) of HCTU ($M_w$=473.7) and 2.23 ml (12.87 mmol) of DIPEA ($M_w$=129.2, d=0.74) in 30 ml of DMF were added.

After 1 hr of reaction the resin was washed with 3×DCM, 2×MeOH and 3×DCM and progress of reaction was checked by Kaiser test which was negative (no free amine groups present).

C12-Dap(Boc)-OH ($M_w$=386.59) was cleaved from the resin by 1% TFA/DCM (5×30 ml for 2 min was filtered to flask with 2 ml 10% pyridine/MeOH) and solvent was evaporated.

C12-Dap(Boc)-C12 ($M_w$=553.95). Second coupling was carried out in solution. To the oily residue from the previous reaction 2.168 g (11.7 mmol) of C12-amine (Sigma, $M_w$=185.36), 4.48 g (11.7 mmol) of HCTU ($M_w$=473.7) and 2.23 ml (12.87 mmol) of DIPEA ($M_w$=129.2, d=0.74) in 50 ml of DMF were added. After 1 hr 100 ml of AcOEt was added and organic layer was washed in separatory funnel with 3×0.5 M HCl, 3×10% NaCO$_3$ and 3×NaCl. AcOEt layer was dried with anhydrous MgSO$_4$ and evaporated.

C12-Dap-C12 ($M_w$=453.9). To the oily residue from the previous reaction, 100 ml of 80% TFA/DCM 2.5% TIS was added and after 1 hr solvent was evaporated.

C12-nor-norArg(diBoc)-C12 ($M_w$=696.13). The residue was dissolved in 50 ml of DCM and pH was adjusted to 9 with TEA. 2.23 g (5.85 mM, 1.5 eq) of 1,3-Di-Boc-2-(trifluoromethylsulfonyl) guanidine ($M_w$=391.36, Aldrich 15033) was added and after 4 hrs DCM was evaporated.

Example 13

Preparation of C8-norArg-C8

N-(4-guanidino-1-oxo-1-(octylamino)butan-2-yl) octanamide

Fmoc-Dab(Boc)-resin. To 3 g of 2-chlorotrityl chloride resin with 1.3 mmol/g substitution (Novabiochem, (01-64-0114) in 30 ml of dry DCM in 30 ml reaction vessel for solid phase synthesis, 2.577 g (5.85 mmol, 1.5 eq) of Fmoc-Dab(diBoc)-OH ($M_w$=440.5, (Fmoc-(N-γ-Boc)-L-α,γ-diaminobutyric acid, AnaSpec, 28246) and 2.23 ml (12.87 mmol, 3.3 eq) of DIPEA (Aldrich, $M_w$=129.2, d=0.74) were added.

Arg-Dab(Boc)-resin. After 2 hrs the resin was washed 3× with DCM/MeOH/DIPEA (17:2:1), 3×DCM, 2×DMF, 3×DCM and Fmoc group was deprotected with 30 ml of 20% piperidine/DMF for 30 min.

C8-Dab(Boc)-resin. After Fmoc deprotection the resin was washed with 3×DCM, 2×MeOH and 3×DCM and for the coupling reaction 1.48 g (11.7 mmol) of C8 acid (Sigma, $M_w$=144.22, d=0.910), 4.84 g (11.7 mmol) of HCTU ($M_w$=413.7) and 2.23 ml (12.87 mmol) of DIPEA ($M_w$=129.2, d=0.74) in 30 ml of DMF were added.

After 1 hr of reaction the resin was washed with 3×DCM, 2×MeOH and 3×DCM and progress of reaction was checked by Kaiser test which was negative (no free amine groups present).

C8-Dab(Boc)-OH ($M_w$=344.49) was cleaved from the resin by 1% TFA/DCM (5×30 ml for 2 min was filtered to flask with 2 ml 10% pyridine/MeOH) and solvent was evaporated.

C8-Dab(Boc)-C8 ($M_w$=455.74). Second coupling was carried out in solution. To the oily residue from the previous reaction 2.32 ml (11.7 mmol) of C8-amine (Sigma, $M_w$=129325, d=0.782), 4.84 g (11.7 mmol) of HCTU ($M_w$=473.7) and 2.23 ml (12.87 mmol) of DIPEA ($M_w$=129.2, d=0.74) in 50 ml of DMF were added. After 1 hr 100 ml of AcOEt was added and organic layer was washed in separatory funnel with 3×0.5 M HCl, 3×10% NaCO$_3$ and 3×NaCl. AcOEt layer was dried with anhydrous MgSO$_4$ and evaporated.

C8-Dab-C8 ($M_w$=355.74). To the oily residue from the previous reaction, 100 ml of 80% TFA/DCM 2.5% TIS was added and after 1 hr solvent was evaporated.

C8-norArg(diBoc)-C8 ($M_w$=597.74). The residue was dissolved in 50 ml of DCM and pH was adjusted to 9 with TEA. 2.23 g (5.85 mM, 1.5 eq) of 1,3-Di-Boc-2-(trifluoromethylsulfonyl)guanidine ($M_w$=391.36, Aldrich 15033) was added and after 4 hrs DCM was evaporated.

C8-norArg-C8 ($M_w$=398.8) To the oily residue from the previous reaction 100 ml of 95% TFA/DCM 2.5% TIS was added and after 3 hrs solvent was evaporated. Residue was dissolved in MeOH/AcCN/0.5 M HCl 1:1:1 and purified by RP_Akta Explorer on C18 Phenomenex column (Phenomenex RP, 250×21.2 mm, Serial No.: 234236-1, Column volume 83 ml) and eluted with 50-100% acetonitrile gradient using water as mobile phase within 3 CV; λ=215 nm. Acetonitrile was evaporated and the product was lyophilized. Yield: 1.1 g.

Example 14

In like fashion to Example 13 were made C10-norArg-C10 (Yield: 1.2 g), C12-norArg-C12 (Yield: 2.9 g), C14-norArg-C14 (Yield: 630 mg), and C16-norArg-C16 (Yield: 1.0 g).

Example 15

Preparation of C12-norArg-C12

N-(4-guanidino-1-oxo-1-(dodecylamino)butan-2-yl) dodecanamide

Fmoc-Dab(Boc)-resin. To 8 g of 2-chlorotrityl chloride resin with 1.3 mmol/g substitution (Novabiochem, (01-64-0114) in 100 ml of dry DCM in 500 ml reaction vessel for solid phase synthesis, 5 g (11.35 mmol, 1.2 eq) of Fmoc-Dab(Boc)-OH ($M_w$=440.5, (Fmoc-(N-γ-Boc)-L-α,γ-diaminobutyric acid, AnaSpec, 28246) and 4 ml (22.7 mmol, 2.0 eq) of DIPEA (Aldrich, $M_w$=129.2, d=0.74) were added.

Dab(Boc)-resin. After 2 hrs of shaking on the shaker the resin was washed 3× with DCM/MeOH/DIPEA (17:2:1), 3×DCM, 2×DMF, 3×DCM and Fmoc group was deprotected 2 times with 50 ml of 20% piperidine/DMF for 15 min.

C12-Dab(Boc)-resin. After Fmoc deprotection the resin was washed with 3×DCM, 2×MeOH and 3×DCM and for the coupling reaction 4.54 g (22.7 mmol) of C12-acid (Sigma, $M_w$=200.32), 9.48 g (22.7 mmol) of HCTU ($M_w$=413.7) and 4.52 ml (26 mmol) of DIPEA ($M_w$=129.2, d=0.74) in 100 ml of DMF were added.

After 1 hr of reaction the resin was washed with 3×DCM, 2×MeOH and 3×DCM and progress of reaction was checked by Kaiser test which was negative (no free amine groups present).

C12-Dab(Boc)-OH ($M_w$=400.59) was cleaved from the resin by 1% TFA/DCM (5×50 ml for 2 min was filtered to flask with 10 ml 10% pyridine/MeOH) and solvent was evaporated.

C12-Dab(Boc)-C12 ($M_w$=567.95). Second coupling was carried out in solution. To the oily residue from the previous reaction 2.168 g (11.7 mmol) of C12-amine (Sigma, $M_w$=185.36), 4.48 g (11.7 mmol) of HCTU ($M_w$=413.7) and 2.23 ml (12.87 mmol) of DIPEA ($M_w$=129.2, d=0.74) in 50 ml of DMF were added. After 1 hr 100 ml of AcOEt was added and organic layer was washed in separatory funnel with 3×0.1 M HCl, 3×5% NaCO$_3$ and 3×NaCl. AcOEt layer was dried with anhydrous MgSO$_4$ and evaporated.

C12-Dab-C12 ($M_w$=467.9). To the oily residue from the previous reaction, 150 ml of 80% TFA/DCM 2.5% TIS was added and after 1 hr solvent was evaporated.

C12-norArg(diBoc)-C12 ($M_w$=710.13). The residue was dissolved in 50 ml of DCM and pH was adjusted to 9-10 with TEA. 9 g (23 mM) of 1,3-Di-Boc-2-(trifluoromethylsulfonyl)guanidine ($M_w$=391.36, Aldrich 15033) was added and after 3 hrs DCM was evaporated. The product was purified on TELEDYNE Isco CombiFlash R$_f$ instrument, 120 g normal phase silica gel column, 100% DCM for 5.4 CV (column volume) and 0-5% MeOH for 6.3 CV, detection 215 nm, flow 70 ml/min.

C12-norArg-C12 ($M_w$=509.92) To the residue from the previous reaction 150 ml of 70% TFA/DCM 2.5% TIS was added and after 1 hr solvent was evaporated. Residue was precipitated by 0.5 M HCl.

Example 16

Preparation of C18-norArg-C18

N-(4-guanidino-1-oxo-1-(octadecylamino)butan-2-yl)octadecanamide

Fmoc-Dab(Boc)-resin. To 3 g of 2-chlorotrityl chloride resin with 1.3 mmol/g substitution (Novabiochem, (01-64-0114) in 30 ml of dry DCM in 30 ml reaction vessel for solid phase synthesis, 2.577 g (5.85 mmol, 1.5 eq) of Fmoc-Dab(Boc)-OH ($M_w$=440.5, (Fmoc-(N-γ-Boc)-L-α,γ-diaminobutyric acid, AnaSpec, 28246) and 2.03 ml (11.7 mmol, 3.0 eq) of DIPEA (Aldrich, $M_w$=129.2, d=0.74) were added.

Dab(Boc)-resin. After 2 hrs the resin was washed 3× with DCM/MeOH/DIPEA (17:2:1), 3×DCM, 2×DMF, 3×DCM and Fmoc group was deprotected with 30 ml of 20% piperidine/DMF for 30 min.

C18-Dab(Boc)-resin. After Fmoc deprotection the resin was washed with 3×DCM, 2×MeOH and 3×DCM2 and for the coupling reaction 2.21 g (7.8 mmol) of C18 acid (Sigma, $M_w$=284.48), 3.32 g (7.8 mmol) of HCTU ($M_w$=473.7) and 1.49 ml (8.58 mmol) of DIPEA ($M_w$=129.2, d=0.74) in 30 ml of DMF were added.

After 1 hr of reaction the resin was washed with 3×DCM, 2×MeOH and 3×DCM and progress of reaction was checked by Kaiser test which was negative (no free amine groups present).

C18-Dab(Boc)-OH ($M_w$=568.56) was cleaved from the resin by 1% TFA/DCM (5×30 ml for 2 min was filtered to flask with 2 ml 10% pyridine/MeOH) and solvent was evaporated.

C18-Dab(Boc)-C18 ($M_w$=735.95). Second coupling was carried out in solution. To the oily residue from the previous reaction, 2.1 g (7.8 mmol) of C18-amine (Sigma, $M_w$=269.52), 3.32 g (7.8 mmol) of HCTU ($M_w$=473.7) and 1.49 ml (8.58 mmol) of DIPEA ($M_w$=129.2, d=0.74) in 50 ml of DMF were added. After 1 hr 100 ml of AcOEt was added and organic layer was washed in separatory funnel with 3×0.5 M HCl, 3×10% NaCO$_3$ and 3×NaCl. AcOEt layer was dried with anhydrous MgSO$_4$ and evaporated.

C18-Dab-C18 ($M_w$=635.9). To the oily residue from the previous reaction, 100 ml of 80% TFA/DCM 2.5% TIS was added and after 1 hr solvent was evaporated.

C18-norArg(diBoc)-C18 ($M_w$=872.13). The residue was dissolved in 50 ml of DCM and pH was adjusted to 9 with TEA. 2.23 g (5.85 mM, 1.5 eq) of 1,3-Di-Boc-2-(trifluoromethylsulfonyl)guanidine ($M_w$=391.36, Aldrich 15033) was added and after 4 hrs DCM was evaporated.

C18-norArg-C18 ($M_w$=677.92) To the oily residue from the previous reaction 100 ml of 95% TFA/DCM 2.5% TIS was added and after 3 hrs solvent was evaporated. Residue was precipitated by mixture of AcCN/0.5 M HCl 1:1.

Example 17

Preparation of C18(oleic)-norArg-C8

N-(4-guanidino-1-oxo-1-(octylamino)butan-2-yl)octadec-9-enamide

Fmoc-Dab(Boc)-resin. To 5 g of 2-chlorotrityl chloride resin with 1.3 mmol/g substitution (Novabiochem, (01-64-0114) in 50 ml of dry DCM in 50 ml reaction vessel for solid phase synthesis, 5.726 g (13 mmol, 2 eq) of Fmoc-Dab(Boc)-OH ($M_w$=440.5, (Fmoc-(N-γ-Boc)-L-α,γ-diaminobutyric acid, AnaSpec, 28246) and 2.26 ml (13 mmol, 2.0 eq) of DIPEA (Aldrich, $M_w$=129.2, d=0.74) were added.

Dab(Boc)-resin. After 2 hrs the resin was washed 3× with DCM/MeOH/DIPEA (17:2:1), 3×DCM, 2×DMF, 3×DCM and Fmoc group was deprotected with 40 ml of 20% piperidine/DMF 2 times for 30 min.

C18oleic-Dab(Boc)-resin. After Fmoc deprotection the resin was washed with 3×DCM, 2×MeOH and 3×DCM and for the coupling reaction 3.7 g (13 mmol) of oleic acid (Sigma, $M_w$=282.47, d=0.891), 5.37 g (13 mmol) of HCTU ($M_w$=413.7) and 2.62 ml (13 mmol) of DIPEA ($M_w$=129.2, d=0.74) in 50 ml of DMF were added.

After 2 hr of reaction the resin was washed with 3×DCM, 2×MeOH and 3×DCM and progress of reaction was checked by Kaiser test which was negative (no free amine groups present).

C18oleic-Dab(Boc)-OH ($M_w$=538.56) was cleaved from the resin by 1% TFA/DCM (5×50 ml for 2 min was filtered to flask with 2 ml 10% pyridine/MeOH) and solvent was evaporated.

C18oleic-Dab(Boc)-C8 ($M_w$=594.01). Second coupling was carried out in solution. To the oily residue from the previous reaction, 1.227 g (9.75 mmol) of C8-amine (Sigma, $M_w$=129.25), 4.033 g (9.75 mmol) of HCTU ($M_w$=413.7) and 1.69 ml (9.75 mmol) of DIPEA ($M_w$=129.2, d=0.74) in 50 ml of DMF were added. After 4 hr 100 ml of AcOEt was added and organic layer was washed in separatory funnel with 3×0.5 M HCl, 3×10% NaCO$_3$ and 3×NaCl. AcOEt layer was dried with anhydrous MgSO$_4$ and evaporated.

C18oleic-Dab-C8 ($M_w$=493.92). To the oily residue from the previous reaction, 70 ml of 80% TFA/DCM 2.5% TIS was added and after 20 min solvent was removed under reduced pressure.

C18oleic-norArg(diBoc)-C8 ($M_w$=735.95). The residue was dissolved in 50 ml of DCM and pH was adjusted to 9 with TEA. 2.543 g (6.5 mM, 1 eq) of 1,3-Di-Boc-2-(trifluoromethylsulfonyl)guanidine ($M_w$=391.36, Aldrich 15033) was added and after 4 hrs DCM was evaporated.

C18oleic-norArg-C8 ($M_w$=535.89) To the oily residue from the previous reaction 100 ml of 80% TFA/DCM 2.5% TIS was added and after 20 min solvent was evaporated. Crude product was purified on TELEDYNE Isco Combi-Flash $R_f$ instrument using 40 g normal phase silica gel column, 100% DCM for 3 CV (column volume) and 0-15% MeOH for 7 CV, detection 214 nm, flow 45 ml/min TLC: Rf=0.2 ($CH_2Cl_2$: MeOH=9:1). DCM/MeOH was evaporated and residue was precipitated by 0.1M HCl. Yield: 0.7 g.

Example 18

Preparation of C18(oleic)-norArg-C12

N-(4-guanidino-1-oxo-1-(dodecylamino)butan-2-yl)octadec-9-enamide

Fmoc-Dab(Boc)-resin. To 5 g of 2-chlorotrityl chloride resin with 1.3 mmol/g substitution (Novabiochem, (01-64-0114) in 50 ml of dry DCM in 50 ml reaction vessel for solid phase synthesis, 5.726 g (13 mmol, 2 eq) of Fmoc-Dab(Boc)-OH ($M_w$=440.5, (Fmoc-(N-γ-Boc)-L-α,γ-diaminobutyric acid, AnaSpec, 28246) and 2.26 ml (13 mmol, 2.0 eq) of DIPEA (Aldrich, $M_w$=129.2, d=0.74) were added.

Dab(Boc)-resin. After 2 hrs the resin was washed 3× with DCM/MeOH/DIPEA (17:2:1), 3×DCM, 2×DMF, 3×DCM and Fmoc group was deprotected with 40 ml of 20% piperidine/DMF 2 times for 30 min.

C18oleic-Dab(Boc)-resin. After Fmoc deprotection the resin was washed with 3×DCM, 2×MeOH and 3×DCM and for the coupling reaction 3.7 g (13 mmol) of oleic acid (Sigma, $M_w$=282.47, d=0.891), 5.37 g (13 mmol) of HCTU ($M_w$=413.7) and 2.62 ml (13 mmol) of DIPEA ($M_w$=129.2, d=0.74) in 50 ml of DMF were added.

After 2 hr of reaction the resin was washed with 3×DCM, 2×MeOH and 3×DCM and progress of reaction was checked by Kaiser test which was negative (no free amine groups present).

C18oleic-Dab(Boc)-OH ($M_w$=538.56) was cleaved from the resin by 1% TFA/DCM (5×50 ml for 2 min was filtered to flask with 2 ml 10% pyridine/MeOH) and solvent was evaporated.

C18oleic-Dab(Boc)-C12 ($M_w$=650.03). Second coupling was carried out in solution. To the oily residue from the previous reaction, 1.76 g (9.75 mmol) of C12-amine (Sigma, $M_w$=185.36), 4.033 g (9.75 mmol) of HCTU ($M_w$=413.7) and 1.69 ml (9.75 mmol) of DIPEA ($M_w$=129.2, d=0.74) in 50 ml of DMF were added. After 4 hr 100 ml of AcOEt was added and organic layer was washed in separatory funnel with 3×0.5 M HCl, 3×10% $NaCO_3$ and 3×NaCl. AcOEt layer was dried with anhydrous $MgSO_4$ and evaporated.

C18oleic-Dab-C12 ($M_w$=549.91). To the oily residue from the previous reaction, 70 ml of 80% TFA/DCM 2.5% TIS was added and after 20 min solvent was removed under reduced pressure.

C18oleic-norArg(diBoc)-C12 ($M_w$=792.5). The residue was dissolved in 50 ml of DCM and pH was adjusted to 9 with TEA. 2.543 g (6.5 mM, 1 eq) of 1,3-Di-Boc-2-(trifluoromethylsulfonyl)guanidine ($M_w$=391.36, Aldrich 15033) was added and after 4 hrs DCM was evaporated.

C18oleic-norArg-C12 ($M_w$=591.55) To the oily residue from the previous reaction 100 ml of 80% TFA/DCM 2.5% TIS was added and after 20 min solvent was evaporated. Crude product was purified on TELEDYNE Isco Combi-Flash $R_f$ instrument using 40 g normal phase silica gel column, 100% DCM for 3 CV (column volume) and 0-20% MeOH for 10 CV, detection 214 nm, flow 45 ml/min. TLC: Rf=0.2 ($CH_2Cl_2$: MeOH=9:1) DCM/MeOH were evaporated and residue was precipitated by 0.1M HCl.

Example 19

Preparation of C18(oleic)-norArg-C16

N-(4-guanidino-1-oxo-1-(hexadecylamino)butan-2-yl)octadec-9-enamide

Fmoc-Dab(Boc)-resin. To 5 g of 2-chlorotrityl chloride resin with 1.3 mmol/g substitution (Novabiochem, (01-64-0114) in 50 ml of dry DCM in 50 ml reaction vessel for solid phase synthesis, 5.726 g (13 mmol, 2 eq) of Fmoc-Dab(Boc)-OH ($M_w$=440.5, (Fmoc-(N-γ-Boc)-L-α,γ-diaminobutyric acid, AnaSpec, 28246) and 2.26 ml (13 mmol, 2.0 eq) of DIPEA (Aldrich, $M_w$=129.2, d=0.74) were added.

Dab(Boc)-resin. After 2 hrs the resin was washed 3× with DCM/MeOH/DIPEA (17:2:1), 3×DCM, 2×DMF, 3×DCM and Fmoc group was deprotected with 40 ml of 20% piperidine/DMF 2 times for 30 min.

C18oleic-Dab(Boc)-resin. After Fmoc deprotection the resin was washed with 3×DCM, 2×MeOH and 3×DCM and for the coupling reaction 3.7 g (13 mmol) of oleic acid (Sigma, $M_w$=282.47, d=0.891), 5.37 g (13 mmol) of HCTU ($M_w$=413.7) and 2.62 ml (13 mmol) of DIPEA ($M_w$=129.2, d=0.74) in 50 ml of DMF were added.

After 2 hr of reaction the resin was washed with 3×DCM, 2×MeOH and 3×DCM and progress of reaction was checked by Kaiser test which was negative (no free amine groups present).

C18oleic-Dab(Boc)-OH ($M_w$=538.56) was cleaved from the resin by 1% TFA/DCM (5×50 ml for 2 min was filtered to flask with 2 ml 10% pyridine/MeOH) and solvent was evaporated.

C18oleic-Dab(Boc)-C16 ($M_w$=705.95). Second coupling was carried out in solution. To the oily residue from the previous reaction, 2.354 g (9.75 mmol) of C16-amine (Sigma, $M_w$=241.46), 4.033 g (9.75 mmol) of HCTU ($M_w$=413.7) and 1.69 ml (9.75 mmol) of DIPEA ($M_w$=129.2, d=0.74) in 50 ml of DMF were added. After 4 hr 100 ml of AcOEt was added and organic layer was washed in separatory funnel with 3×0.5 M HCl, 3×10% $NaCO_3$ and 3×NaCl. AcOEt layer was dried with anhydrous $MgSO_4$ and evaporated.

C18oleic-Dab-C16 ($M_w$=605.9). To the oily residue from the previous reaction, 70 ml of 80% TFA/DCM 2.5% TIS was added and after 20 min solvent was removed under reduced pressure.

C18oleic-norArg(diBoc)-C16 ($M_w$=842.13). The residue was dissolved in 50 ml of DCM and pH was adjusted to 9 with TEA. 2.543 g (6.5 mM, 1 eq) of 1,3-Di-Boc-2-(trifluoromethylsulfonyl)guanidine ($M_w$=391.36, Aldrich 15033) was added and after 4 hrs DCM was evaporated.

C18oleic-norArg-C16 ($M_w$=647.92) To the oily residue from the previous reaction 100 ml of 80% TFA/DCM 2.5% TIS was added and after 20 min solvent was evaporated. Crude product was purified on TELEDYNE Isco Combi-Flash $R_f$ instrument using 48 g normal phase silica gel column, 100% DCM for 3 CV (column volume) and 0-20% MeOH for 10 CV, detection 214 nm, flow 45 ml/min. DCM/MeOH was evaporated and residue was precipitated by 0.1M HCl.

Example 20

Preparation of C18(oleic)-norArg-C18

N-(4-guanidino-1-oxo-1-(octadecylamino)butan-2-yl)octadec-9-enamide

Fmoc-Dab(Boc)-resin. To 5 g of 2-chlorotrityl chloride resin with 1.3 mmol/g substitution (Novabiochem, (01-64-0114) in 50 ml of dry DCM in 60 ml reaction vessel for solid phase synthesis, 5.726 g (13 mmol, 2 eq) of Fmoc-Dab (Boc)-OH ($M_w$=440.5, (Fmoc-(N-γ-Boc)-L-α,γ-diaminobutyric acid, AnaSpec, 28246) and 2.26 ml (13 mmol, 2.0 eq) of DIPEA (Aldrich, $M_w$=129.2, d=0.74) were added.

Dab(Boc)-resin. After 3 hrs the resin was washed 3× with DCM/MeOH/DIPEA (17:2:1), 3×DCM, 2×DMF, 3×DCM and Fmoc group was deprotected with 50 ml of 20% piperidine/DMF twice for 15 min.

C18:1-Dab(Boc)-resin. After Fmoc deprotection the resin was washed with 3×DCM, 2×MeOH and 3×DCM and for the coupling reaction 3.7 g (13 mmol) of oleic acid (Sigma, $M_w$=282.47, d=0.891), 5.37 g (13 mmol) of HCTU ($M_w$=413.7) and 2.62 ml (13 mmol) of DIPEA ($M_w$=129.2, d=0.74) in 50 ml of DMF were added.

After 1 hr of reaction the resin was washed with 3×DCM, 2×MeOH and 3×DCM and progress of reaction was checked by Kaiser test which was negative (no free amine groups present).

C18:1-Dab(Boc)-OH ($M_w$=566.56) was cleaved from the resin by 1% TFA/DCM (5×50 ml for 2 min was filtered to flask with 2 ml 10% pyridine/MeOH) and solvent was evaporated.

C18:1-Dab(Boc)-C18:1 ($M_w$=734.95). Second coupling was carried out in solution. To the oily residue from the previous reaction, 3.725 g (9.75 mmol) of oleyl amine (Sigma, $M_w$=267.49, 70%), 4.033 g (9.75 mmol) of HCTU ($M_w$=413.7) and 1.69 ml (9.75 mmol) of DIPEA ($M_w$=129.2, d=0.74) in 50 ml of DMF were added. After 4 hr 100 ml of AcOEt was added and organic layer was washed in separatory funnel with 3×0.5 M HCl, 3×10% NaCO₃ and 3×NaCl. AcOEt layer was dried with anhydrous MgSO₄ and evaporated.

C18:1-Dab-C18 ($M_w$=635.9). To the oily residue from the previous reaction, 100 ml of 80% TFA/DCM 2.5% TIS was added and after 20 min solvent was evaporated.

C18:1-norArg(diBoc)-C18:1 ($M_w$=874.13). The residue was dissolved in 50 ml of DCM and pH was adjusted to 9 with TEA. 2.348 g (6 mM, 1 eq) of 1,3-Di-Boc-2-(trifluoromethylsulfonyl)guanidine ($M_w$=391.36, Aldrich 15033) was added and after 4 hrs DCM was evaporated.

C18:1-norArg-C18:1 ($M_w$=674.1) To the oily residue from the previous reaction 100 ml of 95% TFA/DCM 2.5% TIS was added and after 3 hrs solvent was evaporated. Crude product was purified on TELEDYNE Isco CombiFlash $R_f$ instrument using 48 g normal phase silica gel column, 100% DCM for 3 CV (column volume) and 0-20% MeOH for 10 CV, detection 214 nm, flow 45 ml/min. DCM/MeOH was evaporated and residue was precipitated by 0.1M HCl. Yield: 3.2 g.

Example 21

Preparation of C10-[4-Pal(N—CH₃)]—C10

4-(3-(decylamino)-3-oxo-2-decanamidopropyl)-1-methylpyridinium chloride

Fmoc-4-Pal-resin. To 3 g of 2-chlorotrityl chloride resin with 1.3 mmol/g substitution (Novabiochem, (01-64-0114) in 30 ml of dry DCM in 30 ml reaction vessel for solid phase synthesis, 2.27 g (5.85 mmol, 1.5 eq) of Fmoc-4-Pal-OH (Fmoc-4-Pyridinylalanine, $M_w$=388.42, Advanced ChemTech, FX4140) and 2.03 ml (11.7 mmol, 3.0 eq) of DIPEA (Aldrich, $M_w$=129.2, d=0.74) were added.

4-Pal-resin. After 2 hrs the resin was washed 3× with DCM/MeOH/DIPEA (17:2:1), 3×DCM, 2×DMF, 3×DCM and Fmoc group was deprotected with 30 ml of 20% piperidine/DMF for 30 min.

C10-4-Pal-resin. After Fmoc deprotection the resin was washed with 3×DCM, 2×MeOH and 3×DCM and for the coupling reaction 1.48 g (11.7 mmol) of decanoic acid (Sigma, $M_w$=127.27), 5.54 g (11.7 mmol) of HCTU ($M_w$=473.7) and 2.23 ml (12.87 mmol) of DIPEA ($M_w$=129.2, d=0.74) in 30 ml of DMF were added.

After 1 hr of reaction the resin was washed with 3×DCM, 2×MeOH and 3×DCM and progress of reaction was checked by Kaiser test which was negative (no free amine groups present).

C10-4-Pal-OH ($M_w$=320.46) was cleaved from the resin by 1% TFA/DCM (5×30 ml for 2 min was filtered to flask with 2 ml 10% pyridine/MeOH) and solvent was evaporated.

C10-4-Pal-C10 ($M_w$=459.76). Second coupling was carried out in solution. To the oily residue from the previous reaction 2.32 ml (11.7 mmol) of C10-amine (Sigma, $M_w$=157.3, d=0.792), 5.54 g (11.7 mmol) of HCTU ($M_w$=473.7) and 2.23 ml (12.87 mmol) of DIPEA ($M_w$=129.2, d=0.74) in 50 ml of DMF were added. After 1 hr 100 ml of AcOEt was added and organic layer was washed in separatory funnel with 3×0.5 M HCl, 3×10% NaCO₃ and 3×NaCl. AcOEt layer was dried with anhydrous MgSO₄ and evaporated. Residue was dissolved in AcCN/0.5 M HCl 1:1 and purified by RP_Akta Explorer on C18 Phenomenex column (Phenomenex RP, 250×21.2 mm, Serial No.: 234236-1, Column volume 83 ml) and eluted with 30-100% acetonitrile gradient using water as mobile phase within 2 CV; λ=215 nm. Acetonitrile was evaporated and the product was lyophilized.

C10-4-Pal(Me)-C10 ($M_w$=474.76). Methylation was carried out in solution. To 0.4 g (0.87 mM) of C10-4-Pal-C10 ($M_w$=459.76) dissolved in 20 ml of THF, 83 μl (0.87 mmol) of dimethyl sulfate (Sigma, $M_w$=126.13, d=1.325) was added. After overnight reaction the same amount of dimethyl sulfate was added and after 1 hr the product was precipitated with 0.5 M HCl/AcCN mixture.

Example 22

Preparation of C12-[4-Pal(N—CH₃)]—C12

4-(3-(dodecylamino)-3-oxo-2-dodecanamidopropyl)-1-methylpyridinium chloride

Fmoc-4-Pal-resin. To 6.5 g of 2-chlorotrityl chloride resin with 1.3 mmol/g substitution (Novabiochem, (01-64-0114) in 70 ml of dry DCM in 200 ml reaction vessel for solid phase synthesis, 3.5 g (9.01 mmol, 1.5 eq) of Fmoc-4-Pal-OH (Fmoc-4-Pyridinylalanine, $M_w$=388.42, Advanced ChemTech, FX4140) and 3.132 ml (18 mmol, 2.2 eq) of DIPEA (Aldrich, $M_w$=129.2, d=0.74) were added.

4-Pal-resin. After 2 hrs the resin was washed 3× with DCM/MeOH/DIPEA (17:2:1), 3×DCM, 2×DMF, 3×DCM and Fmoc group was deprotected 2* with 70 ml of 20% piperidine/DMF for 15 min.

C12-4-Pal-resin. After Fmoc deprotection the resin was washed with 3×DCM, 2×MeOH and 3×DCM and for the coupling reaction 2.549 g (12.675 mmol, 1.5 eq) of lauric acid (Sigma, $M_w$=200.32), 5.3 g (12.675 mmol) of HCTU ($M_w$=417.7) and 2.2 ml (12.675 mmol) of DIPEA ($M_w$=129.2, d=0.74) in 70 ml of DMF were added.

After 1 hr of reaction the resin was washed with 3×DCM, 2×MeOH and 3×DCM and progress of reaction was checked by Kaiser test which was negative (no free amine groups present).

C12-4-Pal-OH ($M_w$=346.7) was cleaved from the resin by 1% TFA/DCM (5×30 ml for 2 min was filtered to flask with 2 ml 10% pyridine/MeOH) and solvent was evaporated.

C12-4-Pal-C12 ($M_w$=515.7). Second coupling was carried out in solution. To the oily residue from the previous reaction 2.3 g (12 mmol) of EDC*HCl ($M_w$=191.7), 1.86 g (12 mmol) of HOBt*H$_2$O ($M_w$=153.1) and 10.44 ml (60 mmol, 5 eq) of DIPEA ($M_w$=129.2, d=0.74) in 70 ml of DCM were added. Preactivation step was carried out for 20 min and then 2.22 g (12 mmol) of C12-amine (Sigma, $M_w$=185.36) was added. After overnight reaction the organic layer was washed in separatory funnel with 3×0.5 M HCl, 3×10% NaCO$_3$ and 3×NaCl. DCM was dried with anhydrous MgSO$_4$ and evaporated. The product was purified on TELEDYNE Isco CombiFlash $R_f$ instrument, 40 g normal phase silica gel column, 100% DCM for 5 CV (column volume) and 0-5% MeOH for 10 CV, detection 254 nm, flow 40 ml/min.

C12-4-Pal(Me)-C12 ($M_w$=530.8). Methylation was carried out in solution. To 4 g (7.75 mM) of C12-4-Pal-C12 ($M_w$=415.7) dissolved in 50 ml of THF, 1.1 ml (11.625 mmol) of dimethyl sulfate (Sigma, $M_w$=126.13, d=1.325) was added. After overnight reaction 0.5 ml of dimethyl sulfate was added and after 1 hr the solvent was evaporated and the product was precipitated with 0.5 M HCl.

Example 23

Preparation of C18oleic-[4-Pal]-C16

N-(1-oxo-3-(pyridin-4-yl)-1-(hexadecylamino)propan-2-yl)octadec-9-enamide

Fmoc-4-Pal-resin. To 5 g of 2-chlorotrityl chloride resin with 1.3 mmol/g substitution (Novabiochem, (01-64-0114) in 50 ml of dry DCM in 50 ml reaction vessel for solid phase synthesis 3.787 g (9.75 mmol, 1.5 eq) of Fmoc-4-Pal-OH ($M_w$=388.42, Advanced ChemTech) and 1.7 ml (9.75 mmol, 1.5 eq) of DIPEA (Aldrich, $M_w$=129.2, d=0.74) were added.

4-Pal-resin. After 2 hrs the resin was washed 3× with DCM/MeOH/DIPEA (17:2:1), 3×DCM, 2×DMF, 3×DCM and Fmoc group was deprotected with 40 ml of 20% piperidine/DMF 2 times for 15 min.

C18oleic-4-Pal-resin. After Fmoc deprotection the resin was washed with 3×DCM, 2×MeOH and 3×DCM and for the coupling reaction 3.7 g (13 mmol) of oleic acid (Sigma, $M_w$=282.47, d=0.891), 5.37 g (13 mmol) of HCTU ($M_w$=413.7) and 2.62 ml (13 mmol) of DIPEA ($M_w$=129.2, d=0.74) in 50 ml of DMF were added.

After 2 hr of reaction the resin was washed with 3×DCM, 2×MeOH and 3×DCM and progress of reaction was checked by Kaiser test which was negative (no free amine groups present).

C18oleic-4-Pal-OH ($M_w$=430.62) was cleaved from the resin by 1% TFA/DCM (5×50 ml for 2 min was filtered to flask with 2 ml 10% pyridine/MeOH) and solvent was evaporated.

C18oleic-4-Pal-C16 ($M_w$=654.06). Second coupling was carried out in solution. To the oily residue from the previous reaction, 2.354 g (9.75 mmol) of C16-amine (Sigma, $M_w$=241.46), 4.033 g (9.75 mmol) of HCTU ($M_w$=413.7) and 1.69 ml (9.75 mmol) of DIPEA ($M_w$=129.2, d=0.74) in 50 ml of DMF were added. After 4 hr 100 ml of AcOEt was added and organic layer was washed in separatory funnel with 3×0.5 M HCl, 3×10% NaCO$_3$ and 3×NaCl. AcOEt layer was dried with anhydrous MgSO$_4$ and evaporated. Crude product was purified on TELEDYNE Isco CombiFlash $R_f$ instrument using 48 g normal phase silica gel column, 100% DCM for 3 CV (column volume) and 0-20% MeOH for 10 CV, detection 214 nm, flow 45 ml/min. DCM/MeOH was evaporated and residue was precipitated by 0.1M HCl. Yield: 0.75 g.

Example 24

Preparation of (C18oleic)-(1-CH$_3$—His)-NH—(C16alkyl)

N-(3-(1-methyl-1H-imidazol-4-yl)-1-oxo-1-(hexadecylamino)propan-2-yl)octadec-9-enamide Fmoc-His(1-Me)-resin. To 1.7 g of 2-chlorotrityl chloride resin with 1.3 mmol/g substitution (Novabiochem, (01-64-0114) in 30 ml of dry DCM in 60 ml reaction vessel for solid phase synthesis, 1 g (2.5 mmol, 1.2 eq) of Fmoc-His(1-Me)-OH ($M_w$=391.43, ChemImpex) and 0.435 ml (2.5 mmol, 1.2 eq) of DIPEA (Aldrich, $M_w$=129.2, d=0.74) were added.

His(1-Me)-resin. After 2 hrs the resin was washed 3× with DCM/MeOH/DIPEA (17:2:1), 3×DCM, 2×DMF, 3×DCM and Fmoc group was deprotected 2 times with 50 ml of 20% piperidine/DMF for 15 min.

C18$_{oleic}$-His(1-Me)-resin. After Fmoc deprotection the resin was washed with 3×DCM, 2×MeOH and 3×DCM and for the coupling reaction 1.247 g (4.4 mmol) of oleic acid (Sigma, $M_w$=282.47; d=0.891), 1.82 g (4.4 mmol) of HCTU ($M_w$=413.7) and 0.765 ml (9.1 mmol) of DIPEA ($M_w$=129.2, d=0.74) in 50 ml of DMF were added.

After 2 hr of reaction the resin was washed with 3×DCM, 2×MeOH and 3×DCM and progress of reaction was checked by Kaiser test which was negative (no free amine groups present).

C18$_{oleic}$-His(1-Me)-OH was cleaved from the resin by 1% TFA/DCM (5×50 ml for 2 min was filtered to flask with 2 ml 10% pyridine/MeOH) and solvent was evaporated.

C18$_{oleic}$-His(1-Me)-C16 ($M_w$=657.07) Second coupling was carried out in solution. To the oily residue from the previous step 0.604 g (2.5 mmol) of C16 amine (Sigma), 1.034 g (2.5 mmol) of HCTU ($M_w$=413.7) and 0.435 ml (2.5 mmol) of DIPEA ($M_w$=129.2, d=0.74) in 50 ml of DMF were added. After overnight reaction organic layer was diluted with acetic acetate and washed in separatory funnel with 3×0.5 M HCl, 3×10% NaCO$_3$ and 3×NaCl. AcOEt layer was dried with anhydrous MgSO$_4$ and evaporated. The crude product was purified on TELEDYNE Isco CombiFlash $R_f$ instrument, 40 g normal phase silica gel column, 100% DCM for 5 CV (column volume) and 0-20% MeOH for 10 CV, detection 214 nm, flow 40 ml/min. Purified product was precipitated with 0.1 M HCl. Yield: 1 g.

Example 25

Preparation of (C18oleic)-(3',5'-diiodo-Tyr)-NH—(C16alkyl)

(E)-N-(1-(hexadecylamino)-3-(4-hydroxy-3,5-diiodophenyl)-1-oxopropan-2-yl)octadec-9-enamide Proposed Preparation.

Fmoc-Tyr(3',5'-diI)-resin. To 5 g of 2-chlorotrityl chloride resin with 1.3 mmol/g substitution (Novabiochem, (01-64-0114) in 50 ml of dry DCM in 50 ml reaction vessel for solid phase synthesis, 6.388 g (9.75 mmol, 1.5 eq) of Fmoc-Tyr (3',5'-diI)—OH ($M_w$=655.2, AnaSpec) and 1.69 ml (9.75 mmol, 1.5 eq) of DIPEA (Aldrich, $M_w$=129.2, d=0.74) to be added.

Tyr(3',5'-diI)-resin. After 3 hrs the resin to be washed 3× with DCM/MeOH/DIPEA (17:2:1), 3×DCM, 2×DMF, 3×DCM and Fmoc group to be deprotected with 40 ml of 20% piperidine/DMF 2 times for 30 min.

C18oleic-Tyr(3',5'-diI)-resin. After Fmoc deprotection the resin to be washed with 3×DCM, 2×MeOH and 3×DCM and for the coupling reaction 3.7 g (13 mmol) of oleic acid (Sigma, $M_w$=282.47, d=0.891), 5.37 g (13 mmol) of HCTU ($M_w$=413.7) and 2.62 ml (13 mmol) of DIPEA ($M_w$=129.2, d=0.74) in 50 ml of DMF to be added.

After 3 hr of reaction the resin to be washed with 3×DCM, 2×MeOH and 3×DCM and progress of reaction to be checked by Kaiser test.

C18oleic-Tyr(3',5'-diI)—OH ($M_w$=697.43) to be cleaved from the resin by 1% TFA/DCM (5×50 ml for 2 min to be filtered to flask with 2 ml 10% pyridine/MeOH and solvent to be evaporated.

C18oleic-Tyr(3',5'-diI)—C16 ($M_w$=920.38). Second coupling to be carried out in solution. To the oily residue from the previous reaction, 2.354 g (9.75 mmol) of C16-amine (Sigma, $M_w$=241.46), 4.033 g (9.75 mmol) of HCTU ($M_w$=413.7) and 1.69 ml (9.75 mmol) of DIPEA ($M_w$=129.2, d=0.74) in 50 ml of DMF to be added. After 4 hr 100 ml of AcOEt to be added and organic layer to be washed in separatory funnel with 3×0.5 M HCl, 3×10% NaCO$_3$ and 3×NaCl. AcOEt layer to be dried with anhydrous MgSO$_4$ and evaporated. Crude product to be purified on TELEDYNE Isco CombiFlash R$_f$ instrument using 48 g normal phase silica gel column, 100% DCM for 3 CV (column volume) and 0-20% MeOH for 10 CV, detection 214 nm, flow 45 ml/min. DCM/MeOH to be evaporated and residue to be precipitated by mixture of AcCN/H$_2$O.

Example 26

Example In Vitro Assay for LacZ Gene Expression Knockdown in 9L Cells

9L/LacZ is a rat gliosarcoma cell line stably expressing the LacZ gene that encodes bacterial galactosidase. LacZ gene knockdown measurements can be used as a primary activity-based in vitro assay for interfering RNA delivery formulations.

For LacZ gene knockdown measurements, 9L/LacZ cells were transfected with an RNAi formulation, and a β-galactosidase assay was performed on cells harvested at day 3 post transfection. An additional assay was performed to quantify protein concentration. 9L/LacZ cells were plated at 8000 cells/well (96-well) and incubated overnight in medium. Confluency was about 15-20% at the time of transfection. Transfection complex was prepared by adding an interfering RNA to OptiMEM™ medium and vortexing, separately adding a delivery formulation to OptiMEM™ medium and vortexing, and finally mixing the interfering RNA in medium with the delivery formulation in medium to make the transfection complex. The medium for incubated cells was replaced with fresh no-serum media (OptiMEM™ without serum) and transfection complex was added to each well. Cells were incubated 5 hrs, then after the addition of 100 microliters complete medium (DMEM plus 10% fetal bovine serum) were incubated overnight at 37° C. and 5% CO$_2$. The next day, 24 hours after transfection, the medium was changed to fresh complete medium and the cells were incubated another 48 hrs at 37° C. and 5% CO$_2$.

For LacZ gene knockdown, the harvested 9L/LacZ cells were washed in PBS, lysed in M-PER™ Reagent (Pierce), and incubated at room temperature for 15 minutes. Lysate was taken from each well for protein assay with a Micro BCA kit (Pierce, ThermoFisher Scientific) and β-gal assay with All-in-One™ β-Galactosidase Assay Reagent (Pierce).

Example In Vitro Assay for PPIB Gene Expression Knockdown in A549 Cells

Cyclophilin B (PPIB) gene knockdown measurements can be used as a primary activity-based in vitro assay for interfering RNA delivery formulations. Cyclophilin B (PPIB) gene expression knockdown was measured in A549 human alveolar basal epithelial cells. For PPIB gene knockdown measurements, A549 cells were transfected with an interfering RNA formulation, total RNA prepared 24 hours after transfection, and PPIB mRNA assayed by RT-PCR. QRT-PCR of 36B4 (acidic ribosomal phosphoprotein PO) mRNA expression was performed for normalization.

A549 cells were seeded at 7,500 cells/well (96-well) and incubated overnight in medium. Confluency was about 50% at the time of transfection. Transfection complex was prepared by adding an interfering RNA to medium (OptiMEM™) and vortexing, separately adding a delivery formulation to medium (OptiMEM™) and vortexing, and finally mixing the interfering RNA in medium with the delivery formulation in medium and incubating 20 minutes at room temperature to make the transfection complex. The medium for incubated cells was replaced with fresh OptiMEM™ and transfection complex was added to each well. Cells were incubated for 5 hrs at 37° C. and 5% CO$_2$, then complete medium was added (to a final fetal bovine serum concentration 10%) and incubation continued until 24 hours post-transfection.

For PPIB gene knockdown cells were lysed and RNA prepared (Invisorb RNA Cell HTS 96-Kit/C, Invitek, Berlin, or RNeasy 96 Kit, Qiagen). Quantitative RT-PCR was performed using One-Step qRT-PCR kit (Invitrogen) on a DNA Engine Opticon2 thermal cycler (BioRad).

Primers used for PPIB were:

```
                                        (SEQ ID NO: 1)
5'-GGCTCCCAGTTCTTCATCAC-3' (forward)
and
                                        (SEQ ID NO: 2)
5'-CCTTCCGCACCACCTC-3' (reverse)
with
                                        (SEQ ID NO: 3)
5'-FAM-CTAGATGGCAAGCATGTGGTGTTTGG-TAMRA-3'
for the probe.
```

For 36B4, primers were:

5'-TCTATCATCAACGGGTACAAACGA-3' (forward) (SEQ ID NO: 4)
and

5'-CTTTTCAGCAAGTGGGAAGGTG-3' (reverse) (SEQ ID NO: 5)
with

5'-FAM-CCTGGCCTTGTCTGTGGAGACGGATTA-TAMRA-3' (SEQ ID NO: 6)
for the probe.

Example In Vivo Assay for Influenza Viral Titer Knockdown in Mouse

Influenza viral titer knockdown measurements in mice can be used as an in vivo gauge of efficacy for interfering RNA amino acid lipid delivery formulations.

In this assay, typically 50 uL of a dsRNA amino acid lipid formulation, or PBS for a control group, was administered intranasally in 7-9 week old Balb/C mice anesthetized with ketamine/xylazine. Daily dosing was performed for 3 consecutive days on days −2, −1, and 0. Infection was induced 4 hours after the last dosing.

Influenza infection was induced with Influenza A/Puerto Rico/8/34 (PR8, subtype H1N1). For infection, 50 µl of 20 pfu PR8 diluted in 0.3% BSA/1×PBS/PS was administered intranasally into mice anesthetized with ketamine/xylazine. 48 hours after infection, the lungs were harvested and homogenized in 600 uL 0.3% BSA/1×PBS/PS. The homogenates were frozen and thawed twice to release the virus. A TCID50 assay (Tissue-Culture Infectious Dose 50) was performed to titer virus in lung homogenates. Flat-bottom, 96-well plates were seeded with $2\times10^4$ MDCK cells per well, and 24 hours later, the serum-containing medium was removed. 30 uL of lung homogenates, either undiluted or diluted from 10- to $10^7$-fold (in 10-fold steps), was added into quadruplicate wells. After incubation for 1 hr, 170 µl of infection medium (DMEM/0.3% BSA/10 mM HEPES/PS) containing 4 g/ml trypsin was added to each well. After incubation for 48 hours at 37° C., the presence or absence of virus in the culture supernatants was determined by hemagglutination of chicken red blood cells. The virus titers were estimated using the Spearman and Karber formula.

Example SYBR™ Gold Assay for siRNA Concentrations

The concentration of dsRNA in a formulation can be determined by SYBR™ Gold assay as follows: 10 ul of dsRNA formulation is added to 100 ul MeOH and incubated for 5 minutes at 55° C. 50 ul Heparin (200 mg/ml) is added, and the solution is incubated for 5 minutes at 55° C. 790 ul PBS (phosphate buffered saline) is added, and the sample is spun down in microfuge to pelletize. A 90 ul sample of the pellet is incubated with 10 ul SYBR™ Gold reagent (Molecular Probes, Eugene, Oreg.). Fluorescence is read at Em 535 nm with excitation at 495 nm.

Example RNA Isolation and Quantitative RT-PCR Assay for Knockdown of ApoB Message For this housekeeping gene protocol, pulmonary or systemic, on Day 1 C57/B6 or Balb/C female mice age 8-10 weeks (5 mice per group) were dosed with 50 ul or 200 uL of dsRNA formulation by intranasal or intravenous route of administration, respectively. Anesthetic was ketamine/xylazine (IP—0.2 ml dose/mouse). On Day 2 whole lung was isolated from mice either 1 day post dosing or next day following 3 consecutive days of dosing for pulmonary model or lung, liver, kidney, spleen, heart and/or whole blood for systemic model. Tissues were placed in a 24 well plate containing 2 ml RNALATER RNA Stabilization Reagent (Qiagen 76106). Plates were placed on dry ice to freeze immediately, and stored at −80° C. until homogenate was prepared.

Total RNA was extracted from tissue samples stored in RNALATER solution at the time of necropsy. The isolation of total RNA was done using the Invitrogen PURELINK 96 RNA Isolation Kit according to the manufacturer's protocol for the isolation of mammalian tissue. These total RNA isolates were then quantified using the NanoDrop spectrophotometer, and then quality was assured using the Agilent Bioanalyzer 2100 system to determine RNA integrity. After the quality and quantity of the total RNA was determined, the samples were normalized to equal concentrations and 50-100 ng of total RNA was synthesized into cDNA using the Applied Biosystems High Capacity cDNA Archive Kit according to the manufacturer's protocol. The cDNA was then rechecked for concentration using the Nanodrop and then diluted 1:10 for qRT-PCR analysis.

The gene expression analysis using qRT-PCR was done using the cDNA samples and SYBR green technology with final primer concentrations of 200 nM. The samples were run using the Quanta PerfectCta SYBR Green FastMix, ROX using a 10 µL reaction volume. The samples were run using a 384-well plate format on the Applied Biosystems 7900HT platform using fast cycling conditions. Data was then exported from the SDS 2.3 software using a threshold value of 0.2. These were formatted for analysis using QBASE software of algorithms entered by the user into Excel. Genes chosen for endogenous controls were based on geNorm analysis. For mouse liver samples GAPDH and PPIA and TBP have been shown to be very good stable normalizers for gene expression analysis.

Serum Cholesterol Assay

The purpose of this assay was to ascertain the blood serum cholesterol levels in mouse blood 48 hours after dosing with a dsRNA. Invitrogen Amplex Red Cholesterol Assay Kit (cat#A12216) was used. Mouse whole blood was drawn and placed in Serum Separator Tubes (SST-BD cat #365956), then centrifuged to separate the serum from the rest of the blood. The serum was diluted in DI-$H_2O$ 1:40, then diluted a further 1:5 (total of 1:200) in the 1× Reaction buffer from the Amplex assay kit. Standards were made from the cholesterol reference standard, supplied with the kit, at concentrations of 20 ug/ml, 10 ug/ml, 8 ug/ml, 6 ug/ml, 4 ug/ml, 2 ug/ml and 1 ug/ml. Samples, standards and blanks were added to a flat bottomed black 96-well plate (Costar Catalogue #3916). The Amplex assay mixture was made and added to the assay wells. After at least 30 minutes of incubation at 37° C., the plate was read using the Molecular Devices SpectraMax M5. The "End point" protocol was selected, and the excitation range was set for 530-560 (preferably 544 nM), and the emission detection at ~590. Once the plate was read the data was exported to excel, where the Percent control, percent reduction and total blood serum cholesterol in ug/ml was calculated.

Example 27

The structures of some double-stranded RNAs (dsRNA) of this disclosure are shown in Table 1.

TABLE 1

Double-stranded RNAs

| RNA | SEQUENCES |
|---|---|
| DX4227 ApoB | (SEQ ID NO: 7) Sense 5'-GGAAUC$_m$U$_m$UA$_m$UA$_m$U$_m$U$_m$UGAUC$_m$CAsA-3' (SEQ ID NO: 8) Antisense 5'-$_m$U$_m$UGGAU$_m$CAAA$_m$UA$_m$UAAGA$_m$UUC$_m$Cs$_m$CsU-3' |
| DX3030 Influenza | (SEQ ID NO: 9) Sense 5'-GGAUCUUAUUUCUUCGGAGACAAdTdG-3' (SEQ ID NO: 10) Antisense 5'-CAUUGUCUCCGAAGAAAUAAGAUCCUU-3' |
| DX2816 Non-target Qneg | (SEQ ID NO: 11) Sense 5'-UUCUCCGAACGUGUCACGUdTdT-3' (SEQ ID NO: 12) Antisense 5'-ACGUGACACGUUCGGAGAAdTdT-3' |
| DX2940 LacZ | (SEQ ID NO: 13) Sense 5'-CUACACAAAUCAGCGAUUUdTdT-3' (SEQ ID NO: 14) Antisense 5'-AAAUCGCUGAUUUGUGUAGdTdC-3' |
| DX2742 PPIB MoCypB | (SEQ ID NO: 15) Sense 5'-GGAAAGACUGUUCCAAAAAUU-3' (SEQ ID NO: 16) Antisense 5'-UUUUUGGAACAGUCUUUCCUU-3' |
| DX 2744 G1498 influenza | (SEQ ID NO: 17) Sense 5'-GGAUCUUAUUUCUUCGGAGdTdT-3' (SEQ ID NO: 18) Antisense 5'-CUCCGAAGAAAUAAGAUCCdTdT-3' |
| DX 2918 Inm4 TNFa modified | (SEQ ID NO: 19) Sense 5'-CCGTCAGCCGATTTGCTATTT-3' (SEQ ID NO: 20) Antisense 5'-p-AUAGCAAATCGGCTGACGGTT-3' |

In Table 1, "mU" represents 2'-O-methyl uridine, "mC" represents 2'-O-methyl cytidine, and "s" represents a phosphorothioate linkage.

Example 28

Active RNA formulations of this disclosure can be prepared by dissolving an interfering RNA in buffer or cell culture medium and vortexing, separately admixing a delivery formulation with buffer or cell culture medium and vortexing, and finally admixing the interfering RNA mixture with the delivery formulation mixture to make an active RNAi transfection formulation.

To prepare a delivery formulation, amino acid lipids along with other lipids and/or excipients can be solubilized in $CHCl_3$/MeOH, dried down under $N_2$, and hydrated in 10 mM HEPES with 5% dextrose at pH 7.4. The mixture can be sonicated, or extruded, dialyzed, and/or tangential flow filtered.

Various dilution methods known in the art can also be used to prepare active RNA formulations of this disclosure.

An exemplary interfering RNA formulation of this disclosure is shown in Table 2. In this example, the amino acid lipid designated C8-Arg-C8 provides its own formulation for intracellular delivery of an interfering siRNA therapeutic. The amount of amino acid lipid is given as the mole percentage of delivery components, not including the active RNA agent. The designation "C16-Arg-C14" refers to (C15alkyl)-(C=O)-Arg-NH—(C14alkyl) which is the same as (C16acyl)-Arg-NH—(C14alkyl).

TABLE 2 dsRNA Formulation

| Component | Amount |
|---|---|
| dsRNA | 50 nM |
| C16-Arg-C14 amino acid lipid | 100 mole % |

An exemplary interfering RNA formulation of this disclosure is shown in Table 3. In this example, the amino acid lipid designated C14-norArg-C14 provides its own formulation for intracellular delivery of an interfering siRNA therapeutic. The amount of amino acid lipid is given as the mole percentage of delivery components, not including the active RNA agent. The designation "C14-norArg-C14" refers to (C13alkyl)-(C=O)-norArg-NH—(C14alkyl) which is the same as (C14acyl)-norArg-NH—(C14alkyl).

TABLE 3 dsRNA Formulation

| Component | Amount |
|---|---|
| dsRNA | 50 nM |
| C14-norArg-C14 amino acid lipid | 100 mole % |

An exemplary RNAi formulation of this disclosure is shown in Table 4. In this example, the amino acid lipid designated C10-norArg-C10 is combined with a non-cationic lipid in a co-delivery formulation. The designation "C10-norArg-C10" refers to (C9alkyl)-(C=O)-norArg-NH—(C10alkyl) which is the same as (C10acyl)-norArg-NH—(C12alkyl).

TABLE 4 dsRNA Formulation

| Component | Amount |
|---|---|
| dsRNA DX3030 | 50 nM |
| C10-norArg-C10 amino acid lipid | 50 mole % |
| DOPE | 50 mole % |

An exemplary RNAi formulation of this disclosure is shown in Table 5. In this example, the amino acid lipid designated C12-homoArg-C12 is combined with a cationic lipid, a non-cationic lipid, and a pegylated lipid in a multi-component delivery formulation. The designation "C12-homoArg-C12" refers to (C11 alkyl)-(C=O)-homoArg-NH—(C12alkyl) which is the same as (C12acyl)-homoArg-NH—(C14alkyl).

TABLE 5 dsRNA Formulation

| Component | Amount |
|---|---|
| dsRNA | 25 nM |
| C12-norArg-C12 | 30 mole % |
| DSPC | 20 mole % |
| Cholesterol | 49 mole % |
| DSPE-PEG2000 | 1 mole % |

An exemplary interfering-RNA emulsion composition of this disclosure is shown in Table 6. In this example, the cationic amino acid lipid is designated C14-norArg-C14.

TABLE 6 dsRNA Emulsion

| Component | Amount |
|---|---|
| dsRNA | 25 nM, N/P 4 |
| C14-norArg-C14 | 11% (w/w of oil phase); |
| dioleoylphosphatidylethanolamine | 1:1 molar ratio of cationic lipid to emulsifier |
| LABRAFAC PG | 89% (w/w of oil phase) |
| water | 80% |

An exemplary interfering-RNA dispersion composition of this disclosure is shown in Table 7. In this example, the cationic amino acid lipid is designated C14-norArg-C14.

TABLE 7 dsRNA Dispersion Composition

| Component | Amount |
|---|---|
| dsRNA | 25 nM, N/P 4 |
| C14-norArg-C14 | 12% (w/w of lipid/dispersant phase) |
| LABRASOL | 88% (w/w of lipid/dispersant phase) |
| water | 80% |

Example 29

Example liposomal formulations of interfering RNA compositions of this disclosure are shown in Table 8.

TABLE 8

Example Formulations
Composition (mol %)

| | |
|---|---|
| C18-norArg(NH$_3$Cl)-C18/DSPE-PEG2k/DSPC/chol. | (30; 1; 20; 49) |
| C16-norArg(NH$_3$Cl)-C16/DSPE-PEG2k/DSPC/chol. | (30; 1; 20; 49) |
| C14-norArg(NH$_3$Cl)-C14/DMPE-PEG2k/DSPC/chol. | (30; 1; 20; 49) |
| C12-Arg(NH$_3$Cl)-C12/DSPE-PEG2k/DSPC/chol. | (30; 1; 20; 49) |
| C10-Arg(NH$_3$Cl)-C10/DSPE-PEG2k/DSPC/chol. | (30; 1; 20; 49) |
| C8-Arg(NH$_3$Cl)-C8/DSPE-PEG2k/DSPC/chol. | (30; 1; 20; 49) |
| C10-D-Arg(NH$_3$Cl)-C18/DSPE-PEG2k/DSPC/chol. | (30; 1; 20; 49) |
| C12-D-Arg(NH$_3$Cl)-C16/DPPE-PEG5k/DSPC/chol. | (30; 1; 20; 49) |
| C14-D-Arg(NH$_3$Cl)-C14/DSPE-PEG2k/DSPC/chol. | (30; 1; 20; 49) |
| C16-homoArg(NH$_3$Cl)-C12/DSPE-PEG2k/DSPC/chol. | (30; 1; 20; 49) |
| C18-homoArg(NH$_3$Cl)-C10/DMPE-PEG5k/DSPC/chol. | (30; 1; 20; 49) |
| C12-homoArg(NH$_3$Cl)-C12/DSPE-PEG2k/DSPC/chol. | (30; 1; 20; 49) |
| C14-nornorArg(NH$_3$Cl)-C14/DSPE-PEG2k/DSPC/chol. | (30; 1; 20; 49) |
| C16-nornorArg(NH$_3$Cl)-C16/DSPE-PEG2k/DSPC/chol. | (30; 1; 20; 49) |

Example 30

Particle Size of RNA Delivery Compositions

Examples of liposomal amino acid lipid interfering RNA formulations are shown in Table 9. The formulations of Table 9 each had an N/P of 1.8 and exhibited particle sizes from 106-139 nm with dispersity values of about 0.08 to 0.19.

TABLE 9

Particle Size of RNA Delivery Compositions

| Composition (mol %) | N/P | Particle Size (nm) | PDI |
|---|---|---|---|
| C12-norArg(NH$_3$Cl)-C12/DSPE-PEG2k/DSPC/CHOL (30; 1; 20; 49) | 1.8 | 139 | 0.19 |
| C12-Arg(NH$_3$Cl)-C12/DSPE-PEG2k/DSPC/CHOL (30; 1; 20; 49) | 1.8 | 106 | 0.08 |
| C12-D-Arg(NH$_3$Cl)-C12/DSPE-PEG2k/DSPC/CHOL (30; 1; 20; 49) | 1.8 | 112 | 0.19 |
| C12-homoArg(NH$_3$Cl)-C12/DSPE-PEG2k/DSPC/CHOL (30/1/20/49) | 1.8 | 119 | 0.15 |

Examples of amino acid lipid interfering RNA formulations are shown in Table 10. The formulations of Table 10 had N/P ratios of from 1.5 to 1.9 and exhibited particle sizes from 140-148 nm with dispersity values of about 0.18 to 0.30.

TABLE 10

Particle Size of RNA Delivery Compositions

| Composition | N/P | Particle Size (nm) | PDI |
|---|---|---|---|
| C12-nor-Arg(NH$_3$Cl)-C12/DSPE-PEG2k/DSPC/CHOL (30/1/20/49) | 1.51 | 148.3 | 0.18 |
| C12-Arg(NH$_3$Cl)-C12/DSPE-PEG2k/DSPC/CHOL (30/1/20/49) | 1.51 | 148.3 | 0.18 |
| C12-D-Arg(NH$_3$Cl)-C12/DSPE-PEG2k/DSPC/CHOL (30/1/20/49) | 1.51 | 148.3 | 0.18 |
| C12-homoArg(NH$_3$Cl)-C12/DSPE-PEG2k/DSPC/CHOL (30/1/20/49) | 1.89 | 140.3 | 0.30 |

A transmission electron micrograph obtained on a JEOL 1230 TEM of a liposomal embodiment of this invention is shown in FIG. 2. FIG. 2 shows spherical lipid bilayer vesicle particles formed with the amino acid lipid C12-norArg-C12. The length marker of the micrograph is 0.5 micrometer, and the sample was stained with 3% uranyl acetate. The lipid portion of the liposomal formulation was [C12-norArg(NH$_3^+$Cl$^-$)—C12/DSPC/cholesterol/DSPE-PEG-2000] in the amounts of [30%/20%/49%/1%] respectively, as a percent weight/weight of total lipid. The liposomes contained the antiinfluenza-active dicer substrate dsRNA DX3030.

Example 31

LacZ Gene Knockdown Activity In Vitro for Amino Acid Lipid RNAi Binary Compositions Amino acid lipids provided effective interfering-RNA delivery composition as shown in Table 11 by a LacZ activity-based in vitro assay. The results in Table 11 showed that gene knockdown by an interfering-RNA in an amino acid lipid composition can exceed that obtained with RNAIMAX (Invitrogen).

TABLE 11

LacZ Knockdown for Amino Acid Lipid Interfering
RNA Formulations

| Composition | % Knockdown vs. Qneg |
|---|---|
| C8-norArg-C8:DOPE (1:1) | 88 |
| C10-norArg-C10:DOPE (1:1) | 89 |
| C12-norArg-C12:DOPE (1:1) | 88 |
| C8-L-Arg-C8:DOPE (1:1) | 16 |
| C10-L-Arg-C10:DOPE (1:1) | 82 |
| C12-L-Arg-C12:DOPE (1:1) | 100 |
| C8-D-Arg-C8:DOPE (1:1) | 40 |
| C10-D-Arg-C10:DOPE (1:1) | 82 |
| C12-D-Arg-C12:DOPE (1:1) | 80 |
| C8-homoArg-C8:DOPE (1:1) | 52 |
| C10-homoArg-C10:DOPE (1:1) | 100 |
| C12-homoArg-C12:DOPE (1:1) | 51 |
| C8-nornorArg-C8:DOPE (1:1) | 78 |
| C10-nornorArg-C10:DOPE (1:1) | 78 |
| C8-norArg-C8:DPhPE (1:1) | 43 |
| C10-norArg-C10:DPhPE (1:1) | 73 |
| RNAI-MAX | 92 |

In Table 11, the final concentration of dsRNA was 100 nM and the N/P ratio was 1.8 for each composition.

Example 32

LacZ Gene Knockdown In Vitro for Amino Acid Lipid RNAi Liposomal Compositions Amino acid lipids provided effective interfering-RNA delivery compositions as shown in Table 12 by a LacZ activity-based in vitro assay.

TABLE 12

Normalized LacZ Gene Knockdown for Amino Acid
Lipid RNAi Compositions

| Composition | % Knockdown |
|---|---|
| C12-norArg(NH$_3$Cl)-C12/DPhPE/DSPE-PEG (50/49/1) | 60 |
| C12-Arg(NH$_3$Cl)-C12/DPhPE/DSPE-PEG (50/49/1) | 94 |
| C12-D-Arg(NH$_3$Cl)-C12/DPhPE/DSPE-PEG (50/49/1) | 86 |
| C12-homoArg(NH$_3$Cl)-C12/DPhPE/DSPE-PEG (50/49/1) | 81 |
| RNAIMAX | 82 |

The normalized LacZ knockdown results in Table 12 showed that at least 60% knockdown was observed for all amino acid lipid compositions. The results in Table 12 showed that gene knockdown by an interfering-RNA in an amino acid lipid composition can exceed that obtained with RNAIMAX.

Example 33

Gene Knockdown Concentration Response In Vitro for Amino Acid Lipid RNAi Compositions Gene knockdown activity for several ternary amino acid lipid RNAi compositions was determined in vitro.

Amino acid lipids provided efficacious interfering-RNA delivery composition as shown in FIG. 3 by a PPIB knockdown activity-based in vitro assay in A549 cells. The results in FIG. 3 showed that gene knockdown by an interfering-RNA in an amino acid lipid composition, as represented by normalized PPIB values, can exceed that obtained with RNAIMAX.

In FIG. 3 is shown the concentration response of the normalized PPIB values for two amino acid lipid formulations compared to results for RNAIMAX. Formulation 1 in FIG. 3 was [C12-norArg(NH$_3$Cl)—C12/DOPE/CHOL (50/32/18)] and Formulation 2 was [C12-norArg(NH$_3$Cl)—C12/CHEMS/DLPE (50/32/18)].

Amino acid lipids provided efficacious interfering-RNA delivery composition as shown in FIG. 4 by a LacZ knockdown activity-based in vitro assay in 9L cells. The results in FIG. 4 showed that gene knockdown by an interfering-RNA in an amino acid lipid composition, as represented by normalized beta-galactosidase values, can exceed that obtained with RNAIMAX.

In FIG. 4 is shown the concentration response of the normalized beta-galactosidase values for two amino acid lipid formulations compared to results for RNAIMAX. Formulation 1 in FIG. 4 was [C12-norArg(NH$_3$Cl)—C12/DOPE/CHOL (50/32/18)] and Formulation 2 was [C12-norArg(NH$_3$Cl)—C12/CHEMS/DLPE (50/32/18)].

The gene knockdown activity data in vitro for several amino acid lipid formulations containing three lipid components are summarized in Table 13.

TABLE 13

Gene Knockdown for Amino Acid Lipid RNAi Compositions In vitro

| Formulation | dsRNA (nM) | % Knockdown (vs QNeg) A549 PPIB | 9L LacZ |
|---|---|---|---|
| C12norArgC12/CHEMS/chol. (50/32/18) (N/P = 1.8) | 25 | 85 | 95 |
|  | 10 | 74 | 74 |
|  | 1 | 9 | 49 |
| C12norArgC12/DOPE/chol. (50/32/18) (N/P = 5.0) | 25 | 92 | 97 |
|  | 10 | 93 | 91 |
|  | 1 | 34 | 30 |
| C12norArgC12/CHEMS/DLPE (50/32/18) (N/P = 1.8) | 25 | 98 | 97 |
|  | 10 | 97 | 94 |
|  | 1 | 23 | 39 |
| C12norArg/chol./DLPE (50/32/18) (N/P = 5.0) | 25 | 78 | 83 |
|  | 10 | 43 | 57 |
|  | 1 | 2 | 24 |
| RNAIMAX | 25 | 87 | 89 |
|  | 10 | 42 | 67 |
|  | 1 | 7 | 16 |

As shown in Table 13, the results obtained at a concentration of 10 nM dsRNA showed that these exemplary amino acid lipid formulations containing C12-norArg-C12 provided gene knockdown activity in vitro that exceeded results obtained with RNAIMAX.

The gene knockdown activity data in vitro for some amino acid lipid formulations containing three lipid components obtained with and without serum present (fetal bovine serum) are summarized in Table 14.

TABLE 14

PPIB gene knockdown for amino acid lipid RNAi compositions
in vitro with and without serum

| Formulation | N:P | dsRNA (nM) | % Knockdown (vs Qneg) w/Serum | w/oSerum |
|---|---|---|---|---|
| C12-norArg-C12/CHEMS/chol. | 4 | 25 | 94 | 91 |
|  | 4 | 2.5 | 69 | 83 |
|  | 4 | 0.25 | 42 | 23 |

TABLE 14-continued

PPIB gene knockdown for amino acid lipid RNAi compositions
in vitro with and without serum

| Formulation | N:P | dsRNA (nM) | % Knockdown (vs Qneg) w/Serum | % Knockdown (vs Qneg) w/oSerum |
|---|---|---|---|---|
| C12-norArg-C12/CHEMS/chol. | 4 | 25 | 96 | 95 |
|  | 4 | 2.5 | 95 | 96 |
|  | 4 | 0.25 | 65 | 47 |
| RNAIMAX | — | 25 | 98 | 97 |
| (fixed amount per | — | 2.5 | 97 | 94 |
| preparation) | — | 0.25 | 56 | 48 |

As shown in Table 14, exemplary amino acid lipid formulations containing C12-norArg-C12 provided high PPIB gene knockdown activity in vitro with and without serum present. These amino acid lipid formulations were made by various rehydration and dilution methods.

The gene knockdown activity data in vitro for some amino acid lipid formulations containing three and four lipid components are summarized in Table 15.

TABLE 15

LacZ Gene Knockdown (KD) for Amino Acid Lipid
RNAi Compositions in vitro

| Composition | % (w/w) of lipids | dsRNA (nM) | % KD vs Qneg 9L/LacZ |
|---|---|---|---|
| C18:1-His(1-Me)-C16/C18:1-norArg-C16/chol. | 8/42/50 | 25 | 90 |
|  |  | 5 | 83 |
|  | 16/32/50 | 25 | 91 |
|  |  | 5 | 94 |
| C18:1-His(1-Me)-C16/C18:1-norArg-C16/chol. | 8/42/50 | 25 | 94 |
|  |  | 5 | 90 |
|  | 16/32/50 | 25 | 91 |
|  |  | 5 | 91 |
| C18:1-norArg-C16/CHEMS/chol. | 50/32/18 | 25 | 43 |
|  |  | 5 | 56 |
|  | 50/32/18 | 25 | 72 |
|  |  | 5 | 73 |
| C18:1-norArg-C12/CHEMS/chol. | 50/32/18 | 25 | 90 |
|  |  | 5 | 92 |
| C18:1-norArg-C8/CHEMS/chol. | 50/32/18 | 25 | 92 |
|  |  | 5 | 95 |
| C18:2-norArg-C16/CHEMS/chol. | 50/32/18 | 25 | 90 |
|  |  | 5 | 33 |
|  | 50/20/30 | 25 | 92 |
|  | 50/24/26 | 25 | 93 |
|  | 50/28/22 | 25 | 92 |
| C18:1-norArg-C16/CHEMS/chol./DSPC | 40/16/34/10 | 25 | 79 |
|  | 40/19/31/10 | 25 | 82 |
|  | 40/22/28/10 | 25 | 82 |
|  | 40/26/24/10 | 25 | 88 |
| C18:1-Pal-C16/C18:1-norArg-C16/chol. | 4/46/50 | 25 | 72 |
|  | 8/42/50 | 25 | 77 |
|  | 16/32/50 | 25 | 88 |
|  | 32/16/50 | 25 | 91 |

As shown in Table 15, some amino acid lipid formulations containing three and four components provided high 9L/LacZ gene knockdown activity in vitro. High 9L/LacZ knockdown activity was observed for formulations using a mixture of amino acid lipids, and for formulations having CHEMS or cholesterol as an additional lipid.

Example 34

ApoB Gene Knockdown Concentration Response
In Vitro for Amino Acid Lipid RNAi Compositions ApoB gene knockdown activity for several four-component amino acid lipid RNAi compositions was determined in vitro.

In FIG. 5 is shown an example of ApoB gene knockdown activity obtained from an in vitro assay in HepG2 cells. The concentration response at 25, 2.5, and 0.25 nM RNA of the normalized ApoB mRNA expression values for three amino acid lipid formulations of an interfering-RNA are shown. Formulation 1 was [non-amino acid cationic lipid/DSPC/chol./DMPE-PEG2k (40/10/48/2)]. Formulation 2 and 3 were both [C18:1-norArg-C16/CHEMS/DLPE/DMPE-PEG2k (50/32/16/2)].

The ApoB dsRNA was DX4227 (ApoB-2 P2098).

A concentration response was obtained for percent ApoB mRNA expression knockdown in HepG2 cells. For the HepG2 cell screen the protocol was as follows: On Day 1 the HepG2 cells were refreshed with fresh growth medium containing 10% FBS, 1x non-essential amino acid, and 0.125% sodium bicarbonate in DMEM. On Day 2, 25 microL of the complex was added to the wells, then 75 microL of HepG2 single cell suspension in OPTIMEM was added to the wells (15000 cells/well). After 4 hours, 100 ul DMEM with 20% FBS was added to each well. On Day 3 at 24 hours the cells were lysed, the RNA was prepared, and qRT-PCR was performed for ApoB and rGAPDH mRNA.

The ApoB gene knockdown activity for several four-component amino acid lipid RNAi compositions is summarized in Table 16.

TABLE 16

ApoB Gene Knockdown for Amino Acid
Lipid RNAi Compositions in vitro

| Composition | N/P pH 7.4 | N/P pH 5.0 | % Knockdown vs UNT 100 nM | % Knockdown vs UNT 25 nM | % Knockdown vs UNT 2.5 nM | % Knockdown vs UNT 0.25 nM |
|---|---|---|---|---|---|---|
| C18:1-norArg-C16/CHEMS/DLPE/DMPE-PEG2k (50/32/16/2) | 1.8 | 4.9 | 84 | 93 | 36 | 0 |
| C18:1-norArg-C16/CHEMS/DMPE/DMPE-PEG2k (50/32/16/2) | 0.8 | 2.1 | 94 | 84 | 0 | 0 |
| C18:1-norArg-C16/CHEMS/DPPE/DMPE-PEG2k (50/32/16/2) | 0.8 | 2.1 | 96 | 82 | 19 | 0 |
| C18:1-norArg-C16/CHEMS/DPLC/DMPE-PEG2k (50/32/16/2) | 0.8 | 2.1 | 96 | 89 | 0 | 0 |
| C18:1-norArg-C16/CHEMS/DSPC/DMPE-PEG2k (50/32/16/2) | 0.8 | 2.1 | 94 | 89 | 37 | 0 |
| C18:1-norArg-C16/CHEMS/DLPE/DMPE-PEG2k (50/32/16/2) | 0.8 | 2.1 | 95 | 82 | 13 | 13 |
| RNAIMAX | — | — | 87 | 24 | 24 | |

Example 35

ApoB Gene Knockdown In Vivo for Amino Acid
Lipid RNAi Compositions

ApoB gene knockdown activity for some three- and four-component amino acid lipid RNAi compositions was determined in vivo mouse. The ApoB mRNA reduction activity in vivo is shown in Table 17.

TABLE 17

ApoB Gene Knockdown for Amino Acid Lipid RNAi Compositions in vivo

| Composition | % Knockdown In Vivo |
|---|---|
| C18:1-norArg-C16/CHEMS/DLPE/DMPE-PEG2k (50/32/16/2) | 88 |
| C18:1-norArg-C16/chol./DMPE-PEG2k (50/48/2) | 45 |
| C18:1-norArg-C16/CHEMS/chol./DMPE-PEG2k (50/15/33/2) | 46 |
| C18:1-norArg-C16/CHEMS/chol./DMPE-PEG2k (50/32/16/2) | 88 |

The ApoB gene knockdown dose response in vivo mouse was obtained for several four-component amino acid lipid RNAi compositions and compared to mouse serum cholesterol levels. The ApoB mRNA reduction and corresponding serum cholesterol reduction in vivo is summarized in Table 18.

TABLE 18

ApoB Gene Knockdown (KD) Dose Response for Amino Acid Lipid RNAi Compositions in vivo

| Composition | ApoB mRNA % KD (ApoB 9133) | ApoB mRNA % KD (ApoB 12211) | % Change in serum cholesterol (+/− gain/loss) |
|---|---|---|---|
| C18:1-norArg-C16/CHEMS/DLPE/DMPE-PEG2k (50/32/16/2) (N/P 1.8, 2 mg/kg) | 72.0 | 72.6 | −7.1 |
| C18:1-norArg-C16/CHEMS/DLPE/DMPE-PEG2k (50/32/16/2) (N/P 1.8, 1 mg/kg) | 35.2 | 39.6 | −4.0 |
| C18:1-norArg-C16/CHEMS/DLPE/DMPE-PEG2k (50/32/16/2) (N/P 1.8, 0.5 mg/kg) | 17.6 | 20.6 | 10.6 |
| C18:1-norArg-C16/CHEMS/DLPE/DMPE-PEG2k (50/32/16/2) (N/P 0.8, 4 mg/kg) | 69.9 | 70.6 | −38.9 |
| C18:1-norArg-C16/CHEMS/DLPE/DMPE-PEG2k (50/32/16/2) (N/P 0.8, 2 mg/kg) | 46.3 | 47.8 | −14.5 |
| PBS | — | 1.2 | 0 |

Example 36

Antiviral Effects for Amino Acid Lipid RNAi Compositions

Examples of amino acid lipid interfering RNA formulations having four components are shown in Table 19. The formulations of Table 19 were used to demonstrate anti-viral activity in vivo in a mouse influenza model.

TABLE 19

Example RNA Delivery and Comparative Formulations

| Group | Composition | dsRNA | dsRNA dose (amt/kg/day) mg | dsRNA dose (amt/kg/day) nmol | Lipid dose (μmol/kg/day) |
|---|---|---|---|---|---|
| 1 | C12-norArg(NH$_3^+$Cl$^-$)-C12/DSPE-PEG2k/DSPC/chol. (30; 1; 20; 49) | DX3030 | 2 | 120 | 36 |
| 2 | C12-norArg(NH$_3^+$Cl$^-$)-C12/DSPE-PEG2k/DSPC/chol. (30; 1; 20; 49) | Qneg DX2816 | 1.6 | 120 | 28.8 |
| 3 | C14-norArg (NH$_3^+$Cl$^-$)-C14/DSPE-PEG2k/DSPC/chol. (30; 1; 20; 49) | DX3030 | 2 | 120 | 36 |
| 4 | C14-norArg (NH$_3^+$Cl$^-$)-C14/DSPE-PEG2k/DSPC/chol. (30; 1; 20; 49) | Qneg DX2816 | 1.6 | 120 | 28.8 |
| 5 | C16-norArg (NH$_3^+$Cl$^-$)-C16/DSPE-PEG2k/DSPC/chol. (30; 1; 20; 49) | DX3030 | 2 | 120 | 36 |
| 6 | C16-norArg (NH$_3^+$Cl$^-$)-C16/DSPE-PEG2k/DSPC/chol. (30; 1; 20; 49) | Qneg DX2816 | 1.6 | 120 | 28.8 |
| 7 | C18-norArg (NH$_3^+$Cl$^-$)-C18/DSPE-PEG2k/DSPC/chol. (30; 1; 20; 49) | DX3030 | 2 | 120 | 36 |
| 8 | C18-norArg (NH$_3^+$Cl$^-$)-C18/DSPE-PEG2k/DSPC/chol. (30; 1; 20; 49) | Qneg DX2816 | 1.6 | 120 | 28.8 |
| 9 | C18oleic-norArg(NH$_3^+$Cl$^-$)-C16/DSPE-PEG2k/DSPC/chol. (30; 1; 20; 49) | DX3030 | 2 | 120 | 36 |
| 10 | C18oleic-norArg(NH$_3^+$Cl$^-$)-C16/DSPE-PEG2k/DSPC/chol. (30; 1; 20; 49) | Qneg DX2816 | 1.6 | 120 | 28.8 |
| 11 | C12-norArg(NH$_3^+$Cl$^-$)-C12/DSPE-PEG2k/DSPC/chol. (30; 1; 20; 49) | NONE | — | — | 36 |
| 12 | PBS | — | — | — | — |

The formulations of Table 19 each had an N/P of 1.8 and exhibited particle sizes from 127-183 nm (excepting Groups 7-8) with dispersity values of about 0.1 to 0.3, as shown in Table 20.

TABLE 20

Characterization of RNA Delivery and Comparative Formulations

| Group | Composition | N/P | Size (nm) | PDI |
|---|---|---|---|---|
| 1 | C12-norArg(NH$_3^+$Cl$^-$)-C12/DSPE-PEG2k/DSPC/chol. (30; 1; 20; 49) | 1.8 | 151.1 | 0.315 |
| 2 | C12-norArg(NH$_3^+$Cl$^-$)-C12/DSPE-PEG2k/DSPC/chol. (30; 1; 20; 49) | 1.8 | 128 | 0.134 |
| 3 | C14-norArg (NH$_3^+$Cl$^-$)-C14/DSPE-PEG2k/DSPC/chol. (30; 1; 20; 49) | 1.8 | 144.5 | 0.201 |
| 4 | C14-norArg (NH$_3^+$Cl$^-$)-C14/DSPE-PEG2k/DSPC/chol. (30; 1; 20; 49) | 1.8 | 126.6 | 0.114 |
| 5 | C16-norArg (NH$_3^+$Cl$^-$)-C16/DSPE-PEG2k/DSPC/chol. (30; 1; 20; 49) | 1.8 | 182.8 | 0.141 |
| 6 | C16-norArg (NH$_3^+$Cl$^-$)-C16/DSPE-PEG2k/DSPC/chol. (30; 1; 20; 49) | 1.8 | 174 | 0.157 |
| 7 | C18-norArg (NH$_3^+$Cl$^-$)-C18/DSPE-PEG2k/DSPC/chol. (30; 1; 20; 49) | 1.8 | 977.4 | 1 |
| 8 | C18-norArg (NH$_3^+$Cl$^-$)-C18/DSPE-PEG2k/DSPC/chol. (30; 1; 20; 49) | 1.8 | 625 | 0.925 |

TABLE 20-continued

Characterization of RNA Delivery and Comparative Formulations

| Group | Composition | N/P | Size (nm) | PDI |
|---|---|---|---|---|
| 9 | C18oleic-norArg($NH_3^+Cl^-$)-C16/ DSPE-PEG2k/DSPC/chol. (30; 1; 20; 49) | 1.8 | 139.3 | 0.155 |
| 10 | C18oleic-norArg($NH_3^+Cl^-$)-C16/ DSPE-PEG2k/DSPC/chol. (30; 1; 20; 49) | 1.8 | 130.2 | 0.109 |

The degrees of viral titer reduction for the formulations of Table 19 are shown in Table 21. Each value for viral titer reduction reflects data for eight mice.

TABLE 21

Viral Titer Reduction for RNAi Delivery Formulations

| Group | dsRNA | Fold Reduction in Viral Titer Compared to PBS control (averages) | Fold Reduction in Viral Titer Compared to PBS control (medians) | p value |
|---|---|---|---|---|
| 1 | DX3030 | 165.0 | 1698.0 | 0.0002 |
| 2 | Qneg DX2816 | 2.1 | 2.3 | 0.034 |
| 3 | DX3030 | 25.3 | 100.0 | 0.002 |
| 4 | Qneg DX2816 | 3.8 | 5.6 | 0.008 |
| 5 | DX3030 | 13.8 | 17.8 | 0.0003 |
| 6 | Qneg DX2816 | 6.3 | 6.7 | 0.002 |
| 7 | DX3030 | 26.7 | 31.6 | 0.001 |
| 8 | Qneg DX2816 | 2.6 | 5.6 | 0.037 |
| 9 | DX3030 | 25.7 | 22.8 | 0.0002 |
| 10 | Qneg DX2816 | 20.0 | 17.8 | 0.0003 |

In general, the results in Table 21 showed that the interfering-RNA amino acid lipid formulations delivered the interfering-RNA to cells in vivo, whereby influenza viral titer was reduced by up to about 1600-fold or greater, relative to PBS as control. Control Groups were #2, 4, 6, 8, and 10, which were dosed with Qneg.

What is claimed is:

1. A compound comprising the structure shown in Formula I:

$$R^3-(C=O)\text{-Xaa-Z}-R^4 \qquad \text{Formula I}$$

wherein
  Xaa is tyrosine or 3,5-diiodo-tyrosine;
  $R^3$ is independently a substituted or unsubstituted C(12-22)alkenyl;
  $R^4$ is independently a substituted or unsubstituted C(12-22)alkyl or C(12-22)alkenyl;
  Z is NH;
and salts thereof.

2. The compound of claim 1, wherein $R^3$ and $R^4$ are C(12-22)alkenyl and are the same or different.

3. The compound of claim 1, wherein $R^4$ is C(12-22)alkyl and $R^3$ is C(12-22)alkenyl.

4. A compound comprising the structure shown in Formula I:

$$R^3-(C=O)\text{-Xaa-Z}-R^4 \qquad \text{Formula I}$$

wherein
  Xaa is tyrosine or 3,5-diiodo-tyrosine;
  $R^3$ is independently a substituted or unsubstituted C(12-22)alkyl or C(12-22)alkenyl;
  $R^4$ is independently a substituted or unsubstituted C(12-22)alkyl or C(12-22)alkenyl;
  Z is NH;
wherein a peptide is attached to the side chain of Xaa;
and salts thereof.

5. The compound of claim 1, selected from (C12acyl)-tyrosine-NH—(C12alkyl), (C14acyl)-tyrosine-NH—(C14alkyl), (C16acyl)-tyrosine-NH—(C16alkyl), (C18acyl)-tyrosine-NH—(C18alkyl), (C18acyl)-tyrosine-NH—(C16alkyl), (C12acyl)-3, 5-diiodo-tyrosine-NH—(C12alkyl), (C14acyl)-3, 5-diiodo-tyrosine-NH—(C14alkyl), (C16acyl)-3,5-diiodo-tyrosine-NH—

(C16alkyl), (C18acyl)-3,5-diiodo-tyrosine-NH—(C18alkyl), (C18acyl)-3,5-diiodo-tyrosine-NH—(C16alkyl).

6. A composition comprising one or more compounds according to claim 1 and one or more therapeutic nucleic acids.

7. The composition of claim 6, wherein the therapeutic nucleic acid is a gene silencing agent.

8. The composition of claim 6, wherein the therapeutic nucleic acid is a RNAi-inducing agent.

9. The composition of claim 6, wherein the therapeutic nucleic acid is a double-stranded RNA.

10. The composition of claim 6, wherein the therapeutic nucleic acid is an mdRNA.

11. The composition of claim 6, wherein the therapeutic nucleic acid contains a modified nucleoside.

12. The composition of claim 6, further comprising cholesteryl hemisuccinate.

13. The composition of claim 6, further comprising one or more cationic lipids.

14. The composition of claim 6, wherein the composition contains liposomes.

15. A pharmaceutical composition comprising one or more compounds according to claim 1 and one or more drug agents or biologically active agents.

16. A method for inhibiting expression of a gene in a mammal comprising preparing a composition according to claim 6 and administering the composition to the mammal.

17. A method for treating a disease in a human, the disease being selected from rheumatoid arthritis, liver disease, encephalitis, bone fracture, heart disease, viral disease, hepatitis, influenza, sepsis, and cancer, the method comprising preparing a composition according to claim 6 and administering the composition to the human.

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggctcccagt tcttcatcac                                              20

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccttccgcac cacctc                                                  16

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
ctagatggca agcatgtggt gtttgg                                       26

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 4
tctatcatca acgggtacaa acga                                          24

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttttcagca agtgggaagg tg                                            22

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cctggccttg tctgtggaga cggatta                                       27

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-O-methyl uridine
<220> FEATURE:
<221> NAME/KEY: modified_base
<222> LOCATION: (10)
<223> OTHER INFORMATION: 2'-O-methyl uridine
<220> FEATURE:
<221> NAME/KEY: modified_base
<222> LOCATION: (12)..(14)
<223> OTHER INFORMATION: 2'-O-methyl uridine
<220> FEATURE:
<221> NAME/KEY: modified_base
<222> LOCATION: (19)
<223> OTHER INFORMATION: 2'-O-methyl cytidine
<220> FEATURE:
<221> NAME/KEY: misc_feature
<222> LOCATION: (20)..(21)
<223> OTHER INFORMATION: phosphorothioate linkage

<400> SEQUENCE: 7
ggaaucuuau auuugaucca a                                             21

<210> SEQ ID NO 8
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-O-methyl uridine
<220> FEATURE:
<221> NAME/KEY: modified_base
<222> LOCATION: (7)
```

```
<223> OTHER INFORMATION: 2'-O-methyl cytidine
<220> FEATURE:
<221> NAME/KEY: modified_base
<222> LOCATION: (11)
<223> OTHER INFORMATION: 2'-O-methyl uridine
<220> FEATURE:
<221> NAME/KEY: modified_base
<222> LOCATION: (13)
<223> OTHER INFORMATION: 2'-O-methyl uridine
<220> FEATURE:
<221> NAME/KEY: modified_base
<222> LOCATION: (18)
<223> OTHER INFORMATION: 2'-O-methyl uridine
<220> FEATURE:
<221> NAME/KEY: modified_base
<222> LOCATION: (21)
<223> OTHER INFORMATION: 2'-O-methyl cytidine
<220> FEATURE:
<221> NAME/KEY: modified_base
<222> LOCATION: (22)
<223> OTHER INFORMATION: 2'-O-methyl cytidine
<220> FEATURE:
<221> NAME/KEY: misc_feature
<222> LOCATION: (21)..(22)
<223> OTHER INFORMATION: phosphorothioate linkage
<220> FEATURE:
<221> NAME/KEY: misc_feature
<222> LOCATION: (22)..(23)
<223> OTHER INFORMATION: phosphorothioate linkage

<400> SEQUENCE: 8
uuggaucaaa uauaagauuc ccu                                        23

<210> SEQ ID NO 9
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
ggaucuuauu ucuucggaga caatg                                      25

<210> SEQ ID NO 10
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cauugucucc gaagaaauaa gauccuu                                    27

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
uucuccgaac gugucacgut t                                          21
```

```
<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
acgugacacg uucggagaat t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
cuacacaaau cagcgauuut t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
aaaucgcuga uuuguguagt c                                              21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ggaaagacug uuccaaaaau u                                              21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uuuuuggaac agucuuuccu u                                              21

<210> SEQ ID NO 17
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
ggaucuuauu ucuucggagt t                                             21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
cuccgaagaa auaagaucct t                                             21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccgtcagccg atttgctatt t                                             21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
auagcaaatc ggctgacggt t                                             21
```